(12) United States Patent
Pietrzik et al.

(10) Patent No.: US 11,420,995 B2
(45) Date of Patent: Aug. 23, 2022

(54) ANTI-INFECTIVE AND ANTI-INFLAMMATORY COMPOUNDS

(71) Applicants: Synovo GmbH, Tubingen (DE); Michael W. Burnet, Tubingen (DE)

(72) Inventors: Nikolas Pietrzik, Tübingen (DE); Michael W. Burnet, Tübingen (DE); Christiane Baeuerlein, Ofterdingen (DE); Mary Eggers, Ammerbuch (DE); Jan-Hinrich Guse, Rottenburg (DE); Ulrike Hahn, Ditzingen-Heimerdingen (DE); Simon Strass, Großbottwar (DE)

(73) Assignee: Synovo GmbH, Tubingen (DE)

( * ) Notice: Subject to any disclaimer, the term of this patent is extended or adjusted under 35 U.S.C. 154(b) by 0 days.

(21) Appl. No.: 16/490,459

(22) PCT Filed: Mar. 2, 2018

(86) PCT No.: PCT/US2018/020769
§ 371 (c)(1),
(2) Date: Aug. 30, 2019

(87) PCT Pub. No.: WO2018/161039
PCT Pub. Date: Sep. 7, 2018

(65) Prior Publication Data
US 2020/0262857 A1 Aug. 20, 2020

Related U.S. Application Data

(60) Provisional application No. 62/466,827, filed on Mar. 3, 2017.

(51) Int. Cl.
| | |
|---|---|
| *C07H 17/08* | (2006.01) |
| *C07C 217/40* | (2006.01) |
| *C07D 215/42* | (2006.01) |
| *C07D 401/04* | (2006.01) |
| *A61K 45/06* | (2006.01) |

(52) U.S. Cl.
CPC ........... *C07H 17/08* (2013.01); *C07C 217/40* (2013.01); *C07D 215/42* (2013.01); *C07D 401/04* (2013.01); *A61K 45/06* (2013.01)

(58) Field of Classification Search
CPC .... C07H 17/08; C07C 217/40; C07D 215/42; C07D 401/04; A61K 45/06
USPC .......................................................... 514/30
See application file for complete search history.

(56) References Cited

U.S. PATENT DOCUMENTS

| | | | |
|---|---|---|---|
| 3,520,919 A | 7/1970 | Crowther et al. | |
| 4,201,866 A | 5/1980 | Hasegawa | |
| 6,028,066 A | 2/2000 | Unger | |
| 9,550,802 B2* | 1/2017 | Burnet | C07D 498/08 |
| 2012/0232257 A1* | 9/2012 | Pietrzik | C07C 313/36 |
| | | | 536/17.2 |
| 2014/0315865 A1 | 10/2014 | Maciag et al. | |
| 2015/0232499 A1* | 8/2015 | Burnet | C07H 17/08 |
| | | | 536/7.1 |

FOREIGN PATENT DOCUMENTS

| | | |
|---|---|---|
| CN | 103588833 A | 2/2014 |
| JP | S55-151598 A | 11/1980 |
| JP | H02-225447 A | 9/1990 |
| WO | WO 1995/001794 A1 | 1/1995 |
| WO | WO 1997/042206 A1 | 11/1997 |
| WO | WO 1998/009978 A1 | 3/1998 |
| WO | WO 2001/012584 A1 | 2/2001 |
| WO | WO 2005/053685 A1 | 6/2005 |
| WO | WO 2005/070113 A2 | 8/2005 |
| WO | WO 2010/086350 * | 8/2010 |
| WO | WO 2013/008928 A1 | 1/2013 |
| WO | WO 2014/053592 A1 | 4/2014 |

OTHER PUBLICATIONS

Hassanzadeh et al. Determination of the stereochemistry of anhydroerythromycin A, the principal degradation product of the antibiotic erythromycin A. Org. Biomol. Chem., 2006, 4, 1014-1019. (Year: 2006).*
Koc et al. Medicinal Chemistry and Anti-Inflammatory Activity of Nitric Oxide-Releasing NSAI Drugs. Mini-Reviews in Medicinal Chemistry, 2009, 9, 611-619. (Year: 2009).*
International Search Report and Written Opinion dated Jun. 11, 2018 in connection with PCT/US2018/020769.
PubChem SID: 223811413. Erythromycin Nitrate. Deposited Feb. 2, 2015. 7 pages.
PubChem SID: 241027857. Deposited Feb. 16, 2015. 5 pages.
PubChem SID 274239515. (RS)-O-Acetylpropranolol. Deposited Dec. 18, 2015. 5 pages.
Mitsuyama et al., Release of nitric oxide and expression of constitutive nitric oxide synthase of human endothelial cells: enhancement by a 14-membered ring macrolide. Mol Cell Biochem. Apr. 1998;181(1-2):157-61.
Extended European Search Report for App No. 18761736.0 dated Mar. 7, 2022.
Irwin et al., Drug-delivery by ion-exchange. Hydrolysis and rearrangement of ester pro-drugs of propranolol. Int J Pharma. 1988;46(1-2):57-67.
Lewis et al., Catalytic site-selective synthesis and evaluation of a series of erythromycin analogs. Bioorg Med Chem Lett. Nov. 15, 2008; 18(22):6007-11. doi: 10.1016/j.bmcl.2008.09.019. Epub Sep. 9, 2008. PMID: 18819795; PMCID: PMC2669672.
Shameem et al., An In-vitro and In-vivo Correlative Approach to the Evaluation of Ester Prodrugs to Improve Oral Delivery of Propranolol. J Pharma Pharmacol. Apr. 12, 2011. 45(4):246-252.

(Continued)

Primary Examiner — Yih-Horng Shiao
(74) Attorney, Agent, or Firm — Wolf, Greenfield & Sacks, P.C.

(57) ABSTRACT

Lysosomally accumulated substances that release a nitroxy group, or a short chain fatty acid or a product of anaerobic metabolism or a thiol or a sulfide often from an ester or similar labile linkage have anti-inflammatory, anti-cancer and anti-bacterial activity. They are useful in treating infectious, inflammatory and malignant disease.

20 Claims, 21 Drawing Sheets

(56) References Cited

OTHER PUBLICATIONS

Wang et al., Nitric oxide donors: chemical activities and biological applications. Chem Rev. Apr. 2002;102(4):1091-134. doi: 10.1021/cr0000401. PMID: 11942788.

* cited by examiner

ANTI-INFECTIVE AND ANTI-INFLAMMATORY COMPOUNDS

CROSS-REFERENCE TO RELATED APPLICATIONS

This application is a national stage filing under 35 U.S.C. § 371 of international PCT application, PCT/US2018/020769, filed Mar. 2, 2018, which claims priority to U.S. Provisional Application No. 62/466,827, filed Mar. 3, 2017, each of which is incorporated herein by reference in its entirety.

BACKGROUND

The human body senses bacteria, fungi or other parasites by both recognition of their surface patterns and via reception of the metabolic products of those organisms. In particular, the immune system is sensitive to the presence of anaerobic organisms which, by their nature are able to infect poorly perfused tissue, or emanate from the anaerobic lumen of the gut. Anaerobes seem to be a particular source of danger signals for the immune system because they often produce toxins and are able to proliferate in the absence of oxygen, where immune cells are less active and less able to use oxidative burst to kill the bacteria they ingest.

Amongst the signals that human cells respond to are the products of fermentation such as the short chain fatty acids (SCFAs) acetate, propionate and butyrate. Less characterised mediators with similar function include: lactic acid, $H_2S$, HS—, nitrite, polyamines and similar decarboxylated amino acids such as 3-Indolepropionic acid (IPA), deoxybileacids and polyphenol metabolites like phenylpropionic acid. In a most general sense, these metabolites are variously sensed by a range of receptors that include SCFA receptors (e.g. FFA2), the pregnane X receptor or the arylhydrocarbon receptor. For convenience, we will describe here these materials as Products of Anaerobic Metabolism (PAM or PAMS for the plural). Another type of signal is that of bacterial cell wall materials or bacterial nucleic acids. These materials are often ligands for the Toll-like-receptor (TLR) family. These are referred to as Pathogen-associated molecular patterns or PAMPs. For simplicity here, we will refer to all signal types as PAM or PAM s in the plural.

Although signaling of this type is commonly associated with the gut epithelium, it is also a potential signal in the interaction between the immune system surveilling the gut or the periphery. In particular, the lysosomes of the gut or the immune system cells are exposed to bacterial metabolites because these materials are released as bacteria are lysed following phagocytosis.

We have observed that delivering donors of SCFAs, TLR ligands, and other bacterial metabolites to the phagosome of immune cells results in immune stimulation such that phagocytosed bacteria are more rapidly killed. This effect can be augmented by the presentation of additional signals in parallel, for example nitric oxide (NO), delivered from a nitro ester.

Nitric oxide functions as a neurotransmitter, autacoid constitutive mediator, inducible mediator, cytoprotective molecule, and cyctotoxic molecule. Since NO plays multiple physiological roles in the regulation of numerous and diverse organ functions, defects in the NO pathway lead to a variety of pathophysiological states. Possible disorders are: arterioscleroses, hypertension, coronary artery disease, cardiac failure, pulmonary hypertension, stroke, impotence, gastrointestinal ulcers, asthma, and other CNS and systemic disorders[1].

Synthetic chemical reagents that release NO continuously over a period of time, under physiological conditions, have been in use for a long time in treatment of cardiovascular diseases[2]. Most widely used are organic nitrates (e. g. glyceryl trinitrate): These NO donors need thiols as a cofactor for generating NO. They can use endogenous sources of thiols.

Other important series of NO donors are the so called NOC, NOR, and NONOate compounds which were reviewed by Wang et al[3].

Furthermore a class of activators of soluble guanylyl cyclase (e.g. YC-1) is known as NO-sensitizer, which may potentiate the effect of minimal NO concentrations[4].

One major drawback of all those NO donors consists in the fact that they exert their action largely in the extracellular environment. For example, nitro-glycerine leads to the release of NO in the plasma which stimulates vasodilation by its action on smooth muscle surrounding vessels.

A similar drawback for the use of short chain fatty acids or hydrogen sulfides as pharmaceutical agents is that they are potent odorants and required in relatively large amounts (the SCFA receptors have affinities in the milli-molar range). Thus they require specific delivery if they are to be effective.

Another difficulty in the use of NO donors is the synthetic methods. The preparation of nitro and nitrooxy compounds belongs to the most widespread examples for electrophilic substitution reactions. In general all methods for nitration lead to the formation of nitronium cations as electrophiles, in most cases generated in situ[5]. Few examples are published employing NO species as a salt, e.g. nitronium tetrafluoroborate that can be employed for highly regioselective aromatic nitration[6]. Obstacles common to all methods are, besides desired selectivity, relatively harsh reaction conditions: acidity, oxidizing reactants, and temperature. Thus, classical procedures are limited to stable systems that withstand these reaction conditions. Unfortunately this excludes many substance classes like drugs, organic molecules, reducing sugars or other natural products. Transformation of these compounds to corresponding nitrates would result in valuable compounds. Especially in the case of O-nitration synthesis faces several problems: Starting materials or intermediates in many cases do not withstand conventional reaction conditions like $HNO_3$—$H_2SO_4$-mixtures. Thus the strategy of synthesis has to be changed, utilizing mild nitrating agents like acetyl nitrate[7,8,9] or benzoyl nitrate[9,10,11,12], herein referred to as acyl nitrates. Chemically theses nitrating agents are mixed anhydrides from nitric acid and corresponding carboxylic acids, mainly generated in situ by reaction of a carboxylic anhydride with nitric acid.

NO has many biological functions and as such can serve as a molecular warhead if appropriately delivered by a carrier molecule. In this regard it shares properties in common with compounds like CO and $H_2S$. Another class of small effect molecule of natural origin are the short chain fatty acids (SCFAs) alluded to above. These compounds are products of fermentation and in the gut serve as signals of microbial metabolism which are received by the gut epithelium and in turn used to coordinate anti-microbial homeostasis and epithelial microbial modulation. Similarly, TLR ligands are regulators of the immune response.

While all of these small natural modulators are known as extracellular signals, there use as intracellular modulators is not described. Here we report compounds that are designed to release these molecules in the cytoplasm and more importantly, acidic organelles such as the phagosome or lysosome. Release of these molecules in the lysosome serves to inform the cell that it has digested a bacterium and thereby induces an anti-bacterial program that in turn enables a more robust response to intracellular organisms that may otherwise suppress bacteriolysis.

In particular we describe molecules which are acid trapped and able to donate a compound that is the product of anaerobic metabolism. Acid trapped compounds are often amine containing compounds that are amphiphilic. They partition into the cell and concentrate in acidic compartments due to their conversion to an ionized form at pH 5-6 which is common in such organelles. Such acid-trapped molecules can be prepared with suitable linking groups such as hydroxyl groups. Multiple hydroxyl groups may be used to anchor one or more active molecules. There are many such acid-trapped compounds including common drugs such as propranolol, amodiaquine, dextromethorphan, Dextrorphan, paroxetine, fluoxetine, astemizole or imipramine. Another example is the macrolide class including compounds such as azithromycin, erythromycin or clarithromycin which are "acid trapped" in lysosomes by virtue of their 2' amine groups and amphilic properties. Azithromycin has two amine groups and is particularly strongly trapped. These acid trapped molecules can be derivatized, that is, decorated with signaling molecules related to anaerobic metabolism such as SCFAs, NO, or HS— donors to form compounds of the invention. Using multiple signaling molecules, or combinations thereof in multiple positions allows for a flexible means to tune the properties of the molecules. For example, we described different effects for a compound carrying 3 SCFA esters versus one carrying a NO ester and a SCFA or a thiol donor and an SCFA. In particular, there is a hierarchy of effect with longer fatty acids promoting differing immune responses. For example propionate differs from acetate in the degree of effect in this setting.

SUMMARY

The invention relates to compounds useful in modulating immune cell activity or the barrier function of epithelial cells. The invention comprises compounds (e.g., derivative compounds of Amphiphilic Lysosomally trapped Compounds (ALC), such ALC compounds including those of the formulae in any tables herein), which are subject to lysosomal trapping and which bear moieties that are able to release TLR ligands, products of anaerobic metabolism, specifically SCFAs, sulfides, lactates, or NO, bile acids, polyamines, decarboxylated amino acids and polyphenol metabolites like phenylpropionic acid.

The invention also provides a method of identifying a compound useful for modulating immune cell activity against bacteria: incubating such a compound with blood cells, preferably leukocytes, providing those cells with bacteria, incubating the cells with bacteria, washing the cells and treating them with a non-permeable antibiotic to reduce extracellular bacteria, then counting intracellular bacteria to observe which compounds reduce the number of intracellular bacteria surviving.

Optionally, it is advantageous to determine the ratio of the concentration of the compound in the immune cells to non-immune cells such as erythrocytic cells as a measure of its lysosomal partition. Preferred are compounds that are preferentially taken up by immune cells.

In some embodiments the carrier compounds are macrolides with at least one $ONO_2—$, $SNO_2—$ or $NNO_2$-moiety.

In other embodiments the carrier compounds are macrolides with at least one SCFA-moiety. In other embodiments, the carrier molecule is amphiphilic with at least one protonatable amine. The term "macrolide" refers to any macrocyclic lactone with 10 or more atoms connected within the ring system. Reference to an atom includes all isotopes of that atom. For example, structures drawn with carbon or hydrogen include isotopes such as $^{13}C$ or $^{2}H$.

An anti-microbial compound is a compound that inhibits the growth or division or replication of an organism such as a virus, bacteria, fungus, parasite, *mycoplasma* or other pathogen.

One embodiment is a compound comprising an Amphiphilic Lysosomally trapped Compound (ALC) conjugated via an ester, thioester or nitroester to a product of Anaerobic Metabolism (PAM) or one or more PAMs of the same or different types. In a further embodiment, the compound is one in which the PAM is selected from one or more of Short Chain Fatty Acid (SCFA), NO, $H_2S$, mercaptans, polyamines, decarboxylated amino acids or polyphenol metabolites like phenylpropionic acid. In a further embodiment, the compound is one in which the ALC is selected from a macrolide, polyamine, propranolol analog, chloroquine analog, amodiaquine, dextromethorphan, dextrorphan, paroxetine, fluoxetine, astemizole or imipramine analog.

Another embodiment is a macrolide comprising at least one $ONO_2—$, $SNO_2—$ or $NNO_2$ moiety.

In some embodiments, the compound has the following formula (including any possible salts thereof, except for nitrates, and any structures with exchanged isotopes, as possible by state of the art):

Formula 1

ALC conjugated or esterified with 1 or more of any of: $X_{(1-5)}$, $Y_{(0-5)}$, $Z_{(0-3)}$;

Where ALC=Amphiphilic Lysosomally trapped Compound;

X is a SCFA esterified to ALC and 0-5 indicates the number of moieties conjugated;

Y is an NO donating group or an $H_2S$ donating group esterified to ALC and 0-5 indicates the number of moieties conjugated;

Z is a group donating sulfides, polyamines, decarboxylated amino acids or polyphenol metabolites like phenylpropionic acid.

Formula 2: compounds of Formula 1, wherein ALC is a macrolide of the formula

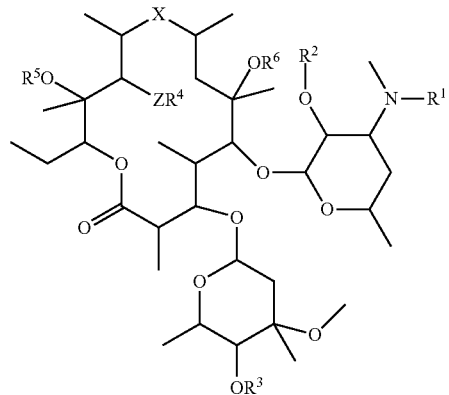

Wherein,
X=—N(CH$_3$)—CH$_2$—,
—CH$_2$—N(CH$_3$)—;
—C(=O)—;
—C(=NOR$^8$)—;
—C(=NR$^{12}$)—;
R$^1$ can be, but is not limited to
—(C$_1$-C$_{10}$)alkyl;
—(C$_1$-C$_{10}$)alkyliden-OH;
—(C$_1$-C$_{10}$)alkyliden-ONO$_2$;
R$^2$ can be, but is not limited to:
—H;
—NO$_{(y)}$ with y=1 or 2;
—C(=O)OR$^7$, —C(=S)OR$^7$, —C(=O)R$^7$, —C(=S)R$^7$, —C(=O)(NH)R$^7$, —C(=S)(NH)R$^7$;
R$^3$ can be, but is not limited to:
—H;
—NO$_{(y)}$ with y=1 or 2;
—C(=O)OR$^7$, —C(=S)OR$^7$, —C(=O)R$^7$, —C(=S)R$^7$, —C(=O)(NH)R$^7$, —C(=S)(NH)R$^7$;
If Z=O, R$_4$ can be, but is not limited to:
—H;
—NO$_{(y)}$ with y=1 or 2;
—C(=O)OR$^7$, —C(=S)OR$^7$, —C(=O)R$^7$, —C(=S)R$^7$, —C(=O)(NH)R$^7$, —C(=S)(NH)R$^7$;
R$_5$ can be, but is not limited to:
—H;
—NO$_{(y)}$ with y=1 or 2;
—C(=O)OR$^7$, —C(=S)OR$^7$, —C(=O)R$^7$, —C(=S)R$^7$, —C(=O)(NH)R$^7$, —C(=S)(NH)R$^7$;
or Z=O or NR$^9$ and the R$^4$ and R$^5$ bearing atoms are connected via
—C(=O)— (If Z=O: carbonate linkage, if Z=NR$^9$: carbamate linkage) or the R$^4$ and R$^5$ bearing atoms are connected via W;
W may be but is not limited to
—(-)CH—(C$_1$-C$_{12}$)alkyl;
—(-)CH—(C$_3$-C$_{12}$)alkenyl;
—(-)CH—(C$_3$-C$_{12}$)alkynyl;
—(-)CH—(C$_1$-C$_8$)[(C$_1$-C$_4$)alkoxy]alkyl;
—(-)CH—(C$_1$-C$_8$)[(C$_1$-C$_4$)alkoxy]alkenyl;
wherein alkyl, alkenyl, alkynyl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxy, nitro, cyano, azido, mercapto, —NR$^{14}$R$^{15}$, R$^{14}$C(=O)—, R$^{14}$C(=O)O—, R$^{14}$OC(=O)O—, R$^{14}$NHC(=O)—, R$^{14}$C(=O)NH—, R$^{14}$R$^{15}$NC(=O)—, R$^{14}$OC(=O)—, and -xNO$_2$ with x=O; S;N;
R$^6$ can be, but is not limited to:
—H;
—NO$_{(y)}$ with y=1 or 2;
—C(=O)OR$^7$, —C(=S)OR$^7$, —C(=O)R$^7$, —C(=S)R$^7$, —C(=O)(NH)R$^7$, —C(=S)(NH)R$^7$;
R$^7$ can be independently chosen from:
—H;
-ferrocene;
—C$_1$-C$_{10}$ alkyl, alkenyl, alkynyl, aryl, heteroaryl, alkylaryl, alkylheteroaryl wherein alkyl, alkenyl, alkynyl, aryl, heteroaryl, alkylaryl and alkylheteroaryl groups are optionally substituted by one to five substituents selected independently from: ferrocene, halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxyl (—OH), nitro (—NO$_2$), cyano (—CN), azido (—N$_3$), mercapto (—SH), —NR$^{14}$R$^{15}$, R$^{14}$C(=O)—, R$^{14}$C(=O)O—, R$^{14}$OC(=O)O—, R$^{14}$NHC(=O)—, R$^{14}$C(=O)NH—, R$^{14}$R$^{15}$NC(=O)—, R$^{14}$OC(=O)—, and —XNO$_{(y)}$ with X=O; S; N and y=1 or 2;
R$^8$ can be, but is not limited to:
—H;
—NO$_{(y)}$ with y=1 or 2;
—C(=O)—R$^7$;
—(C$_1$-C$_{12}$)alkyl;
—(C$_1$-C$_{12}$)alkenyl;
—(C$_1$-C$_{12}$)alkynyl;
—(C$_1$-C$_8$)[(C$_1$-C$_4$)alkoxy]alkyl;
—(C$_1$-C$_8$)[(C$_1$-C$_4$)alkoxy]alkenyl;
—(C$_6$-C$_{10}$)aryl-(C$_1$-C$_5$)alkyl;
—(C$_2$-C$_9$)heteroaryl-(C$_1$-C$_5$)alkyl;
R$^9$ can be, but is not limited to
—H;
—NO$_{(y)}$ with y=1 or 2;
—C(=O)—R$^7$;
—(C$_1$-C$_{12}$)alkyl;
—(C$_1$-C$_{12}$)alkenyl;
—(C$_1$-C$_{12}$)alkynyl;
—(C$_1$-C$_8$)[(C$_1$-C$_4$)alkoxy]alkyl;
—(C$_1$-C$_8$)[(C$_1$-C$_4$)alkoxy]alkenyl;
—(C$_6$-C$_{10}$)aryl-(C$_1$-C$_5$)alkyl;
—(C$_2$-C$_9$)heteroaryl-(C$_1$-C$_5$)alkyl;
R$^{12}$ can be, but is not limited to:
—H;
—NO$_{(y)}$ with y=1 or 2;
—C(=O)—R$^7$;
—(C$_1$-C$_{12}$)alkyl;
—(C$_1$-C$_{12}$)alkenyl;
—(C$_1$-C$_{12}$)alkynyl;
—(C$_1$-C$_8$)[(C$_1$-C$_4$)alkoxy]alkyl;
—(C$_1$-C$_8$)[(C$_1$-C$_4$)alkoxy]alkenyl;
—(C$_6$-C$_{10}$)aryl-(C$_1$-C$_5$)alkyl;
—(C$_2$-C$_9$)heteroaryl-(C$_1$-C$_5$)alkyl;
R$^{14}$, R$^{15}$ can independently be, but are not limited to:
—H;
—(C$_1$-C$_{12}$)alkyl;
—(C$_1$-C$_{12}$)alkenyl;
—(C$_1$-C$_{12}$)alkynyl;
—(C$_1$-C$_8$)[(C$_1$-C$_4$)alkoxy]alkyl;
—(C$_1$-C$_8$)[(C$_1$-C$_4$)alkoxy]alkenyl;
—(C$_6$-C$_{10}$)aryl-(C$_1$-C$_5$)alkyl;
—(C$_2$-C$_9$)heteroaryl-(C$_1$-C$_5$)alkyl
wherein alkyl, alkenyl, alkynyl, aryl and heteroaryl are optionally substituted by one to five substituents selected independently from halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_6$)heterocycloalkyl, (C$_6$-C$_{10}$)aryl, (C$_1$-C$_9$)heteroaryl, (C$_1$-C$_4$)alkoxy, hydroxyl (—OH), nitro (—NO$_2$), cyano (—CN), azido (—N$_3$), mercapto (—SH), and —XNO$_y$ with X=O; S; N and y=1 or 2;
or N(R$^{14}$R$^{15}$) is an aziridine, azetidine, pyrrolidine, piperidine, azepane or azocane, 1-substituted piperazine, or morpholine moiety.

In some embodiments, the compound has the following formula (including any possible salts thereof, except for nitrates, and any structures with exchanged isotopes, as possible by state of the art):

Formula 1

ALC conjugated or esterified with 1 or more of any of: $X_{(1-5)}, Y_{(0-5)}, Z_{(0-3)}$;

Where ALC=Amphiphilic Lysosomally trapped Compound;

X is a SCFA esterified to ALC and 0-5 indicates the number of moieties conjugated;

Y is an NO donating group or an $H_2S$ donating group esterified to ALC and 0-5 indicates the number of moieties conjugated;

Z is a group donating sulfides, polyamines, decarboxylated amino acids or polyphenol metabolites like phenylpropionic acid.

Formula 2: compounds of Formula 1,
wherein ALC is a macrolide of the formula

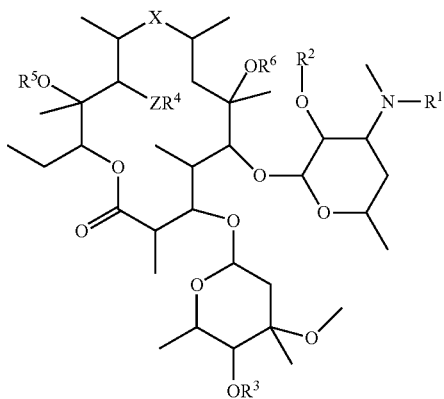

Wherein,
X=—N($CH_3$)—$CH_2$—,
—$CH_2$—N[($CH_2$)$_n$$CH_3$]—; wherein n is 0-4;
—C(=O)—;
—C(=$NOR^8$)—;
—C(=$NR^{12}$)—;
$R^1$ can be, but is not limited to
—($C_1$-$C_{10}$)alkyl;
—($C_1$-$C_{10}$)alkyliden-OH;
—($C_1$-$C_{10}$)alkyliden-$ONO_2$;
$R^2$ can be, but is not limited to:
—H;
—$NO_{(y)}$ with y=1 or 2;
—C(=O)$OR^7$, —C(=S)$OR^7$, —C(=O)$R^7$, —C(=S)$R^7$, —C(=O)(NH)$R^7$, —C(=S)(NH)$R^7$;
$R^3$ can be, but is not limited to:
—H;
—$NO_{(y)}$ with y=1 or 2;
—C(=O)$OR^7$, —C(=S)$OR^7$, —C(=O)$R^7$, —C(=S)$R^7$, —C(=O)(NH)$R^7$, —C(=S)(NH)$R^7$;
If Z=O, $R^4$ can be, but is not limited to:
—H;
—$NO_{(y)}$ with y=1 or 2;
—C(=O)$OR^7$, —C(=S)$OR^7$, —C(=O)$R^7$, —C(=S)$R^7$, —C(=O)(NH)$R^7$, —C(=S)(NH)$R^7$;
$R^5$ can be, but is not limited to:
—H;
—$NO_{(y)}$ with y=1 or 2;
—C(=O)$OR^7$, —C(=S)$OR^7$, —C(=O)$R^7$, —C(=S)$R^7$, —C(=O)(NH)$R^7$, —C(=S)(NH)$R^7$;
or Z=O or $NR^9$ and the $R^4$ and $R^5$ bearing atoms are connected via —C(=O)— (If Z=O: carbonate linkage, if Z=$NR^9$: carbamate linkage) or the $R^4$ and $R^5$ bearing atoms are connected via W;

W may be but is not limited to:
—(-)CH—($C_1$-$C_{12}$)alkyl;
—(-)CH—($C_3$-$C_{12}$)alkenyl;
—(-)CH—($C_3$-$C_{12}$)alkynyl;
—(-)CH—($C_1$-$C_8$)[($C_1$-$C_4$)alkoxy]alkyl;
—(-)CH—($C_1$-$C_8$)[($C_1$-$C_4$)alkoxy]alkenyl;
wherein alkyl, alkenyl, alkynyl are optionally substituted by one to five substituents selected independently from halogen (as can be F, Cl, Br, I), ($C_1$-$C_4$)alkyl, ($C_1$-$C_4$)alkenyl, ($C_1$-$C_4$)alkynyl, ($C_3$-$C_7$)cycloalkyl, ($C_1$-$C_6$)heterocycloalkyl, ($C_6$-$C_{10}$)aryl, ($C_1$-$C_9$)heteroaryl, ($C_1$-$C_4$)alkoxy, hydroxy, nitro, cyano, azido, mercapto, —$NR^{14}R^{15}$, $R^{14}$C(=O)—, $R^{14}$C(=O)O—, $R^{14}$OC(=O)O—, $R^{14}$NHC(=O)—, $R^{14}$C(=O)NH—, $R^{14}R^{15}$NC(=O)—, $R^{14}$OC(=O)—, and x$NO_2$ with x=O; S;N;

$R^6$ can be, but is not limited to:
—H;
—$NO_{(y)}$ with y=1 or 2;
—C(=O)$OR^7$, —C(=S)$OR^7$, —C(=O)$R^7$, —C(=S)$R^7$, —C(=O)(NH)$R^7$, —C(=S)(NH)$R^7$;

$R^7$ can be independently chosen from:
—H;
-ferrocene;
—$C_1$-$C_{10}$ alkyl, alkenyl, alkynyl, aryl, heteroaryl, alkylaryl, alkylheteroaryl wherein alkyl, alkenyl, alkynyl, aryl, heteroaryl, alkylaryl and alkylheteroaryl groups are optionally substituted by one to five substituents selected independently from: ferrocene, halogen (as can be F, Cl, Br, I), ($C_1$-$C_4$)alkyl, ($C_1$-$C_4$)alkenyl, ($C_1$-$C_4$)alkynyl, ($C_3$-$C_7$)cycloalkyl, ($C_1$-$C_6$)heterocycloalkyl, ($C_6$-$C_{10}$)aryl, ($C_1$-$C_9$)heteroaryl, ($C_1$-$C_4$)alkoxy, hydroxyl (—OH), nitro (—$NO_2$), cyano (—CN), azido (—$N_3$), mercapto (—SH), —$NR^{14}R^{15}$, $R^{14}$C(=O)—, $R^{14}$C(=O)O—, $R^{14}$OC(=O)O—, $R^{14}$NHC(=O)—, $R^{14}$C(=O)NH—, $R^{14}R^{15}$NC(=O)—, $R^{14}$OC(=O)—, and —$XNO_{(y)}$ with X=O; S; N and y=1 or 2;

$R^8$ can be, but is not limited to:
—H;
—$NO_{(y)}$ with y=1 or 2;
—C(=O)—$R^7$;
—($C_1$-$C_{12}$)alkyl;
—($C_1$-$C_{12}$)alkenyl;
—($C_1$-$C_{12}$)alkynyl;
—($C_1$-$C_8$)[($C_1$-$C_4$)alkoxy]alkyl;
—($C_1$-$C_8$)[($C_1$-$C_4$)alkoxy]alkenyl;
—($C_6$-$C_{10}$)aryl-($C_1$-$C_5$)alkyl;
—($C_2$-$C_9$)heteroaryl-($C_1$-$C_5$)alkyl;

$R^9$ can be, but is not limited to
—H;
—$NO_{(y)}$ with y=1 or 2;
—C(=O)—$R^7$;
—($C_1$-$C_{12}$)alkyl;
—($C_1$-$C_{12}$)alkenyl;
—($C_1$-$C_{12}$)alkynyl;
—($C_1$-$C_8$)[($C_1$-$C_4$)alkoxy]alkyl;
—($C_1$-$C_8$)[($C_1$-$C_4$)alkoxy]alkenyl;
—($C_6$-$C_{10}$)aryl-($C_1$-$C_5$)alkyl;
—($C_2$-$C_9$)heteroaryl-($C_1$-$C_5$)alkyl;

$R^{12}$ can be, but is not limited to:
—H;
—$NO_{(y)}$ with y=1 or 2;
—C(=O)—$R^7$;

—($C_1$-$C_{12}$)alkyl;
—($C_1$-$C_{12}$)alkenyl;
—($C_1$-$C_{12}$)alkynyl;
—($C_1$-$C_8$)[($C_1$-$C_4$)alkoxy]alkyl;
—($C_1$-$C_8$)[($C_1$-$C_4$)alkoxy]alkenyl;
—($C_6$-$C_{10}$)aryl-($C_1$-$C_5$)alkyl;
—($C_2$-$C_9$)heteroaryl-($C_1$-$C_5$)alkyl;
$R^{14}$, $R^{15}$ can independently be, but are not limited to:
—H;
—($C_1$-$C_{12}$)alkyl;
—($C_1$-$C_{12}$)alkenyl;
—($C_1$-$C_{12}$)alkynyl;
—($C_1$-$C_8$)[($C_1$-$C_4$)alkoxy]alkyl;
—($C_1$-$C_8$)[($C_1$-$C_4$)alkoxy]alkenyl;
—($C_6$-$C_{10}$)aryl-($C_1$-$C_5$)alkyl;
—($C_2$-$C_9$)heteroaryl-($C_1$-$C_5$)alkyl;
wherein alkyl, alkenyl, alkynyl, aryl and heteroaryl are optionally substituted by one to five substituents selected independently from halogen (as can be F, Cl, Br, I), ($C_1$-$C_4$)alkyl, ($C_1$-$C_4$)alkenyl, ($C_1$-$C_4$)alkynyl, ($C_3$-$C_7$)cycloalkyl, ($C_1$-$C_6$)heterocycloalkyl, ($C_6$-$C_{10}$) aryl, ($C_1$-$C_9$)heteroaryl, ($C_1$-$C_4$)alkoxy, hydroxyl (—OH), nitro (—$NO_2$), cyano (—CN), azido (—$N_3$), mercapto (—SH), and —$XNO_y$ with X=O; S; N and y=1 or 2 or N($R^{14}R^{15}$) is an aziridine, azetidine, pyrrolidine, piperidine, azepane or azocane, 1-substituted piperazine, or morpholine moiety.

In some other embodiments, the compound has the following formula (including any possible salts thereof, except for nitrates, and any structures with exchanged isotopes, as possible by state of the art):

Formula 3: compounds of Formula 1, wherein ALC is a macrolide of the formula

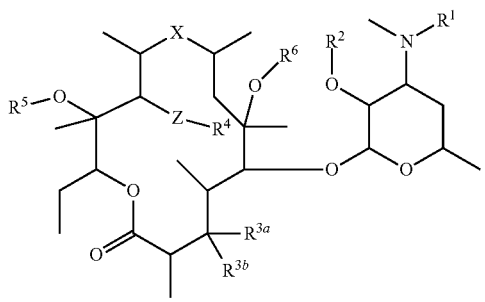

Wherein $R^1$, $R^2$, $R^4$, $R^5$, $R^6$, X, and Z are defined as in formula 2;
$R^{3a}$, $R^{3b}$=both —H;
or in the case $R^{3a}$ is —H, $R^{3b}$ can be:
—OH;
—$OR^{14}$;
—$NR^{14}R^{15}$;
—C(=O)—$R^7$;
or $R^{3a}=R^{3b}$=(=O);
=any possible cyclic or non-cyclic acetal;
(=$NR^{12}$);
=any possible cyclic or non-cyclic aminal;
—OC(=O)$R^7$;
$OR^{14}$;
and $R^7$, $R^{14}$, and $R^{15}$ are defined as in formula 2.

Formula 4: compounds of Formula 1, wherein ALC is a propanolol of the formula

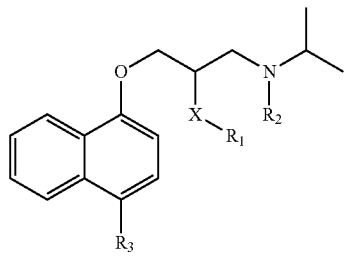

Where X can be O or S;
When X=O, $R_1$ may be but not limited to —(C=O)$CH_3$, —(C=O)$CH_2CH_3$, —(C=O)$CH_2CH_2CH_3$, —(C=O)$CH_2CH_2$COOH, —(C=O)(C=O)$CH_3$, —(C=O)CHCHCOOH, —(C=O)CH(OH)$CH_3$, —(C=O)C($CH_3$)$_2$, —(C=O)$CH_2CH_2CH_2CH_3$, —(C=O)$CH_2$C($CH_3$)$_2$, —(C=O)$CH_2CH_2CH_2CH_2$Y, or —(C=O)CH($ONO_2$)$CH_3$;
$R_2=R_3$=H;
Y=can be a 5-membered saturated ring containing a disulfide bond;
When X=O, $R_1$ may be but not limited to —(C=O)$CH_3$, —(C=O)$CH_2CH_3$, —(C=O)$CH_2CH_2CH_3$, —(C=O)$CH_2CH_2$COOH, —(C=O)(C=O)$CH_3$, —(C=O)CHCHCOOH, —(C=O)CH(OH)$CH_3$, —(C=O)C($CH_3$)$_2$, —(C=O)$CH_2CH_2CH_2CH_3$, —(C=O)$CH_2$C($CH_3$)$_2$, —(C=O)$CH_2CH_2CH_2CH_2$Y, or —(C=O)CH($ONO_2$)$CH_3$;
$R_2$=$CH_3$; $R_3$=H; or
When X=O, $R_1$=$NO_2$; $R_2$ consists of linker —$CH_2CH_2OR_4$, where $R_4$ may be but not limited to —(C=O)$CH_3$, —(C=O)$CH_2CH_3$, —(C=O)$CH_2CH_2CH_3$, —(C=O)$CH_2CH_2$COOH, —(C=O)(C=O)$CH_3$, —(C=O)CHCHCOOH, —(C=O)CH(OH)$CH_3$, —(C=O)C($CH_3$)$_2$, —(C=O)$CH_2CH_2CH_2CH_3$, —(C=O)$CH_2$C($CH_3$)$_2$, or —(C=O)$CH_2CH_2CH_2CH_2$Y; $R_3$=H;
Y=can be a 5-membered saturated ring containing a disulfide bond; or
When X=O, $R_1$ may be but not limited to —(C=O)$CH_3$, —(C=O)$CH_2CH_3$, —(C=O)$CH_2CH_2CH_3$, —(C=O)$CH_2CH_2$COOH, —(C=O)(C=O)$CH_3$, —(C=O)CHCHCOOH, —(C=O)CH(OH)$CH_3$, —(C=O)C($CH_3$)$_2$, —(C=O)$CH_2CH_2CH_2CH_3$, —(C=O)$CH_2$C($CH_3$)$_2$, —(C=O)$CH_2CH_2CH_2CH_2$Y, or —(C=O)CH($ONO_2$)$CH_3$;
Y=can be a 5-membered saturated ring containing a disulfide bond;
$R^2$ consists of linker —$CH_2CH_2OR_4$, where $R_4$=$NO_2$; $R_3$=H; or
When X=O, $R_1$ is $NO_2$, $R_2$=H or $CH_3$, $R_3$=$OR_5$, where $R_5$ may be but not limited to —(C=O)$CH_3$, —(C=O)$CH_2CH_3$, —(C=O)$CH_2CH_2CH_3$, —(C=O)$CH_2CH_2$COOH, —(C=O)(C=O)$CH_3$, —(C=O)CHCHCOOH, —(C=O)CH(OH)$CH_3$, —(C=O)C($CH_3$)$_2$, —(C=O)$CH_2CH_2CH_2CH_3$, —(C=O)$CH_2$C($CH_3$)$_2$, —(C=O)$CH_2CH_2CH_2CH_2$Y, or —(C=O)CH($ONO_2$)$CH_3$;
Y=can be a 5-membered saturated ring containing a disulfide bond; or
When X=S, $R^1$ may be but not limited to —(C=O)$CH_3$, a metal salt, or forms a disulfide bridge with itself, $R^2$=$R^3$=H.

Definition of substituents on ALC formulae (e.g., Macrolides, hydroxychloroquine, Propranolol, etc.)

| | |
|---|---|
| —NO$_2$ | Nitro |
| —(C=O)—C$_6$H$_4$—NO$_2$ | p-nitrobenzoyl |
| —(C=O)C$_6$H$_5$ | benzoyl |
| —(C=O)CH$_2$CH$_2$COOH | succinyl |
| —(C=O)CH$_2$CH$_3$ | propionyl |
| —(C=O)CH$_2$CH$_2$CH$_3$ | butyryl |
| —(C=O)CH$_3$ | acetyl |
| —(C=O)(C=O)CH$_3$ | Pyruvyl |
| —(C=O)CHCHCOOH | Maleyl |
| —(C=O)CH(OH)CH$_3$ | Lactyl |
| —(C=O)CH(ONO$_2$)CH$_3$ | 2-O-Nitrolactyl |
| —(C=O)C(CH$_3$)$_2$ | Isobutyryl |
| —(C=O)CH$_2$CH$_2$CH$_2$CH$_3$ | Valeryl |
| —(C=O)CH$_2$C(CH$_3$)$_2$ | Isovalericyl |
| —(C=O)CH(CH$_3$)O(C=O)CH$_3$ | Acetoxypropionyl |
| —(C=O)CH$_2$CH$_2$(C=O)—Z | Succinyl-dithiole-3-thione |
| —(C=O)OCH$_2$CH$_2$S(S)$_n$H | Polysulfide ethyl carbonate |
| —(C=O)OCH$_2$CH$_2$SNO | NO-thioethylcarbonate |
| —(C=S)OC$_6$H$_5$ | O-Phenylchlorothiono carbonate |
| —(C=O)CH$_2$CH$_2$CH$_2$CH$_2$CH$_3$ | hexanoyl |
| —CH$_2$CH$_2$Br | bromoethyl |
| —(C=O)OCH$_2$CHCH$_2$ | Vinyl carbonate |
| —(C=O)CH$_2$CH$_2$CH$_2$CH$_2$Y | Lipoyl |

Z=

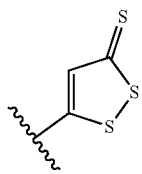 [SMILES: *c1cc(=S)ss1]

Y=

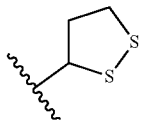 [SMILES: *C1CCSS1]

Formula 5: Compounds with the structure

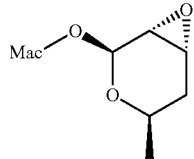

Wherein
Mac=a macrolide ring or macrolide ring system, for example, but not limited to azithromycin or gamithromycin, each without the desosamin residue.

Compounds with the Structure

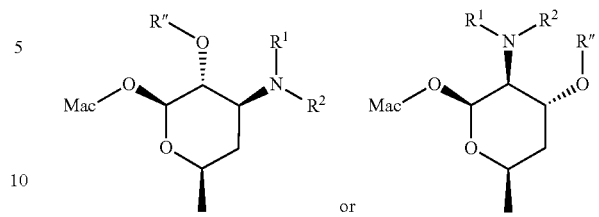

or

Wherein
Mac=a macrolide ring or macrolide ring system, for example, but not limited to azithromycin or gamithromycin, each without the desosamin residue;
R"=independently of each other
—H;
—NO$_{(y)}$ with y=1 or 2;
—C(=O)OR$^3$, —C(=S)OR$^3$, —C(=O)R$^3$, —C(=S)R$^3$, —C(=O)(NH)R$^3$, —C(=S)(NH)R$^3$;
R$^1$, R$^2$=independently of each other H, OH, OR$^4$, —C$_1$-C$_{10}$, alkyl, alkenyl, alkynyl, aryl, heteroaryl, alkylaryl, alkylheteroaryl;
wherein alkyl, alkenyl, alkynyl, aryl, heteroaryl, alkylaryl and alkylheteroaryl groups are optionally substituted by one to five substituents selected independently from:
fluorine, (C$_1$-C$_4$)alkyl, (C$_1$-C$_4$)alkenyl, (C$_1$-C$_4$)alkynyl, (C$_3$-C$_7$)cycloalkyl, (C$_1$-C$_9$)heterocycloalkyl, (C$_6$-C$_{10}$)aryl, (C$_1$-C$_9$)heteroaryl, (C$_1$-C$_4$)alkoxy, hydroxyl (—OH), nitro (—NO$_2$), cyano (—CN), azido (—N$_3$), mercapto (—SH), (C$_1$-C$_4$)alkthio, —NR$^4$R$^5$, R$^4$C(=O)—, R$^4$C(=O)O—, R$^4$OC(=O)O—, R$^4$NHC(=O)—, R$^4$C(=O)NH—, R$^4$R$^5$NC(=O)—, R$^4$OC(=O)—, and —XNO$_{(y)}$ with X=O; S; N and y=1 or 2;
or N(R$^1$R$^2$) is an aziridine, azetidine, pyrrolidine, piperidine, azepane or azocane, 1-substituted piperazine, or morpholine moiety;
R$^3$=—C$_1$-C$_{10}$ alkyl, alkenyl, alkynyl, aryl, heteroaryl, alkylaryl, alkylheteroaryl wherein alkyl, alkenyl, alkynyl, aryl, heteroaryl, alkylaryl and alkylheteroaryl groups are optionally substituted by one to five substituents selected independently from: halogen, (C$_1$-C$_4$)alkyl, (C$_1$-C$_4$)alkenyl, (C$_1$-C$_4$)alkynyl, (C$_3$-C$_7$)cycloalkyl, (C$_1$-C$_9$)heterocycloalkyl, (C$_6$-C$_{10}$)aryl, (C$_1$-C$_9$)heteroaryl, (C$_1$-C$_4$)alkoxy, hydroxyl (—OH), nitro (—NO$_2$), cyano (—CN), azido (—N$_3$), mercapto (—SH), (C$_1$-C$_4$)alkthio, —NR$^6$R$^7$, R$^6$C(=O)—, R$^6$C(=O)O—, R$^6$OC(=O)O—, R$^6$NHC(=O)—, R$^6$C(=O)NH—, R$^6$R$^7$NC(=O)—, R$^6$OC(=O)—, and —XNO$_{(y)}$ with X=O; S; N and y=1 or 2;
R$^4$, R$^5$, R$^6$ and R$^7$ can independently be, but are not limited to:
—H;
—(C$_1$-C$_{12}$)alkyl;
—(C$_1$-C$_{12}$)alkenyl;
—(C$_1$-C$_{12}$)alkynyl;
—(C$_1$-C$_8$)[(C$_1$-C$_4$)alkoxy]alkyl;
—(C$_1$-C$_8$)[(C$_1$-C$_4$)alkoxy]alkenyl;
—(C$_6$-C$_{10}$)aryl-(C$_1$-C$_5$)alkyl;
—(C$_2$-C$_9$)heteroaryl-(C$_1$-C$_5$)alkyl;
wherein alkyl, alkenyl, alkynyl, aryl and heteroaryl are optionally substituted by one to five substituents selected independently from ferrocene, halogen (as can be F, Cl, Br, I), (C$_1$-C$_4$)alkyl, (C$_1$-C$_4$)alkenyl, (C$_1$-C$_4$)alkynyl, (C$_3$-C$_7$)cycloalkyl, (C$_1$-C$_9$)heterocycloalkyl, (C$_6$-C$_{10}$)aryl, (C$_1$-C$_9$)heteroaryl, (C$_1$-C$_4$)alkoxy, hydroxyl (—OH), (C$_1$-C$_6$)acyloxy, nitro (—NO$_2$), cyano (—CN), azido (—N$_3$), mercapto (—SH), and —XNO$_y$ with X=O; S; N and y=1 or 2.

Unless, otherwise stated, the word "macrolide" herein refers to the family of well-known macrolactone antibiotics and also the various macrolactone ALCs described herein.

In one aspect, the invention provides a composition comprising a compound of any of the formulae herein (e.g., any of the formulae, any formula in the tables herein), or salt, solvate, hydrate or prodrug thereof, and a pharmaceutically acceptable carrier. In a further aspect, the composition can further comprise an additional therapeutic agent.

In one aspect, the invention provides a method of treating a subject suffering from or susceptible to a disease, disorder, or symptom thereof. The method includes administering to a subject in need thereof a therapeutically effective amount of a compound of any of the formulae herein (e.g., any of the formulae, any formula in the tables herein), or salt, solvate, hydrate or prodrug thereof. The disease, disorder, or symptom thereof can be, for example, an infectious disease, an inflammatory disease, a malignant disease, a bacterial infection, an inflammatory reaction to a bacterial translocation event, an inflammation of the GI tract including intestines, colon, liver and pancreas, an inflammation of the airways, a systemic inflammatory disease or a malignant or neoplastic disease.

In one aspect, the invention provides a method of stimulating immune or epithelial cells to form an anti-infective barrier or anti-infective response comprising contacting the cells with a compound of any of the formulae herein (e.g., any of the formulae, any formula in the tables herein), or salt, solvate, hydrate or prodrug thereof. A further aspect of the method is wherein the contacting results in the intracellular release of a PAM comprising one or more of a molecule type selected from SCFA, NO, H$_2$S, sulfides, polyamines, decarboxylated amino acids or polyphenol metabolites like phenylpropionic acid from the compound of any of the formulae herein (e.g., any of the formulae, any formula in the tables herein), or salt, solvate, hydrate or prodrug thereof. A further aspect of the method is that comprising the intracellular release of one or more types of a short chain fatty acid moiety from the compound of any of the formulae herein (e.g., any of the formulae, any formula in the tables herein), or salt, solvate, hydrate or prodrug thereof. A further aspect of the method is that comprising the intracellular release of a short chain fatty acid moiety containing 2 or more carbons from an appropriate carrier molecule.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragacanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *Echinacea*, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also be used in the pharmaceutical compositions herein.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, (e.g., 0.01 to 1 mg/kg effective dose) but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a disorder or disease herein. Another object of the present invention is the use of a compound as described herein (e.g., of any formulae herein) for use in the treatment of a disorder or disease herein.

Many compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Further, the aforementioned compounds also include their N-oxides. The term "N-oxides" refers to one or more nitrogen atoms, when present in a compound, are in N-oxide form, i.e., N→O.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

In another aspect the present invention relates to a mild and highly selective process for the in situ introduction of the O-, S- and N-nitrate group into compounds of any of the formulae herein.

DETAILED DESCRIPTION OF THE INVENTION

Technical Problem

NO, SCFA or PAM are difficult to use directly in Pharmaceutical compositions.

The use of NO donors is well known in medicine as a means to modulate blood pressure and inflammation[13]. Such NO donors exert their action, as aforementioned, largely in the extracellular environment. In the case of blood pressure regulators, release of NO in the blood results in effects on the endothelium which are desirable. In the case of modulators of inflammation, general release of NO may result in side effects such as loss of blood pressure which are undesirable.

Similarly, the SCFAs are volatile, malodorous and unstable. PAMs such as polyamines are similarly unattractive for direct use. While these products such as SCFAs or NO (inhaled gas) have been applied to the body, they are used in amounts that are undesirable. The technical problem to solve, was, therefore, to focus the release of these products (NO, SCFA, PAMs) to cells associated with inflammation, cancer or infection such that lower amounts could be used.

Solution to Problem

The compounds reported here are mostly located in intracellular compartments and thus may donate NO or SCFA or PAM to an intracellular receptor, preferably an intra-phagosomal or lysosomal receptor. Macrolide antibacterial compounds are well known for their ability to be concentrated in acidic compartments, notably the phagosomes of immune cells such as neutrophils and macrophage[14]. Phagosomes are the organs where bacteria and other debris are digested by the phagocytes using oxidative processes and digestive enzymes. Certain bacteria resist this process by reducing the capacity of the cell to produce antibacterial factors (lower pH, proteases, active oxygen species, antibacterial enzymes, NO).

If, however, a compound was also trapped in the phagosome that was capable of donating a stimulatory factor such as SCFA, PAM or NO, then there is the potential to overcome the inhibition due to the bacterium. More importantly, if the Phagocyte absorbs a compound able to donate SCFA, PAM or NO prior to that phagocyte encountering bacteria, it is potentially stimulated to better kill bacteria immediately on contact with them. This is potentially of significance in treating infections by bacteria such as *Legionella, Pasteurella, Listeria* and *Mycobacterium* species that are intracellular parasites. It is also potentially significant in the stimulation of barrier cells to resist the effect of bacteria, or to maintain physical barriers toward bacteria.

In addition to their roles in immunology, SCFA, NO and PAM have a role in homeostasis, acute inflammation and wound healing[15]. Phagocytes like macrophages are involved in many aspects of metabolism and are sensitive to SCFA, NO and PAM. The delivery of these substances preferentially to cells of this type is a means to allow them to respond to the stimulus of SCFA, PAM or NO without using high systemic levels. This is achieved by delivering the substances as conjugates to lysosomally tropic compounds (ALCs).

Thus the efficacy of molecules described herein in various models of inflammation and resolution of inflammation were examined. In these models, example compounds reported here were able to reduce the effects of inflammation, support body weight maintenance, and reduce disease signs without causing appreciable toxicity.

Definitions

"Anti-infective barrier" means the ability of epithelium to prevent the penetration of bacteria or other pathogens.

Stimulating the formation of an anti-infective barrier means increasing the ability of epithelium to prevent the penetration of bacteria or other pathogens through the up-regulation of tight junction formation or other barrier functions.

"Anti-infective response" means the ability of immune cells or similar to prevent the growth of bacteria or other pathogens via phagocytosis, oxidative burst or other toxic responses inactivating the pathogen.

Stimulating the formation of an anti-infective response means increasing the ability of immune cells or similar cells to prevent the growth of bacteria or other pathogens via phagocytosis, oxidative burst or other toxic responses inactivating the pathogen.

"ALC" means an Amphiphilic Lysosomally trapped Compound.

"PAM" means Product of Anaerobic Metabolism. PAMs include but are not limited to SCFA, NO, $H_2S$, mercaptans that eventually generate $H_2S/HS^-$ polyamines (e.g., compounds of Table 7), amino acid residues lacking the C-terminus (decarboxylated), bile acids (e.g., steroid acids found in the bile of mammals and other vertebrates, such as chenodeoxycholic acid, cholic acid, deoxycholic acid, lithocholic acid, and the like), or degradation products from polyphenol metabolism such as 3-(3-Hydroxyphenyl)propanoic (hMPP) acid, SCFA means Short Chain Fatty Acid, which is a fatty acid molecule having an aliphatic tail of eight or less carbon atoms.

"NO" means Nitric Oxide.

Advantageous Effects of Invention

The compounds reported here are useful in many respects. They are anti-microbial, anti-inflammatory, able to accumulate in tumors and donate NO and able to protect against inflammation of the intestine. Selected embodiments are able to modulate inflammation of the liver and protect against accumulation of fat or the resulting fibrosis.

The compounds are readily soluble as salts, may be provided by the oral route, or via other means. They are adequately stable for pharmacological use when stored at the appropriate pH conditions.

DESCRIPTION OF EMBODIMENTS

Figure 1:
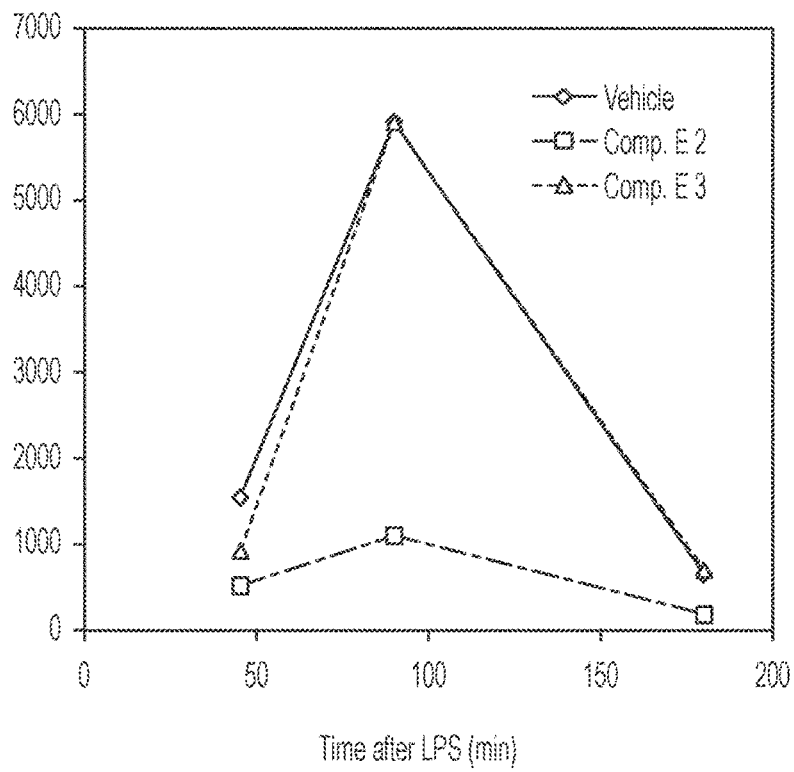
FIG. 1: TNFa—Production by LPS treated mice with either Vehicle (1% citric acid in water, 5 mL/kg) or 10 µmol/kg Compound E2 or Compound E3.

General Procedure for the Introduction of the Nitrooxide Group

The compound to be nitrated (1 equiv.) (—SH, —OH, —NH) is dissolved or suspended in acetic acid (approximately 6.0 ml per 1 mmol compound to be nitrated) and a solution of nitric acid (10% in acetic anhydride, about 3.25 ml per 1 mmol compound to be nitrated) is slowly added to the system while cooling in an ice bath. When TLC indicated complete consumption of starting materials the mixture is poured onto ice hydrolyzing any remains of acetic anhydride, followed by cautious neutralization of acid species with sodium bicarbonate. Extraction of the aqueous system with dichloromethane (3×), drying of combined organic phases over sodium sulfate and subsequent purification of crude products by column chromatography (acetone-cyclohexane 1:3→1:1) yields products as amorphous white foams.

The invention will be further described in the following intermediates and examples. It should be understood that these examples are for illustrative purposes only and are not to be construed as limiting this invention in any manner.

EXAMPLES

Unless otherwise specified, all commercially available reagents and solvents were used without prior purification. All chemical structures and names are generated from ChemDraw Ultra (Cambridge).

TABLE 1

Examples of ALC Core

| Entry | ALC Core | Structure |
|---|---|---|
| A-1 | Azithromycin ($R_1$ to $R_5$ = H, $R_6$ = $CH_3$) | 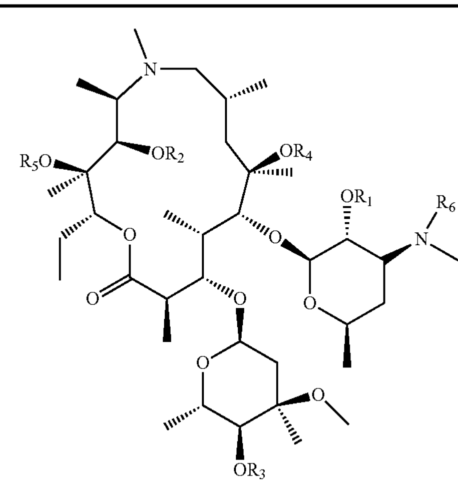 |

TABLE 1-continued

Examples of ALC Core

| Entry | ALC Core | Structure |
|---|---|---|
| A-2 | Erythromycin (X = OH) ($R_1$ to $R_5$ = H, $R_6$ = $CH_3$) or Erythromycin N-Oxime (X = N—OH) | 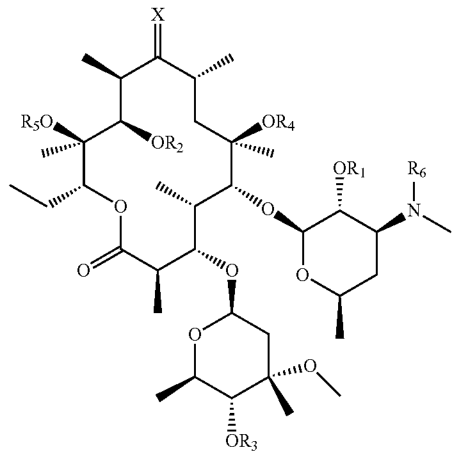 |
| A-3 | Hydroxychloroquine ($R_1$ = H, $R_2$ = $CH_3$) | 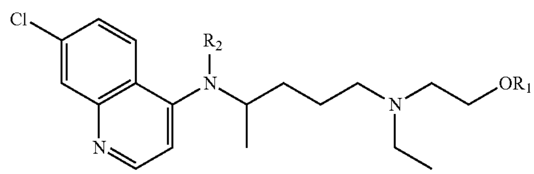 |
| A-4 | N-ethanol HCQ ($R_1$ = H, $R_2$ = H) | 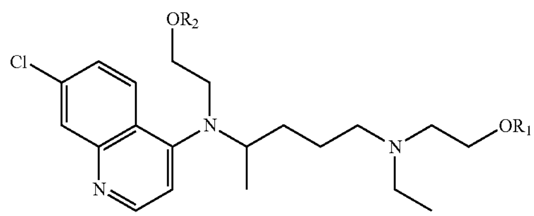 |
| A-5 | Propranolol ($R_1$ = H, $R_2$ = $CH_3$) | 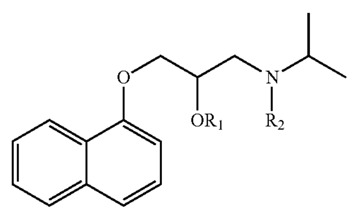 |
| A-6 | N-ethanol-propranolol ($R_1$ = H, $R_2$ = H) | 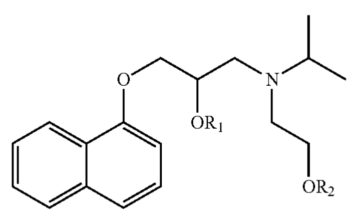 |
| A-7 | 4-hydroxypropranolol ($R_1$ = H, $R_2$ = H, $R_3$ = H) | 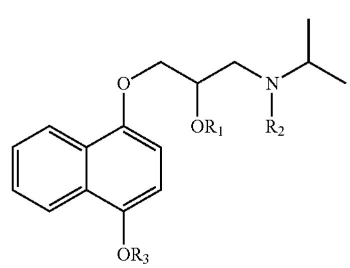 |

TABLE 1-continued

Examples of ALC Core

| Entry | ALC Core | Structure |
|---|---|---|
| A-8 | 2-(4-fluorophenyl)-3-amino-4-(3-[2,3-di{butyroyloxy}propyloxy]phenyl)-carbonylpyrazole ($R_1$ = H, $R_2$ = H) | 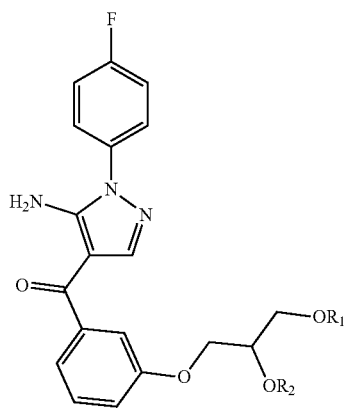 |
| A-9 | 2-(4-pyridyl)-3-amino-4-(3-[2,3-di{butyroyloxy}propyloxy]-phenyl)carbonylpyrazole ($R_1$ = H, $R_2$ = H) | 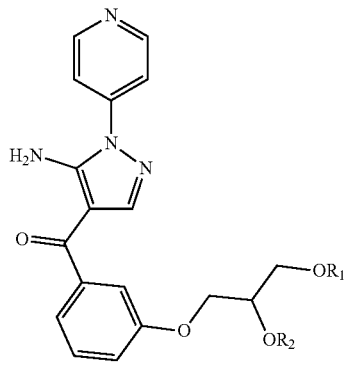 |
| A-10 | C5Y0073 ($R_1$ to $R_5$ = H, $R_6$ = $CH_3$) or 14-(4-Dimethylamino-3-hydroxy-6-methyl-tetrahydro-pyran-2-yloxy)-5-ethyl-1,6,7-trihydroxy-2,6,8,9,11,13,15-heptamethyl-4,16-dioxa-9-aza-bicyclo[11.2.1]hexadecan-3-one | 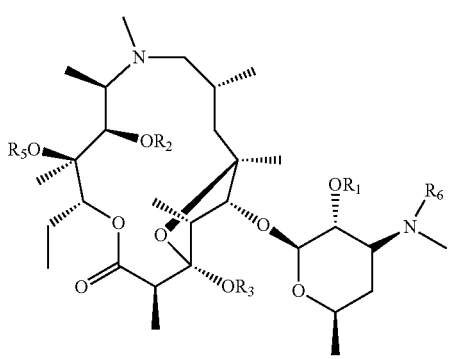 |

TABLE 1-continued

Examples of ALC Core

| Entry | ALC Core | Structure |
|---|---|---|
| A-11/ E-16 | CSY0041 ($R_1$ to $R_6$ = H) or 2-Ethyl-3,4,10-trihydroxy-13-(5-hydroxy-4-methoxy-4,6-dimethyl-tetrahydro-pyran-2-yloxy)-11-(3-hydroxy-6-methyl-4-methylamino-tetrahydro-pyran-2-yloxy)-3,5,6,8,10,12,14-heptamethyl-1-oxa-6-aza-cyclopentadecan-15-one | 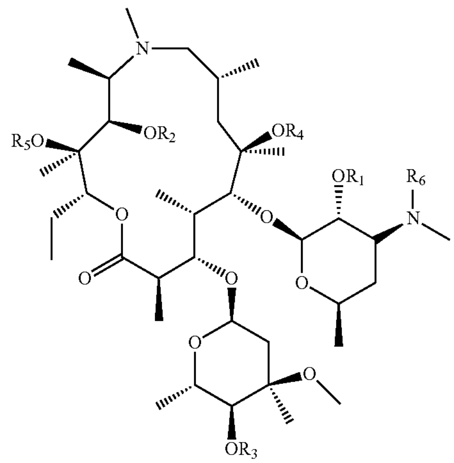 |
| A-12 | C5Y1239 ($R_1$ to $R_5$ = H) or 11-(4-Dimethylamino-3-hydroxy-6-methyl-tetrahydro-pyran-2-yloxy)-2-ethyl-3,4,10,13-tetrahydroxy-3,5,6,8,10,12,14-heptamethyl-1-oxa-6-aza-cyclopentadecan-15-one | 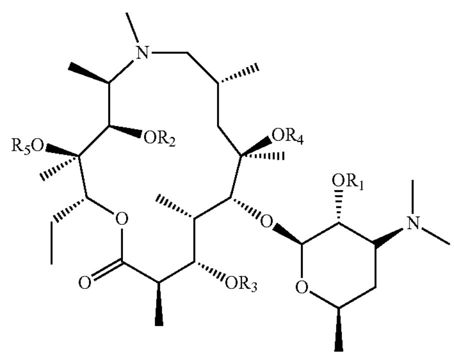 |
| A-13.1 | CSY1130 ($R_1$ to $R_6$ = H) (preparation see Example or 11-{4-[Bis-(2-hydroxy-ethyl)-amino]-3-hydroxy-6-methyl-tetrahydro-pyran-2-yloxy}-2-ethyl-3,4,10-trihydroxy-13-(5-hydroxy-4-methoxy-4,6-dimethyl-tetrahydro-pyran-2-yloxy)-3,5,6,8,10,12,14-heptamethyl-1-oxa-6-aza-cyclopentadecan-15-one | 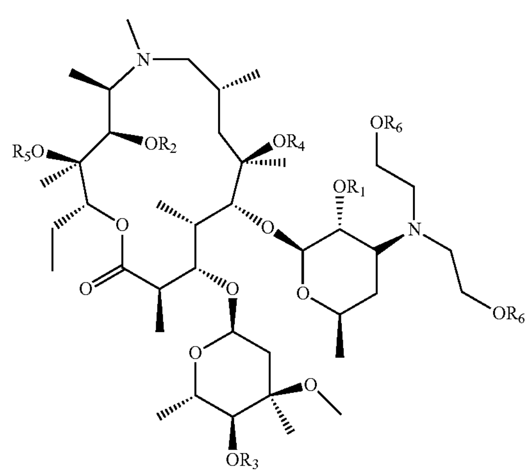 |

TABLE 1-continued

Examples of ALC Core

| Entry | ALC Core | Structure |
|---|---|---|
| A-13.2 | CSY5632 ($R_1$ to $R_6$ = H) or (2R,3S,4R,5R,8R,10R,11R,12S,13S,14R)-11-(((2S,3S,6R)-3-(bis(2-hydroxyethyl)amino)-4-hydroxy-6-methyltetrahydro-2H-pyran-2-yl)oxy)-2-ethyl-3,4,10-trihydroxy-13-(((2R,4R,5S,6S)-5-hydroxy-4-methoxy-4,6-dimethyltetrahydro-2H-pyran-2-yl)oxy)-3,5,6,8,10,12,14-heptamethyl-1-oxa-6-azacyclopentadecan-15-one | 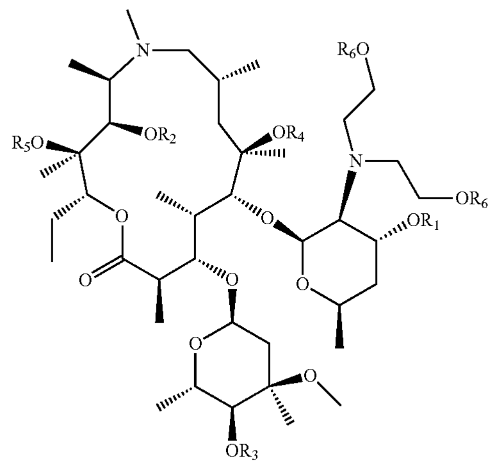 |
| A-14.1 | CSY2219 ($R_1$ to $R_5$ = H) or 2-Ethyl-3,4,10-trihydroxy-13-(5-hydroxy-4-methoxy-4,6-dimethyl-tetrahydro-pyran-2-yloxy)-11-(3-hydroxy-6-methyl-4-morpholin-4-yl-tetrahydro-pyran-2-yloxy)-3,5,6,8,10,12,14-heptamethyl-1-oxa-6-aza-cyclopentadecan-15-one | 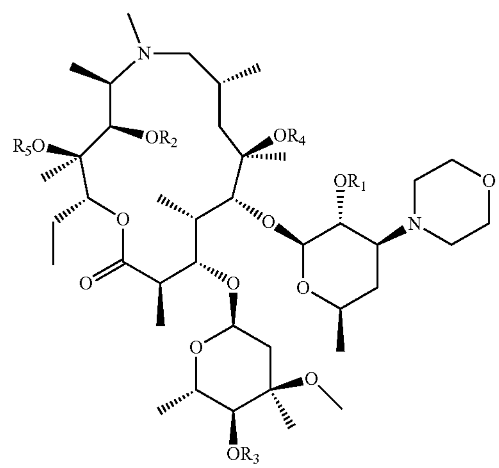 |
| A-14.2 | CSY5602 ($R_1$ to $R_5$ = H) or (2R,3S,4R,5R,8R,10R,11R,12S,13S,14R)-2-ethyl-3,4,10-trihydroxy-13-(((2R,4R,5S,6S)-5-hydroxy-4-methoxy-4,6-dimethyltetrahydro-2H-pyran-2-yl)oxy)-11-(((2S,3S,6R)-4-hydroxy-6-methyl-3-morpholinotetrahydro-2H-pyran-2-yl)oxy)-3,5,6,8,10,12,14-heptamethyl-1-oxa-6-azacyclopentadecan-15-one | 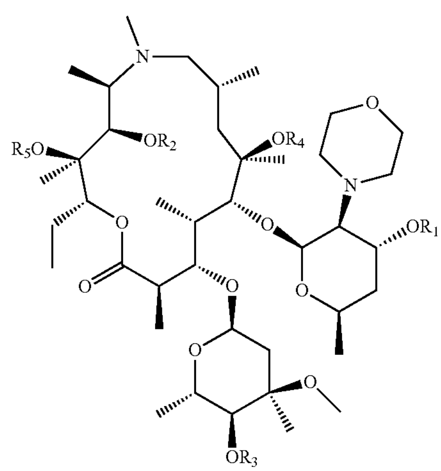 |

TABLE 1-continued

Examples of ALC Core

| Entry | ALC Core | Structure |
|---|---|---|
| A-15 | CSY1019 ($R_1$ to $R_5$ = H) or 11-(4-Dimethylamino-6-methyl-3-nitrooxy-tetrahydro-pyran-2-yloxy)-2-ethyl-3,4,10-trihydroxy-13-(5-hydroxy-4-methoxy-4,6-dimethyl-tetrahydro-pyran-2-yloxy)-3,5,6,8,10,12,14-heptamethyl-1-oxa-6-aza-cyclopentadecan-15-one | 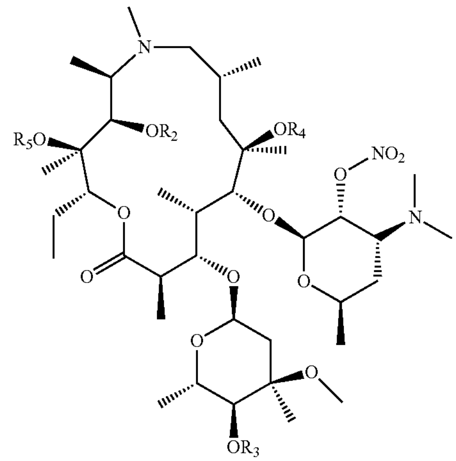 |
| A-16 | Tildipirosin ($R_1$ to $R_3$ = H) | 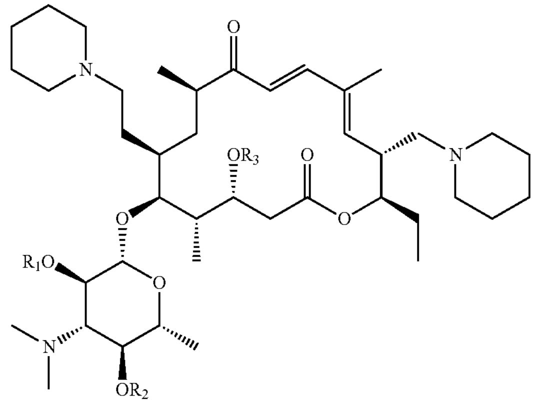 |
| A-17 | Gamithromycin ($R_1$ to $R_5$ = H) | 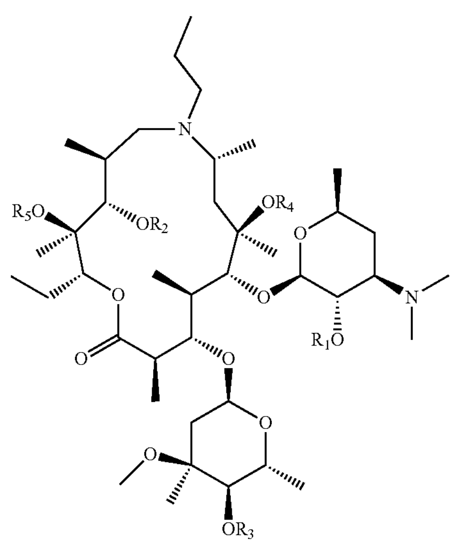 |

TABLE 1-continued

Examples of ALC Core

| Entry | ALC Core | Structure |
|---|---|---|
| A-18 | Tylosin ($R_1$ to $R_5$ = H) | 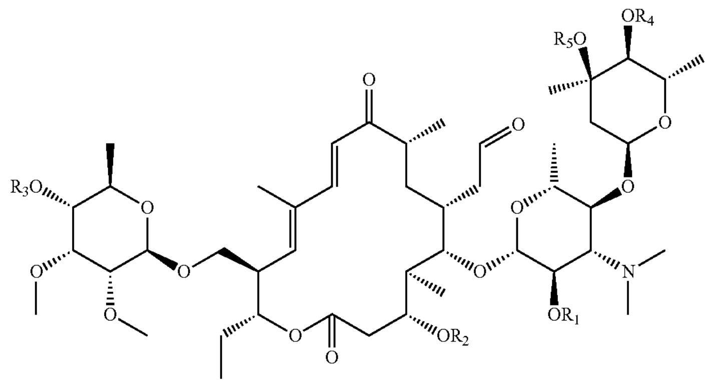 |
| A-19.1 | Polyamines ($R_1$ to $R_2$ = H) | Typical example but not limiting: |
| A-19.2 | Polyamines ($R_1$ to $R_4$ = H) | Typical example but not limiting: |
| A-19.3 | Polyamines ($R_1$ = $R_2$ = H; $R_3$ = alkyl, usually ethyl) | Typical example but not limiting: |
| A-20.1 | Tris(hydroxymethyl)nitromethane ($R_1$ to $R_3$ = H) | 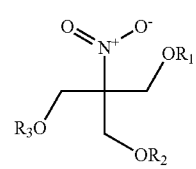 |
| A-20.2 | Sodium Tris(hydroxymethyl)aminopropylsulfonate ($R_1$ to $R_3$ = H) | 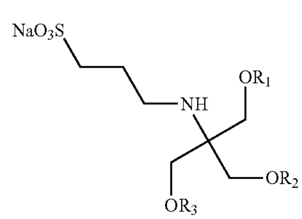 |

TABLE 1-continued

Examples of ALC Core

| Entry | ALC Core | Structure |
|---|---|---|
| A-21 | Clarithromycin ($R_1$ to $R_4$ = H) | 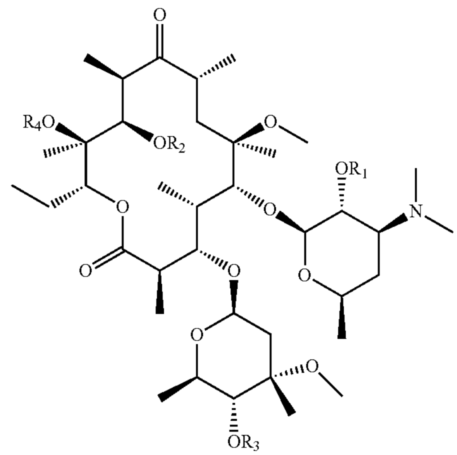 |
| A-22 | Tulathromycin ($R_1$ to $R_5$ = 0) | 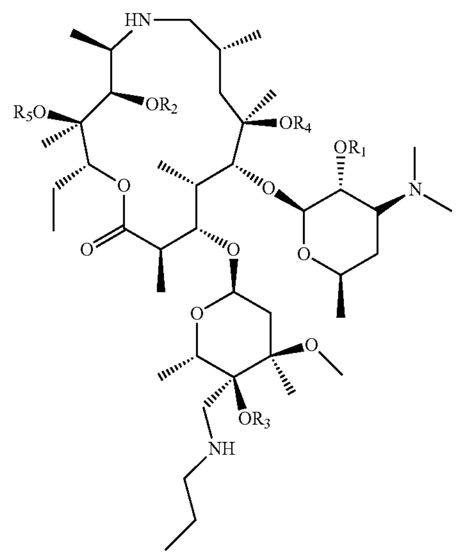 |

TABLE 2

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-1 | Azithromycin | $NO_2$ | H | H | H | H | $CH_3$ |
| E-2 | Azithromycin | $NO_2$ | Ac | H | H | H | $CH_3$ |
| E-3 | Azithromycin | $NO_2$ | H | H | H | H | C-10 alkyl |
| E-4 | Azithromycin | $NO_2$ | Ac | H | H | H | C-10 alkyl |
| E-5 | Azithromycin | $NO_2$ | Propionyl | H | H | H | $CH_3$ |
| E-6 | Azithromycin | p-Nitro benzoyl | $NO_2$ | $NO_2$ | H | H | $CH_3$ |
| E-7 | Azithromycin | Benzoyl | $NO_2$ | H | H | H | $CH_3$ |
| E-8 | Erythromycin oxime | $NO_2$ | Ac | H | H | H | $CH_3$ |
| E-9 | Azithromycin | Ac | $NO_2$ | H | H | H | $CH_3$ |
| E-10 | Azithromycin | H | $NO_2$ | H | H | H | $CH_3$ |
| E-11 | Azithromycin | $NO_2$ | $ch_3$ | H | H | H | $CH_3$ |
| E-12 | Azithromycin | H | Tetranitro moiety[1] | H | H | H | $CH_3$ |

TABLE 2-continued

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-13 | Azithromycin | $NO_2$ | Propionyl | H | H | Propionyl | $CH_3$ |
| E-14 | Azithromycin | H | H | H | H | H | Propanol-$NO_2$ |
| E-15 | Azithromycin | H | H | H | H | H | $CH_3$ |
| E-16 | Azithromycin | H | H | H | H | H | H |
| E-17/I-7 | Azithromycin | H | Ac | H | H | H | $CH_3$ |
| E-18 | Azithromycin | H | Propionyl | H | H | H | $CH_3$ |
| E-19 | Azithromycin | H | Butyryl | H | H | H | $CH_3$ |
| E-20/I-2 | Azithromycin | H | H | H | H | H | C-10 alkyl |
| E-21 | Azithromycin | $NO_2$ | $NO_2$ | H | H | H | $CH_3$ |
| E-22/I-4 | Azithromycin | Ac | $CH_2CCH$ | H | H | H | $CH_3$ |
| E-23/I-6 | Azithromycin | Ac | Ac | H | H | H | $CH_3$ |
| E-24 | Azithromycin | $NO_2$ | Butyryl | H | H | H | $CH_3$ |
| E-25//I-3 | Azithromycin | Ac | H | H | H | H | $CH_3$ |
| E-26/I-8 | Azithromycin | Benzoyl | H | H | H | H | $CH_3$ |
| E-27 | Azithromycin | Succinyl | H | H | H | H | $CH_3$ |
| E-28 | Azithromycin | Ac | Propionyl | H | H | H | $CH_3$ |
| E-29 | Azithromycin | Ac | Butyryl | H | H | H | $CH_3$ |
| E-30 | Azithromycin | Propionyl | H | H | H | H | $CH_3$ |
| E-31 | Azithromycin | Propionyl | $NO_2$ | H | H | H | $CH_3$ |
| E-32 | Azithromycin | Propionyl | Ac | H | H | H | $CH_3$ |
| E-33 | Azithromycin | Propionyl | Propionyl | H | H | H | $CH_3$ |
| E-34 | Azithromycin | Propionyl | Butyryl | H | H | H | $CH_3$ |
| E-35 | Azithromycin | Butyryl | H | H | H | H | $CH_3$ |
| E-36 | Azithromycin | Butyryl | $NO_2$ | H | H | H | $CH_3$ |
| E-37 | Azithromycin | Butyryl | Ac | H | H | H | $CH_3$ |
| E-38 | Azithromycin | Butyryl | Propionyl | H | H | H | $CH_3$ |
| E-39 | Azithromycin | Butyryl | Butyryl | H | H | H | $CH_3$ |
| E-40 | Azithromycin | H | Succinyl | H | H | H | $CH_3$ |
| E-41 | Azithromycin | H | Pyruvyl | H | H | H | $CH_3$ |
| E-42 | Azithromycin | H | Maleyl | H | H | H | $CH_3$ |
| E-43 | Azithromycin | H | Lactyl | H | H | H | $CH_3$ |
| E-44 | Azithromycin | H | Isobutyryl | H | H | H | $CH_3$ |
| E-45 | Azithromycin | H | Valeryl | H | H | H | $CH_3$ |
| E-46 | Azithromycin | H | Isovaleryl | H | H | H | $CH_3$ |
| E-47 | Azithromycin | Butyryl | Butyryl | Butyryl | Butyryl | H | $CH_3$ |
| E-48 | Azithromycin | Butyryl | Butyryl | Butyryl | H | H | $CH_3$ |
| E-49 | Azithromycin | Ac | Ac | Ac | Ac | H | $CH_3$ |
| E-50 | Azithromycin | Ac | Ac | Ac | H | H | $CH_3$ |
| E-51 | Azithromycin | Propionyl | Propionyl | Propionyl | Propionyl | H | $CH_3$ |
| E-52 | Azithromycin | Propionyl | Propionyl | Propionyl | H | H | $CH_3$ |
| E-53 | Azithromycin | Succinyl | Succinyl | Succinyl | Succinyl | H | $CH_3$ |
| E-54 | Azithromycin | Pyruvyl | Pyruvyl | Pyruvyl | Pyruvyl | H | $CH_3$ |
| E-55 | Azithromycin | Maleyl | Maleyl | Maleyl | Maleyl | H | $CH_3$ |
| E-56 | Azithromycin | Lactyl | Lactyl | Lactyl | Lactyl | H | $CH_3$ |
| E-57 | Azithromycin | Isobutyryl | Isobutyryl | Isobutyryl | Isobutyryl | H | $CH_3$ |
| E-58 | Azithromycin | Valeryl | Valeryl | Valeryl | Valeryl | H | $CH_3$ |
| E-59 | Azithromycin | Isovaleryl | Isovaleryl | Isovaleryl | Isovaleryl | H | $CH_3$ |
| E-60 | Azithromycin | Succinyl | Succinyl | Succinyl | H | H | $CH_3$ |
| E-61 | Azithromycin | Pyruvyl | Pyruvyl | Pyruvyl | H | H | $CH_3$ |
| E-62 | Azithromycin | Maleyl | Maleyl | Maleyl | H | H | $CH_3$ |
| E-63 | Azithromycin | Lactyl | Lactyl | Lactyl | H | H | $CH_3$ |
| E-64 | Azithromycin | Isobutyryl | Isobutyryl | Isobutyryl | H | H | $CH_3$ |
| E-65 | Azithromycin | Valeryl | Valeryl | Valeryl | H | H | $CH_3$ |
| E-66 | Azithromycin | Isovaleryl | Isovaleryl | Isovaleryl | H | H | $CH_3$ |
| E-67 | Azithromycin | Succinyl | Succinyl | H | H | H | $CH_3$ |
| E-68 | Azithromycin | Pyruvyl | Pyruvyl | H | H | H | $CH_3$ |
| E-69 | Azithromycin | Maleyl | Maleyl | H | H | H | $CH_3$ |
| E-70 | Azithromycin | Lactyl | Lactyl | H | H | H | $CH_3$ |
| E-71 | Azithromycin | Isobutyryl | Isobutyryl | H | H | H | $CH_3$ |
| E-72 | Azithromycin | Valeryl | Valeryl | H | H | H | $CH_3$ |
| E-73 | Azithromycin | Isovaleryl | Isovaleryl | H | H | H | $CH_3$ |
| E-74 | Azithromycin | Acetoxypropionyl | H | H | H | H | $CH_3$ |
| E-75 | Azithromycin | Lipoyl | Lipoyl | H | H | H | $CH_3$ |
| E-76 | Azithromycin | H | Lipoyl | H | H | H | $CH_3$ |
| E-77 | Azithromycin | Lipoyl | H | H | H | H | $CH_3$ |
| E-78 | Azithromycin | $NO_2$ | Lipoyl | H | H | H | $CH_3$ |
| E-79 | Azithromycin | $NO_2$ | Succinyl-dithiole-3-thione | H | H | H | $CH_3$ |
| E-80 | Azithromycin | Succinyl-dithiole-3-thione | H | H | H | H | $CH_3$ |

TABLE 2-continued

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-81 | Azithromycin | Polysulfide ethyl carbonate | H | H | H | H | $CH_3$ |
| E-82 | Azithromycin | NO-thioethylcarbonate | H | H | H | H | $CH_3$ |
| E-83 | Azithromycin | O-Phenyl chlorothionocarbonate | H | H | H | H | $CH_3$ |
| E-84 | Azithromycin | n-hexanoyl | H | H | H | H | $CH_3$ |
| E-85 | Azithromycin | Bromoethylcarbonate | H | H | H | H | $CH_3$ |
| E-86 | Azithromycin | Vinyll carbonate | H | H | H | H | $CH_3$ |
| E-87 | Hydroxychloroquine | Ac | H | | | | |
| E-88 | Hydroxychloroquine | Propionyl | H | | | | |
| E-89 | Hydroxychloroquine | Butyryl | H | | | | |
| E-90 | Hydroxychloroquine | Succinyl | H | | | | |
| E-91 | Hydroxychloroquine | Pyruvyl | H | | | | |
| E-92 | Hydroxychloroquine | Maleyl | H | | | | |
| E-93 | Hydroxychloroquine | Lactyl | H | | | | |
| E-94 | Hydroxychloroquine | Isobutyryl | H | | | | |
| E-95 | Hydroxychloroquine | Valeryl | H | | | | |
| E-96 | Hydroxychloroquine | Isovaleryl | H | | | | |
| E-97 | Hydroxychloroquine | Lipoyl | H | | | | |
| E-98 | Hydroxychloroquine | Ac | CH3 | | | | |
| E-99 | Hydroxychloroquine | Propionyl | CH3 | | | | |
| E-100 | Hydroxychloroquine | Butyryl | CH3 | | | | |
| E-101 | Hydroxychloroquine | Succinyl | CH3 | | | | |
| E-102 | Hydroxychloroquine | Pyruvyl | CH3 | | | | |
| E-103 | Hydroxychloroquine | Maleyl | CH3 | | | | |
| E-104 | Hydroxychloroquine | Lactyl | CH3 | | | | |
| E-105 | Hydroxychloroquine | Isobutyryl | CH3 | | | | |
| E-106 | Hydroxychloroquine | Valeryl | CH3 | | | | |
| E-107 | Hydroxychloroquine | Isovaleryl | CH3 | | | | |
| E-108 | Hydroxychloroquine | Lipoyl | CH3 | | | | |
| E-109 | N-ethanol HCQ | NO2 | Ac | | | | |
| E-110 | N-ethanol HCQ | NO2 | Propionyl | | | | |
| E-111 | N-ethanol HCQ | NO2 | Butyryl | | | | |
| E-112 | N-ethanol HCQ | NO2 | Succinyl | | | | |
| E-113 | N-ethanol HCQ | NO2 | Pyruvyl | | | | |
| E-114 | N-ethanol HCQ | NO2 | Maleyl | | | | |
| E-115 | N-ethanol HCQ | NO2 | Lactyl | | | | |
| E-116 | N-ethanol HCQ | NO2 | Isobutyryl | | | | |
| E-117 | N-ethanol HCQ | NO2 | Valeryl | | | | |
| E-118 | N-ethanol HCQ | NO2 | Isovaleryl | | | | |
| E-119 | N-ethanol HCQ | NO2 | Lipoyl | | | | |
| E-120 | N-ethanol HCQ | Ac | NO2 | | | | |
| E-121 | N-ethanol HCQ | Propionyl | NO2 | | | | |
| E-122 | N-ethanol HCQ | Butyryl | NO2 | | | | |
| E-123 | N-ethanol HCQ | Succinyl | NO2 | | | | |
| E-124 | N-ethanol HCQ | Pyruvyl | NO2 | | | | |
| E-125 | N-ethanol HCQ | Maleyl | NO2 | | | | |
| E-126 | N-ethanol HCQ | Lactyl | NO2 | | | | |
| E-127 | N-ethanol HCQ | Isobutyryl | NO2 | | | | |
| E-128 | N-ethanol HCQ | Valeryl | NO2 | | | | |
| E-129 | N-ethanol HCQ | Isovaleryl | NO2 | | | | |
| E-130 | N-ethanol HCQ | Lipoyl | NO2 | | | | |
| E-131 | Propranolol | Ac | H | | | | |
| E-132 | Propranolol | Propionyl | H | | | | |
| E-133 | Propranolol | Butyryl | H | | | | |
| E-134 | Propranolol | Succinyl | H | | | | |
| E-135 | Propranolol | Pyruvyl | H | | | | |
| E-136 | Propranolol | Maleyl | H | | | | |
| E-137 | Propranolol | Lactyl | H | | | | |
| E-138 | Propranolol | Isobutyryl | H | | | | |
| E-139 | Propranolol | Valeryl | H | | | | |
| E-140 | Propranolol | Isovaleryl | H | | | | |
| E-141 | Propranolol | Lipoyl | H | | | | |
| E-142 | Propranolol | 2-O-Nitrolactyl | H | | | | |
| E-143 | Propranolol | Ac | CH3 | | | | |
| E-144 | Propranolol | Propionyl | CH3 | | | | |
| E-145 | Propranolol | Butyryl | CH3 | | | | |
| E-146 | Propranolol | Succinyl | CH3 | | | | |
| E-147 | Propranolol | Pyruvyl | CH3 | | | | |

TABLE 2-continued

Examples of compounds showing the appropriate substituents.
Compound formulae based on "ALC core" structures as detailed in Table 1 (above).

| Compound Entry | ALC Core | R₁ | R₂ | R₃ | R₄ | R₅ | R₆ |
|---|---|---|---|---|---|---|---|
| E-148 | Propranolol | Maleyl | CH3 | | | | |
| E-149 | Propranolol | Lactyl | CH3 | | | | |
| E-150 | Propranolol | Isobutyryl | CH3 | | | | |
| E-151 | Propranolol | Valeryl | CH3 | | | | |
| E-152 | Propranolol | Isovaleryl | CH3 | | | | |
| E-153 | Propranolol | Lipoyl | CH3 | | | | |
| E-154 | N-ethanol-propranolol | NO2 | Ac | | | | |
| E-155 | N-ethanol-propranolol | NO2 | Propionyl | | | | |
| E-156 | N-ethanol-propranolol | NO2 | Butyryl | | | | |
| E-157 | N-ethanol-propranolol | NO2 | Succinyl | | | | |
| E-158 | N-ethanol-propranolol | NO2 | Pyruvyl | | | | |
| E-159 | N-ethanol-propranolol | NO2 | Maleyl | | | | |
| E-160 | N-ethanol-propranolol | NO2 | Lactyl | | | | |
| E-161 | N-ethanol-propranolol | NO2 | Isobutyryl | | | | |
| E-162 | N-ethanol-propranolol | NO2 | Valeryl | | | | |
| E-163 | N-ethanol-propranolol | NO2 | Isovaleryl | | | | |
| E-164 | N-ethanol-propranolol | NO2 | Lipoyl | | | | |
| E-165 | N-ethanol-propranolol | Propionyl | NO2 | | | | |
| E-166 | N-ethanol-propranolol | Butyryl | NO2 | | | | |
| E-167 | N-ethanol-propranolol | Succinyl | NO2 | | | | |
| E-168 | N-ethanol-propranolol | Pyruvyl | NO2 | | | | |
| E-169 | N-ethanol-propranolol | Maleyl | NO2 | | | | |
| E-170 | N-ethanol-propranolol | Lactyl | NO2 | | | | |
| E-171 | N-ethanol-propranolol | Isobutyryl | NO2 | | | | |
| E-172 | N-ethanol-propranolol | Valeryl | NO2 | | | | |
| E-173 | N-ethanol-propranolol | Isovaleryl | NO2 | | | | |
| E-174 | N-ethanol-propranolol | Lipoyl | NO2 | | | | |
| E-175 | 4-hydroxy propranolol | NO2 | H | Ac | | | |
| E-176 | 4-hydroxy propranolol | NO2 | H | Propionyl | | | |
| E-177 | 4-hydroxy propranolol | NO2 | H | Butyryl | | | |
| E-178 | 4-hydroxy propranolol | NO2 | H | Succinyl | | | |
| E-179 | 4-hydroxy propranolol | NO2 | H | Pyruvyl | | | |
| E-180 | 4-hydroxy propranolol | NO2 | H | Maleyl | | | |
| E-181 | 4-hydroxy propranolol | NO2 | H | Lactyl | | | |
| E-182 | 4-hydroxy propranolol | NO2 | H | Isobutyryl | | | |
| E-183 | 4-hydroxy propranolol | NO2 | H | Valeryl | | | |
| E-184 | 4-hydroxy propranolol | NO2 | H | Isovaleryl | | | |
| E-185 | 4-hydroxy propranolol | NO2 | H | Lipoyl | | | |
| E-186 | 4-hydroxy propranolol | NO2 | CH3 | Ac | | | |
| E-187 | 4-hydroxy propranolol | NO2 | CH3 | Propionyl | | | |

TABLE 2-continued

Examples of compounds showing the appropriate substituents.
Compound formulae based on "ALC core" structures as detailed in Table 1 (above).

| Compound Entry | ALC Core | R$_1$ | R$_2$ | R$_3$ | R$_4$ | R$_5$ | R$_6$ |
|---|---|---|---|---|---|---|---|
| E-188 | 4-hydroxy propranolol | NO2 | CH3 | Butyryl | | | |
| E-189 | 4-hydroxy propranolol | NO2 | CH3 | Succinyl | | | |
| E-190 | 4-hydroxy propranolol | NO2 | CH3 | Pyruvyl | | | |
| E-191 | 4-hydroxy propranolol | NO2 | CH3 | Maleyl | | | |
| E-192 | 4-hydroxy propranolol | NO2 | CH3 | Lactyl | | | |
| E-193 | 4-hydroxy propranolol | NO2 | CH3 | Isobutyryl | | | |
| E-194 | 4-hydroxy propranolol | NO2 | CH3 | Valeryl | | | |
| E-195 | 4-hydroxy propranolol | NO2 | CH3 | Isovaleryl | | | |
| E-196 | 4-hydroxy propranolol | NO2 | CH3 | Lipoyl | | | |
| E-197 | A-8 | Ac | Ac | | | | |
| E-198 | A-8 | Propionyl | Propionyl | | | | |
| E-199 | A-8 | Butyryl | Butyryl | | | | |
| E-200 | A-8 | Succinyl | Succinyl | | | | |
| E-201 | A-8 | Pyruvyl | Pyruvyl | | | | |
| E-202 | A-8 | Maleyl | Maleyl | | | | |
| E-203 | A-8 | Lactyl | Lactyl | | | | |
| E-204 | A-8 | Isobutyryl | Isobutyryl | | | | |
| E-205 | A-8 | Valeryl | Valeryl | | | | |
| E-206 | A-8 | Isovaleryl | Isovaleryl | | | | |
| E-207 | A-8 | Lipoyl | Lipoyl | | | | |
| E-208 | A-9 | Ac | Ac | | | | |
| E-209 | A-9 | Propionyl | Propionyl | | | | |
| E-210 | A-9 | Butyryl | Butyryl | | | | |
| E-211 | A-9 | Succinyl | Succinyl | | | | |
| E-212 | A-9 | Pyruvyl | Pyruvyl | | | | |
| E-213 | A-9 | Maleyl | Maleyl | | | | |
| E-214 | A-9 | Lactyl | Lactyl | | | | |
| E-215 | A-9 | Isobutyryl | Isobutyryl | | | | |
| E-216 | A-9 | Valeryl | Valeryl | | | | |
| E-217 | A-9 | Isovaleryl | Isovaleryl | | | | |
| E-218 | A-9 | Lipoyl | Lipoyl | | | | |
| E-219 | A-10 | H | Tetranitro moiety1 | | H | H | CH3 |
| E-220 | A-10 | H | H | | H | H | Propanol-NO2 |
| E-221 | A-10 | H | H | | H | H | CH3 |
| E-222 | A-10 | H | H | | H | H | H |
| E-223 | A-10 | H | Ac | | H | H | CH3 |
| E-224 | A-10 | H | Propionyl | | H | H | CH3 |
| E-225 | A-10 | H | Butyryl | | H | H | CH3 |
| E-226 | A-10 | H | H | | H | H | C-10 alkyl |
| E-227 | A-10 | Ac | CH2CCH | | H | H | CH3 |
| E-228 | A-10 | Ac | Ac | | H | H | CH3 |
| E-229 | A-10 | Ac | H | | H | H | CH3 |
| E-230 | A-10 | Benzoyl | H | | H | H | CH3 |
| E-231 | A-10 | Succinyl | H | | H | H | CH3 |
| E-232 | A-10 | Ac | Propionyl | | H | H | CH3 |
| E-233 | A-10 | Ac | Butyryl | | H | H | CH3 |
| E-234 | A-10 | Propionyl | H | | H | H | CH3 |
| E-235 | A-10 | Propionyl | Ac | | H | H | CH3 |
| E-236 | A-10 | Propionyl | Propionyl | | H | H | CH3 |
| E-237 | A-10 | Propionyl | Butyryl | | H | H | CH3 |
| E-238 | A-10 | Butyryl | H | | H | H | CH3 |
| E-239 | A-10 | Butyryl | Ac | | H | H | CH3 |
| E-240 | A-10 | Butyryl | Propionyl | | H | H | CH3 |
| E-241 | A-10 | Butyryl | Butyryl | | H | H | CH3 |
| E-242 | A-10 | H | Succinyl | | H | H | CH3 |
| E-243 | A-10 | H | Pyruvyl | | H | H | CH3 |
| E-244 | A-10 | H | Maleyl | | H | H | CH3 |
| E-245 | A-10 | H | Lactyl | | H | H | CH3 |
| E-246 | A-10 | H | Isobutyryl | | H | H | CH3 |
| E-247 | A-10 | H | Valeryl | | H | H | CH3 |
| E-248 | A-10 | H | Isovaleryl | | H | H | CH3 |
| E-249 | A-10 | Butyryl | Butyryl | | Butyryl | H | CH3 |
| E-250 | A-10 | Butyryl | Butyryl | | H | H | CH3 |

TABLE 2-continued

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-251 | A-10 | Ac | Ac |  | Ac | H | CH3 |
| E-252 | A-10 | Ac | Ac |  | H | H | CH3 |
| E-253 | A-10 | Propionyl | Propionyl |  | Propionyl | H | CH3 |
| E-254 | A-10 | Propionyl | Propionyl |  | H | H | CH3 |
| E-255 | A-11/E-16 | Butyric | H | H | H | H | Butyric |
| E-256 | A-11/E-16 | Butyric | Butyric | H | H | H | Butyric |
| E-257 | A-11/E-16 | Butyric | Butyric | Butyric | H | H | Butyric |
| E-258 | A-11/E-16 | H | H | H | H | H | Mannose |
| E-259 | A-11/E-16 | Propionic | H | H | H | H | Propionic |
| E-260 | A-11/E-16 | Propionic | Propionic | H | H | H | Propionic |
| E-261 | A-11/E-16 | Propionic | Propionic | Propionic | H | H | Propionic |
| E-262 | A-11/E-16 | Ac | H | H | H | H | Ac |
| E-263 | A-11/E-16 | Ac | Ac | H | H | H | Ac |
| E-264 | A-11/E-16 | Ac | Ac | Ac | H | H | Ac |
| E-265 | A-12 | NO2 | H | H | H | H |  |
| E-266 | A-12 | Ac | Ac | H | H | H |  |
| E-267 | A-12 | Ac | Ac | Ac | H | H |  |
| E-268 | A-12 | Ac | Ac | Ac | Ac | H |  |
| E-269 | A-12 | Propionic | Propionic | H | H | H |  |
| E-270 | A-12 | Propionic | Propionic | Propionic | H | H |  |
| E-271 | A-12 | Propionic | Propionic | Propionic | Propionic | H |  |
| E-272 | A-12 | Butyric | Butyric | H | H | H |  |
| E-273 | A-12 | Butyric | Butyric | Butyric | H | H |  |
| E-274 | A-12 | Butyric | Butyric | Butyric | Butyric | H |  |
| E-275 | A-12 | Succinic | Succinic | H | H | H |  |
| E-276 | A-12 | Pyruvic | Pyruvic | H | H | H |  |
| E-277 | A-12 | Maleic | Maleic | H | H | H |  |
| E-278 | A-12 | Lactic | Lactic | H | H | H |  |
| E-279 | A-12 | Isobutyric | Isobutyric | H | H | H |  |
| E-280 | A-12 | Isobutyric | Isobutyric | Isobutyric | H | H |  |
| E-281 | A-12 | Isobutyric | Isobutyric | Isobutyric | Isobutyric | H |  |
| E-282 | A-12 | Valeric | Valeric | H | H | H |  |
| E-283 | A-12 | Valeric | Valeric | Valeric | H | H |  |
| E-284 | A-12 | Valeric | Valeric | Valeric | Valeric | H |  |
| E-285 | A-12 | Isovaleric | Isovaleric | H | H | H |  |
| E-286 | A-12 | Isovaleric | Isovaleric | Isovaleric | H | H |  |
| E-287 | A-12 | Isovaleric | Isovaleric | Isovaleric | Isovaleric | H |  |
| E-288 | A-12 | Lipoic | Lipoic | H | H | H |  |
| E-289 | A-12 | Lipoic | Lipoic | Lipoic | H | H |  |
| E-290 | A-12 | Lipoic | Lipoic | Lipoic | Lipoic | H |  |
| E-291 | A-13.1 | H | H | H | H | H | Ac |
| E-292 | A-13.1 | Ac | H | H | H | H | Ac |
| E-293 | A-13.1 | Ac | Ac | H | H | H | Ac |
| E-294 | A-13.1 | Ac | Ac | Ac | H | H | Ac |
| E-295 | A-13.1 | H | H | H | H | H | Propionic |
| E-296 | A-13.1 | Propionic | H | H | H | H | Propionic |
| E-297 | A-13.1 | Propionic | Propionic | H | H | H | Propionic |
| E-298 | A-13.1 | Propionic | Propionic | Propionic | H | H | Propionic |
| E-299 | A-13.1 | H | H | H | H | H | Butyric |
| E-300 | A-13.1 | Butyric | H | H | H | H | Butyric |
| E-301 | A-13.1 | Butyric | Butyric | H | H | H | Butyric |
| E-302 | A-13.1 | Butyric | Butyric | Butyric | H | H | Butyric |
| E-303 | A-13.1 | H | H | H | H | H | Succinic |
| E-304 | A-13.1 | H | H | H | H | H | Pyruvic |
| E-305 | A-13.1 | H | H | H | H | H | Maleic |
| E-306 | A-13.1 | H | H | H | H | H | Lactic |
| E-307 | A-13.1 | H | H | H | H | H | Isobutyric |
| E-308 | A-13.1 | Isobutyric | H | H | H | H | Isobutyric |
| E-309 | A-13.1 | Isobutyric | Isobutyric | H | H | H | Isobutyric |
| E-310 | A-13.1 | Isobutyric | Isobutyric | Isobutyric | H | H | Isobutyric |
| E-311 | A-13.1 | H | H | H | H | H | Valeric |
| E-312 | A-13.1 | Valeric | H | H | H | H | Valeric |
| E-313 | A-13.1 | Valeric | Valeric | H | H | H | Valeric |
| E-314 | A-13.1 | Valeric | Valeric | Valeric | H | H | Valeric |
| E-315 | A-13.1 | H | H | H | H | H | Isovaleric |
| E-316 | A-13.1 | Isovaleric | H | H | H | H | Isovaleric |
| E-317 | A-13.1 | Isovaleric | Isovaleric | H | H | H | Isovaleric |
| E-318 | A-13.1 | Isovaleric | Isovaleric | Isovaleric | H | H | Isovaleric |
| E-319 | A-13.1 | H | H | H | H | H | Lipoic |
| E-320 | A-13.1 | Lipoic | H | H | H | H | Lipoic |
| E-321 | A-13.1 | Lipoic | Lipoic | H | H | H | Lipoic |
| E-322 | A-13.1 | Lipoic | Lipoic | Lipoic | H | H | Lipoic |
| E-323 | A-13.2 | H | H | H | H | H | Ac |
| E-324 | A-13.2 | Ac | H | H | H | H | Ac |

TABLE 2-continued

Examples of compounds showing the appropriate substituents.
Compound formulae based on "ALC core" structures as detailed in Table 1 (above).

| Compound Entry | ALC Core | R$_1$ | R$_2$ | R$_3$ | R$_4$ | R$_5$ | R$_6$ |
|---|---|---|---|---|---|---|---|
| E-325 | A-13.2 | Ac | Ac | H | H | H | Ac |
| E-326 | A-13.2 | Ac | Ac | Ac | H | H | Ac |
| E-327 | A-13.2 | H | H | H | H | H | Propionic |
| E-328 | A-13.2 | Propionic | H | H | H | H | Propionic |
| E-329 | A-13.2 | Propionic | Propionic | H | H | H | Propionic |
| E-330 | A-13.2 | Propionic | Propionic | Propionic | H | H | Propionic |
| E-331 | A-13.2 | H | H | H | H | H | Butyric |
| E-332 | A-13.2 | Butyric | H | H | H | H | Butyric |
| E-333 | A-13.2 | Butyric | Butyric | H | H | H | Butyric |
| E-334 | A-13.2 | Butyric | Butyric | Butyric | H | H | Butyric |
| E-335 | A-13.2 | H | H | H | H | H | Succinic |
| E-336 | A-13.2 | H | H | H | H | H | Pyruvic |
| E-337 | A-13.2 | H | H | H | H | H | Maleic |
| E-338 | A-13.2 | H | H | H | H | H | Lactic |
| E-339 | A-13.2 | H | H | H | H | H | Isobutyric |
| E-340 | A-13.2 | Isobutyric | H | H | H | H | Isobutyric |
| E-341 | A-13.2 | Isobutyric | Isobutyric | H | H | H | Isobutyric |
| E-342 | A-13.2 | Isobutyric | Isobutyric | Isobutyric | H | H | Isobutyric |
| E-343 | A-13.2 | H | H | H | H | H | Valeric |
| E-344 | A-13.2 | Valeric | H | H | H | H | Valeric |
| E-345 | A-13.2 | Valeric | Valeric | H | H | H | Valeric |
| E-346 | A-13.2 | Valeric | Valeric | Valeric | H | H | Valeric |
| E-347 | A-13.2 | H | H | H | H | H | Isovaleric |
| E-348 | A-13.2 | Isovaleric | H | H | H | H | Isovaleric |
| E-349 | A-13.2 | Isovaleric | Isovaleric | H | H | H | Isovaleric |
| E-350 | A-13.2 | Isovaleric | Isovaleric | Isovaleric | H | H | Isovaleric |
| E-351 | A-13.2 | H | H | H | H | H | Lipoic |
| E-352 | A-13.2 | Lipoic | H | H | H | H | Lipoic |
| E-353 | A-13.2 | Lipoic | Lipoic | H | H | H | Lipoic |
| E-354 | A-13.2 | Lipoic | Lipoic | Lipoic | H | H | Lipoic |
| E-355 | A-14.1 | Ac | H | H | H | H | |
| E-356 | A-14.1 | Ac | Ac | H | H | H | |
| E-357 | A-14.1 | Ac | Ac | Ac | H | H | |
| E-358 | A-14.1 | Propionic | H | H | H | H | |
| E-359 | A-14.1 | Propionic | Propionic | H | H | H | |
| E-360 | A-14.1 | Propionic | Propionic | Propionic | H | H | |
| E-361 | A-14.1 | Butyric | H | H | H | H | |
| E-362 | A-14.1 | Butyric | Butyric | H | H | H | |
| E-363 | A-14.1 | Butyric | Butyric | Butyric | H | H | |
| E-364 | A-14.1 | Succinic | H | H | H | H | |
| E-365 | A-14.1 | Pyruvic | H | H | H | H | |
| E-366 | A-14.1 | Maleic | H | H | H | H | |
| E-367 | A-14.1 | Lactic | H | H | H | H | |
| E-368 | A-14.1 | Isobutyric | H | H | H | H | |
| E-369 | A-14.1 | Isobutyric | Isobutyric | H | H | H | |
| E-370 | A-14.1 | Isobutyric | Isobutyric | Isobutyric | H | H | |
| E-371 | A-14.1 | Valeric | H | H | H | H | |
| E-372 | A-14.1 | Valeric | Valeric | H | H | H | |
| E-373 | A-14.1 | Valeric | Valeric | Valeric | H | H | |
| E-374 | A-14.1 | Isovaleric | H | H | H | H | |
| E-375 | A-14.1 | Isovaleric | Isovaleric | H | H | H | |
| E-376 | A-14.1 | Isovaleric | Isovaleric | Isovaleric | H | H | |
| E-377 | A-14.1 | Lipoic | H | H | H | H | |
| E-378 | A-14.1 | Lipoic | Lipoic | H | H | H | |
| E-379 | A-14.1 | Lipoic | Lipoic | Lipoic | H | H | |
| E-380 | A-14.2 | Ac | H | H | H | H | |
| E-381 | A-14.2 | Ac | Ac | H | H | H | |
| E-382 | A-14.2 | Ac | Ac | Ac | H | H | |
| E-383 | A-14.2 | Propionic | H | H | H | H | |
| E-384 | A-14.2 | Propionic | Propionic | H | H | H | |
| E-385 | A-14.2 | Propionic | Propionic | Propionic | H | H | |
| E-386 | A-14.2 | Butyric | H | H | H | H | |
| E-387 | A-14.2 | Butyric | Butyric | H | H | H | |
| E-388 | A-14.2 | Butyric | Butyric | Butyric | H | H | |
| E-389 | A-14.2 | Succinic | H | H | H | H | |
| E-390 | A-14.2 | Pyruvic | H | H | H | H | |
| E-391 | A-14.2 | Maleic | H | H | H | H | |
| E-392 | A-14.2 | Lactic | H | H | H | H | |
| E-393 | A-14.2 | Isobutyric | H | H | H | H | |
| E-394 | A-14.2 | Isobutyric | Isobutyric | H | H | H | |
| E-395 | A-14.2 | Isobutyric | Isobutyric | Isobutyric | H | H | |
| E-396 | A-14.2 | Valeric | H | H | H | H | |
| E-397 | A-14.2 | Valeric | Valeric | H | H | H | |
| E-398 | A-14.2 | Valeric | Valeric | Valeric | H | H | |

TABLE 2-continued

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-399 | A-14.2 | Isovaleric | H | H | H | H | |
| E-400 | A-14.2 | Isovaleric | Isovaleric | H | H | H | |
| E-401 | A-14.2 | Isovaleric | Isovaleric | Isovaleric | H | H | |
| E-402 | A-14.2 | Lipoic | H | H | H | H | |
| E-403 | A-14.2 | Lipoic | Lipoic | H | H | H | |
| E-404 | A-14.2 | Lipoic | Lipoic | Lipoic | H | H | |
| E-405 | A-15 | | Succinic | H | H | H | |
| E-406 | A-15 | | Pyruvic | H | H | H | |
| E-407 | A-15 | | Maleic | H | H | H | |
| E-408 | A-15 | | Lactic | H | H | H | |
| E-409 | A-15 | | Isobutyric | H | H | H | |
| E-410 | A-15 | | Isobutyric | Isobutyric | H | H | |
| E-411 | A-15 | | Valeric | H | H | H | |
| E-412 | A-15 | | Valeric | Valeric | H | H | |
| E-413 | A-15 | | Isovaleric | H | H | H | |
| E-414 | A-15 | | Isovaleric | Isovaleric | H | H | |
| E-415 | A-15 | | Lipoic | Lipoic | H | H | |
| E-416 | A-16 | Ac | H | H | | | |
| E-417 | A-16 | Ac | Ac | H | | | |
| E-418 | A-16 | Ac | Ac | Ac | | | |
| E-419 | A-16 | Propionic | H | H | | | |
| E-420 | A-16 | Propionic | Propionic | H | | | |
| E-421 | A-16 | Propionic | Propionic | Propionic | | | |
| E-422 | A-16 | Butyric | H | H | | | |
| E-423 | A-16 | Butyric | Butyric | H | | | |
| E-424 | A-16 | Butyric | Butyric | Butyric | | | |
| E-425 | A-16 | Isobutyric | H | H | | | |
| E-426 | A-16 | Isobutyric | Isobutyric | H | | | |
| E-427 | A-16 | Isobutyric | Isobutyric | Isobutyric | | | |
| E-428 | A-16 | Valeric | H | H | | | |
| E-429 | A-16 | Valeric | Valeric | H | | | |
| E-430 | A-16 | Valeric | Valeric | Valeric | | | |
| E-431 | A-16 | Isovaleric | H | H | | | |
| E-432 | A-16 | Isovaleric | Isovaleric | H | | | |
| E-433 | A-16 | Isovaleric | Isovaleric | Isovaleric | | | |
| E-434 | A-16 | Lipoic | H | H | | | |
| E-435 | A-16 | Lipoic | Lipoic | H | | | |
| E-436 | A-16 | Lipoic | Lipoic | Lipoic | | | |
| E-437 | A-16 | Hexanoic | H | H | | | |
| E-438 | A-16 | Hexanoic | Hexanoic | H | | | |
| E-439 | A-16 | Hexanoic | Hexanoic | Hexanoic | | | |
| E-440 | A-16 | Heptanoic | H | H | | | |
| E-441 | A-16 | Heptanoic | Heptanoic | H | | | |
| E-442 | A-16 | Heptanoic | Heptanoic | Heptanoic | | | |
| E-443 | A-16 | Octanoic | H | H | | | |
| E-444 | A-16 | Octanoic | Octanoic | H | | | |
| E-445 | A-16 | Octanoic | Octanoic | Octanoic | | | |
| E-446 | A-16 | Decanoic | H | H | | | |
| E-447 | A-16 | Decanoic | Decanoic | H | | | |
| E-448 | A-16 | Decanoic | Decanoic | Decanoic | | | |
| E-449 | A-16 | Dodecanoic | H | H | | | |
| E-450 | A-16 | Dodecanoic | Dodecanoic | H | | | |
| E-451 | A-16 | Dodecanoic | Dodecanoic | Dodecanoic | | | |
| E-452 | A-17 | Ac | H | H | H | H | |
| E-453 | A-17 | Ac | Ac | H | H | H | |
| E-454 | A-17 | Ac | Ac | Ac | H | H | |
| E-455 | A-17 | Propionic | H | H | H | H | |
| E-456 | A-17 | Propionic | Propionic | H | H | H | |
| E-457 | A-17 | Propionic | Propionic | Propionic | H | H | |
| E-458 | A-17 | Butyric | H | H | H | H | |
| E-459 | A-17 | Butyric | Butyric | H | H | H | |
| E-460 | A-17 | Butyric | Butyric | Butyric | H | H | |
| E-461 | A-17 | Isobutyric | H | H | H | H | |
| E-462 | A-17 | Isobutyric | Isobutyric | H | H | H | |
| E-463 | A-17 | Isobutyric | Isobutyric | Isobutyric | H | H | |
| E-464 | A-17 | Valeric | H | H | H | H | |
| E-465 | A-17 | Valeric | Valeric | H | H | H | |
| E-466 | A-17 | Valeric | Valeric | Valeric | H | H | |
| E-467 | A-17 | Isovaleric | H | H | H | H | |
| E-468 | A-17 | Isovaleric | Isovaleric | H | H | H | |
| E-469 | A-17 | Isovaleric | Isovaleric | Isovaleric | H | H | |
| E-470 | A-17 | Lipoic | H | H | H | H | |
| E-471 | A-17 | Lipoic | Lipoic | H | H | H | |
| E-472 | A-17 | Lipoic | Lipoic | Lipoic | H | H | |

TABLE 2-continued

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-473 | A-17 | Hexanoic | H | H | H | H | |
| E-474 | A-17 | Hexanoic | Hexanoic | H | H | H | |
| E-475 | A-17 | Hexanoic | Hexanoic | Hexanoic | H | H | |
| E-476 | A-17 | Heptanoic | H | H | H | H | |
| E-477 | A-17 | Heptanoic | Heptanoic | H | H | H | |
| E-478 | A-17 | Heptanoic | Heptanoic | Heptanoic | H | H | |
| E-479 | A-17 | Octanoic | H | H | H | H | |
| E-480 | A-17 | Octanoic | Octanoic | H | H | H | |
| E-481 | A-17 | Octanoic | Octanoic | Octanoic | H | H | |
| E-482 | A-17 | Decanoic | H | H | H | H | |
| E-483 | A-17 | Decanoic | Decanoic | H | H | H | |
| E-484 | A-17 | Decanoic | Decanoic | Decanoic | H | H | |
| E-485 | A-17 | Dodecanoic | H | H | H | H | |
| E-486 | A-17 | Dodecanoic | Dodecanoic | H | H | H | |
| E-487 | A-17 | Dodecanoic | Dodecanoic | Dodecanoic | H | H | |
| E-488 | A-18 | Ac | H | H | H | H | |
| E-489 | A-18 | Ac | Ac | H | H | H | |
| E-490 | A-18 | Ac | Ac | Ac | H | H | |
| E-491 | A-18 | Propionic | H | H | H | H | |
| E-492 | A-18 | Propionic | Propionic | H | H | H | |
| E-493 | A-18 | Propionic | Propionic | Propionic | H | H | |
| E-494 | A-18 | Butyric | H | H | H | H | |
| E-495 | A-18 | Butyric | Butyric | H | H | H | |
| E-496 | A-18 | Butyric | Butyric | Butyric | H | H | |
| E-497 | A-18 | Isobutyric | H | H | H | H | |
| E-498 | A-18 | Isobutyric | Isobutyric | H | H | H | |
| E-499 | A-18 | Isobutyric | Isobutyric | Isobutyric | H | H | |
| E-500 | A-18 | Valeric | H | H | H | H | |
| E-501 | A-18 | Valeric | Valeric | H | H | H | |
| E-502 | A-18 | Valeric | Valeric | Valeric | H | H | |
| E-503 | A-18 | Isovaleric | H | H | H | H | |
| E-504 | A-18 | Isovaleric | Isovaleric | H | H | H | |
| E-505 | A-18 | Isovaleric | Isovaleric | Isovaleric | H | H | |
| E-506 | A-18 | Lipoic | H | H | H | H | |
| E-507 | A-18 | Lipoic | Lipoic | H | H | H | |
| E-508 | A-18 | Lipoic | Lipoic | Lipoic | H | H | |
| E-509 | A-18 | Hexanoic | H | H | H | H | |
| E-510 | A-18 | Hexanoic | Hexanoic | H | H | H | |
| E-511 | A-18 | Hexanoic | Hexanoic | Hexanoic | H | H | |
| E-512 | A-18 | Heptanoic | H | H | H | H | |
| E-513 | A-18 | Heptanoic | Heptanoic | H | H | H | |
| E-514 | A-18 | Heptanoic | Heptanoic | Heptanoic | H | H | |
| E-515 | A-18 | Octanoic | H | H | H | H | |
| E-516 | A-18 | Octanoic | Octanoic | H | H | H | |
| E-517 | A-18 | Octanoic | Octanoic | Octanoic | H | H | |
| E-518 | A-18 | Decanoic | H | H | H | H | |
| E-519 | A-18 | Decanoic | Decanoic | H | H | H | |
| E-520 | A-18 | Decanoic | Decanoic | Decanoic | H | H | |
| E-521 | A-18 | Dodecanoic | H | H | H | H | |
| E-522 | A-18 | Dodecanoic | Dodecanoic | H | H | H | |
| E-523 | A-18 | Dodecanoic | Dodecanoic | Dodecanoic | H | H | |
| E-524 | A-19.1 | Ac | Ac | | | | |
| E-525 | A-19.1 | Propionic | Propionic | | | | |
| E-526 | A-19.1 | Butyric | Butyric | | | | |
| E-527 | A-19.1 | Isobutyric | Isobutyric | | | | |
| E-528 | A-19.1 | Valeric | Valeric | | | | |
| E-529 | A-19.1 | Isovaleric | Isovaleric | | | | |
| E-530 | A-19.1 | Adamantylcarboxyl | Adamantylcarboxyl | | | | |
| E-531 | A-19.2 | Ac | Ac | Ac | Ac | | |
| E-532 | A-19.2 | Propionic | Propionic | Propionic | Propionic | | |
| E-533 | A-19.2 | Butyric | Butyric | Butyric | Butyric | | |
| E-534 | A-19.2 | Isobutyric | Isobutyric | Isobutyric | Isobutyric | | |
| E-535 | A-19.2 | Valeric | Valeric | Valeric | Valeric | | |
| E-536 | A-19.2 | Isovaleric | Isovaleric | Isovaleric | Isovaleric | | |
| E-537 | A-20.1 | Butyric | Butyric | Butyric | | | |
| E-538 | A-20.1 | Ac | Ac | Ac | | | |
| E-539 | A-20.1 | Propionic | Propionic | Propionic | | | |
| E-540 | A-1 | N-Phenyl chlorothionoformate | H | H | H | H | CH3 |
| E-541 | A-1 | Imiquimod-Succinate | H | H | H | H | CH3 |
| E-542 | A-1 | Resiquimod-Succinate | H | H | H | H | CH3 |

TABLE 2-continued

Examples of compounds showing the appropriate substituents.
Compound formulae based on "ALC core" structures as detailed in Table 1 (above).

| Compound Entry | ALC Core | $R_1$ | $R_2$ | $R_3$ | $R_4$ | $R_5$ | $R_6$ |
|---|---|---|---|---|---|---|---|
| E-543 | A-1 | Succinate-ethyl ester | H | H | H | H | CH3 |
| E-544 | A-1 | Indole-3-propionic | H | H | H | H | CH3 |
| E-545 | A-1 | Cyclopropanecarboxylic | H | H | H | H | CH3 |
| E-546 | A-1 | Cyclobutanecarboxylic | H | H | H | H | CH3 |
| E-547 | A-1 | Nicotinic | H | H | H | H | CH3 |
| E-548 | A-1 | Chenodeoxycholic | H | H | H | H | CH3 |
| E-549 | A-1 | Ferrocenylacetic | H | H | H | H | CH3 |
| E-550 | A-1 | Lipoic-S derivatives | H | H | H | H | CH3 |
| E-551 | A-1 | Methoxyacetic | H | H | H | H | CH3 |
| E-552 | C2 (see Table 16) | Butyric | Butyric | | | | |
| E-553 | A-1 | H | Butyric | Butyric | H | H | CH3 |
| E-554 | A-1 | H | Ac | Ac | H | H | CH3 |
| E-555 | A-1 | H | Propionic | Propionic | H | H | CH3 |
| E-556 | A-1 | O-Acetyl Lactic | | H | H | H | CH3 |
| E-557 | A-2 (X = O) | Isovaleric | H | H | H | H | CH3 |
| E-558 | A-2 (X = O) | Valeric | H | H | H | H | CH3 |
| E-559 | A-1 | Methoxyacetic | Methoxyacetic | Methoxyacetic | Methoxyacetic | H | CH3 |
| E-560 | A-1 | Cyclobutanecarboxylic | Cyclobutanecarboxylic | H | H | H | CH3 |
| E-561 | A-1 | Cyclobutanecarboxylic | Cyclobutanecarboxylic | Cyclobutanecarboxylic | H | H | CH3 |
| E-562 | A-1 | Nicotinic | Nicotinic | H | H | H | CH3 |
| E-563 | A-1 | Nicotinic | Nicotinic | Nicotinic | H | H | CH3 |
| E-564 | A-2 (X = O) | Ac | H | H | H | H | CH3 |
| E-566 | A-10 | Isobutyric | Isobutyric | Isobutyric | | H | CH3 |
| E-567 | A-10 | Isobutyric | Isobutyric | H | | H | CH3 |
| E-568 | A-10 | Isobutyric | H | H | | H | CH3 |
| E-569 | A-10 | Valeric | Valeric | Valeric | | H | CH3 |
| E-570 | A-10 | Valeric | Valeric | H | | H | CH3 |
| E-571 | A-10 | Valeric | H | H | | H | CH3 |
| E-572 | A-10 | Isovaleric | Isovaleric | Isovaleric | | H | CH3 |
| E-573 | A-10 | Isovaleric | Isovaleric | H | | H | CH3 |
| E-574 | A-10 | Isovaleric | H | H | | H | CH3 |
| E-575 | A-11/E-16 | Butyric | H | H | H | Butyric | Butyric |
| E-576 | A-19.1 | Ac | H | | | | |
| E-577 | A-19.1 | Propionic | H | | | | |
| E-578 | A-19.1 | Butyric | H | | | | |
| E-579 | A-20.2 | Butyric | Butyric | Butyric | | | |
| E-580 | A-20.2 | Ac | Ac | Ac | | | |
| E-581 | A-20.2 | Propionic | Propionic | Propionic | | | |
| E-582 | A-12 | Valeric | H | H | H | H | |
| E-583 | A-12 | Isovaleric | H | H | H | H | |
| E-584 | A-19.3 | Valeric | H | H | | | |
| E-585 | A-19.3 | Valeric | H | Ethyl | | | |
| E-586 | A-19.3 | Valeric | Valeric | H | | | |
| E-587 | A-19.3 | Valeric | Valeric | Ethyl | | | |
| E-588 | A-19.3 | Isovaleric | H | H | | | |
| E-589 | A-19.3 | Isovaleric | H | Ethyl | | | |
| E-590 | A-19.3 | Isovaleric | Isovaleric | H | | | |
| E-591 | A-19.3 | Isovaleric | Isovaleric | Ethyl | | | |
| E-592 | A-19.3 | Butyric | H | H | | | |
| E-593 | A-19.3 | Butyric | H | Ethyl | | | |
| E-594 | A-19.3 | Butyric | Butyric | H | | | |
| E-595 | A-19.3 | Butyric | Butyric | Ethyl | | | |
| E-596 | A-17 | NO2 | H | H | H | H | |
| E-597 | A-17 | NO2 | NO2 | H | H | H | |
| E-598 | A-18 | H | H | NO2 | H | H | |
| E-599 | A-18 | H | NO2 | NO2 | H | H | |
| E-600 | A-11/E-16 | H | H | no cladinose ring | H | H | Mannose |
| E-601 | A-21 | NO2 | | | | | |
| E-602 | A-21 | NO2 | NO2 | | | | |
| E-603 | A-21 | NO2 | NO2 | H | NO2 | | |

Procedures

Example 1

Synthesis of E-1: Typical Nitration Procedure

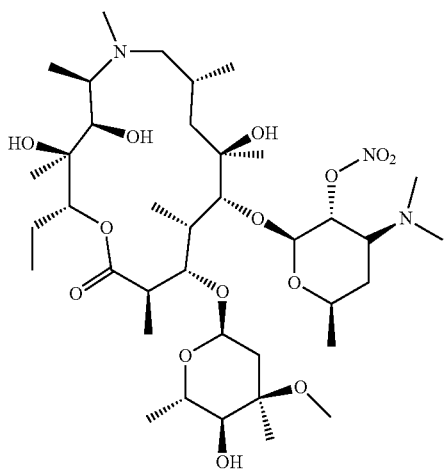

Method 1.

Acetic acid (40 mL) and Azithromycin (5 g, 6.73 mmol) were charged in a round bottom flask. Initially, the reaction solidified which eventually during stirring, produced a homogenous solution. The resulting solution was cooled in an ice-bath. Acetic anhydride (19.8 mL, 209.5 mmol) was taken up in another reaction flask and cooled in an ice bath. To this was added dropwise, nitric acid (2.2 mL, 46.43 mmol). After complete addition, the mixture was transferred to a dropping funnel and attached to the first reaction vessel containing the macrolide. The $HNO_3$—$Ac_2O$ mixture was slowly added to the reaction (ca. 1 drop per second). After complete addition, the reaction was allowed to warm to room temperature where it was stirred until reaction completion (3 h). The reaction was poured onto a stirred 200 mL ice-water. Stirring was continued until the ice is completely melted. The resulting aqueous solution was neutralized at first with a saturated solution of $NaHCO_3$, followed by pure solid $NaHCO_3$ to pH 8 to 9. The aqueous solution was extracted with DCM (5×). The DCM extracts were dried ($Na_2SO_4$), evaporated in vacuo. The crude product was purified by column chromatography (3:1 cyclohexane, ethyl acetate, 1% triethylamine) to get compound E-1 as a white foam (30% yield).

These nitration conditions can be applied to other ALCs, and in cases where there is more than one reactive hydroxy species, selective protection is necessary.

Method 2.

Hydroxyalkyl species (1 mmol) was suspended in acetonitrile in a round bottom flask while stirring (magnetic stir bar, 300 rpm). Silver nitrate (2 eq. per hydroxyl group) was added and the mixture was cooled in an ice bath. Phosgene (solution in toluene, 1 eq. per hydroxyl group) was carefully added dropwise. Immediate precipitation of silver chloride and formation of carbon dioxide indicated formation of nitro donor (caution: too quick $CO_2$ formation may result in strong foaming. Do not seal the flask!). After a couple of minutes a yellow color was obtained and stirring was continued for 15 minutes. When ESI-MS indicated satisfying turn-over rate of starting materials the reaction was quenched by addition of methanol, converting excess nitro donor to volatile methyl nitrate. The system was diluted by addition of DCM and was subject to extraction with saturated sodium bicarbonate solution (3×). Separation of organic phase, drying over sodium sulfate and evaporation of any volatiles in vacuo yielded the product as colorless oil or beige to off-white foam.

TABLE 3

Nitration Examples

| Compound Entry | Synthesis Method | ALC | Degree of Substitution | Yield | MS |
| --- | --- | --- | --- | --- | --- |
| E-596 | 2 | A-17 | Mono nitro | n.d.* | 822, M + H⁺ |
| E-597 | 2 | A-17 | Di nitro | n.d.* | 867, M + H⁺ |
|  | 2 | A-18 | Oxidation | n.d.* | 954, M + Na⁺ |
| E-598 | 2 | A-18 | Mono nitro | n.d.* | 999, M + Na⁺ |
| E-599 | 2 | A-18 | Di nitro | n.d.* | 1045, M + Na⁺ |
| E-601 | 2 | A-21 | Mono nitro | n.d.* | 793, M + H⁺ |
| E-602 | 2 | A-21 | Di nitro | n.d.* | 838, M + H⁺ |
| E-603 | 2 | A-21 | Tri nitro | n.d.* | 883, M + H⁺ | n.d.* not determined

Example 2

Synthesis of E-2

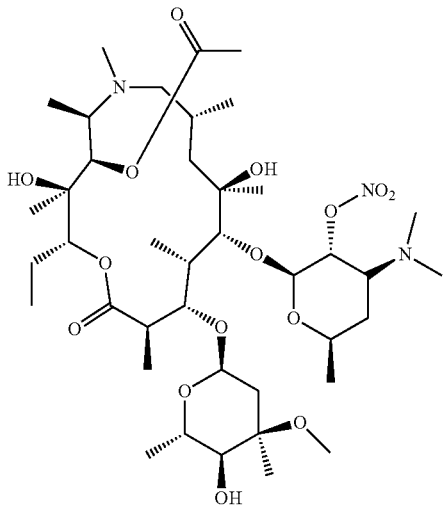

Compound E-1 (791 mg, 1.0 mmol) was taken up in 15 mL dichloromethane. Pyridine (89 mL, 1.1 mmol) was added and the resulting solution was cooled in an ice bath for approximately 10 minutes. At this point, a solution of acetic anhydride (113 ml, 1.2 mmol) in dichloromethane (15 mL) was added dropwise. The reaction was stirred continually at this temperature and then progressively warmed to room temperature where it was stirred overnight. The reaction was washed with a saturated solution of ammonium chloride (3×), water (3×) and dried over anhydrous $Na_2SO_4$. The solvent was evaporated in vacuo. Co-evaporation with toluene is necessary to remove residual pyridine from the system. This was followed by re-dissolving the residue in DCM and solvent evaporation twice to produce a white foam, which was dried under high-vacuum to produce E-2 (631 mg, 76%).

Example 3

Synthesis of E-3

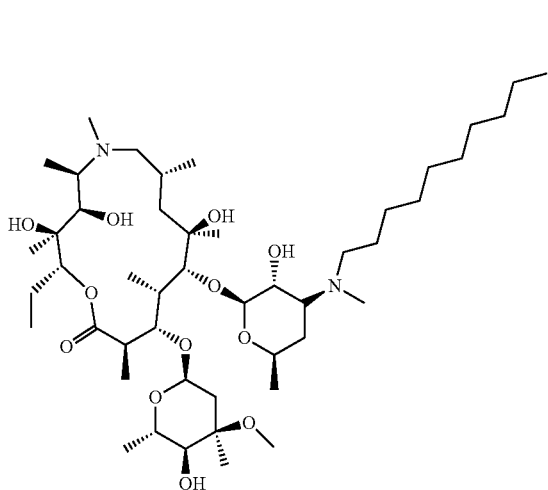

E-3 was synthesized using standard nitration procedure described above starting from E-20.

Example 4

Synthesis of E-4

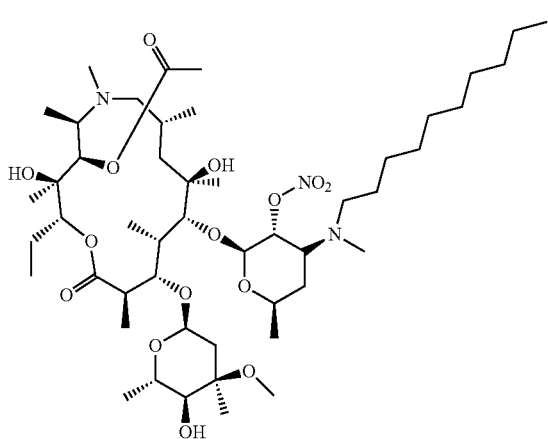

A solution of E-3 (1 mmol) and pyridine (1 mmol) in DCM (10 ml) was treated with acetic anhydride (1.5 mmol) at ambient temperature. Stirring was continued until TLC (acetone-cyclohexane 1:3) indicated complete consumption of the starting materials. The system was extracted with an aqueous solution of NH4Cl (2×10 ml) and water (3×10 ml). After drying over $Na_2SO_4$ all volatile components were evaporated in vacuo, traces of pyridine species were removed by co-evaporation with toluene (2×). The product E-4 was a colorless oil (41%).

Example 5

Synthesis of E-5

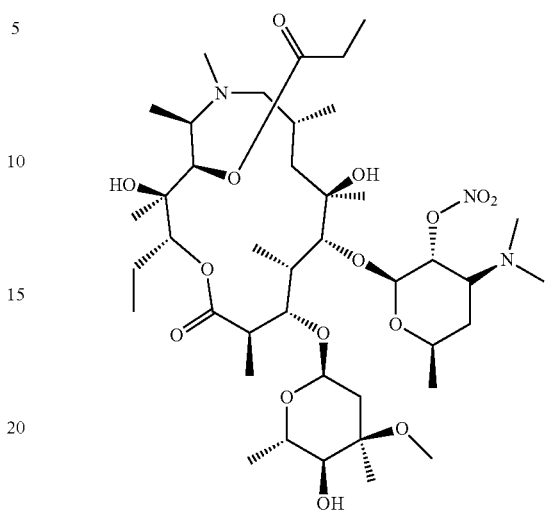

Method 1.

A solution of propionic acid (1.2 mmol) in 1,2-dichloroethane was treated with 1-Ethyl-3-(3-dimethyl-aminopropyl)carbodiimid (1.2 mmol) in the presence of a catalytical amount of DMAP for 30 min. at ambient temperature. Temperature was raised to 55° C., E-1 (1 mmol) was added and stirring was continued until TLC (acetone-cyclohexane 1:3) indicated complete consumption of the starting materials. The system was extracted with water (3×10 ml). After drying over $Na_2SO_4$ all volatile components were evaporated in vacuo, traces of pyridine species were removed by co-evaporation with toluene (2×). The crude products were purified by column chromatography (acetone-cyclohexane 1:3), yielding the product E-5 as white amorphous foam (39%).

Alternative Synthesis:

Compound E-1 (310 mg, 0.39 mmol) was taken up in dichloromethane (15 mL). At which point, pyridine (32 mL, 0.39 mmol) was added. The solution was stirred for 5 minutes, at which time, propionyl anhydride (51 mL, 0.40 mmol) was added. The reaction was allowed to stir at room temperature for 72 h. An additional propionyl anhydride (0.1 eq) was added and the reaction monitored until complete disappearance of starting material was observed (MS, reaction may take up to 1 week). The reaction was washed successively with a saturated aqueous solution of NH4Cl (3×) and $H_2O$ (3×). The organic phase was dried over anhydrous $Na_2SO_4$ and evaporated in vacuo. Co-evaporation with toluene is necessary to remove residual pyridine from the system. This was followed by re-dissolving the residue in DCM and solvent evaporation twice to produce E-5 as a white foam (210 mg, 64%).

Method 3:

A-1 (300 mg, 0.40 mmol), was dissolved in DCM (10 mL); to this solution was added TEA (279 µL, 5 eq) and propionylchloride (175 µL, 5 eq) subsequently and the mixture was stirred overnight at room temperature. Additional TEA (112 µL, 2 eq) and propionyl chloride (70 µL, 2 eq) were added and again mixture was stirred overnight at room temperature. Once more additional TEA (112 µL, 2 eq) and propionyl chloride (70 µL, 2 eq) were added and stirring at room temperature was continued overnight. TEA (344 µL, 9 eq) and propionyl chloride (314 µL, 9 eq) were added and the mixture was stirred at room temperature for 5 days. The reaction mixture was washed with aqueous $Na_2CO_3$-solution (3×, 10%) and water (3×), dried, concentrated to dryness, and dried at the oil pump. ESI-MS (positive) showed tri- and tetra-propionylation.

Method 4.

Propionic acid (4 eq) was taken up in 5 mL dichloromethane (DCM). Compound A-16 (0.5 mmol) and 4-dimethylaminopyridine (DMAP) (4.4 eq) were added and the resulting solution was cooled in an ice bath for approximately 10 minutes. At this point, dicyclohexylcarbodiimide (DCC) (4.4 eq) was added slowly. The reaction was stirred continually at this temperature for 5 minutes and then progressively warmed to room temperature where it was stirred overnight. Dicyclohexylurea (DCU) that was formed during the reaction is filtered off and discarded. The filtrate was collected and then washed with a saturated solution of sodium hydrogencarbonate (3×), water (1×) and dried over anhydrous $Na_2SO_4$. The solvent was evaporated in vacuo. This was followed by re-dissolving the residue in a small volume of methanol. The solution was transported dropwise into ice-cold water (2× volume of methanol) and stored in the freezer overnight. The precipitated product was filtered off and dried under high-vacuum to produce

TABLE 4

Propionylation Examples

| Compound Entry | Synthesis Method | ALC | Substituent equivalent | Reaction Condition (i.e. Workup) | Degree of Substitution | Yield | MS m/z ([M + H]+) |
|---|---|---|---|---|---|---|---|
| E-5 | 1 | A-1 | 1.1 | as described above | 1 | 64% | 850.3 |
| E-18 | See example 21 | A-1 | N/A | | 1 | 80% | 805.5 |
| E-419 | 4 | A-16 | 4 | | 1 | 50% | 791.3 |
| E-420 | | | | | 2 | (based on | 847.1 |
| E-421 | | | | | 3 | tri-ester | 903.0 |
| E-52 | 3 | A-1 | 18 | | 3 | Not | 917.9 |
| E-51 | | | | | 4 | determined | 973.8 |

Example 6

Synthesis of E-8

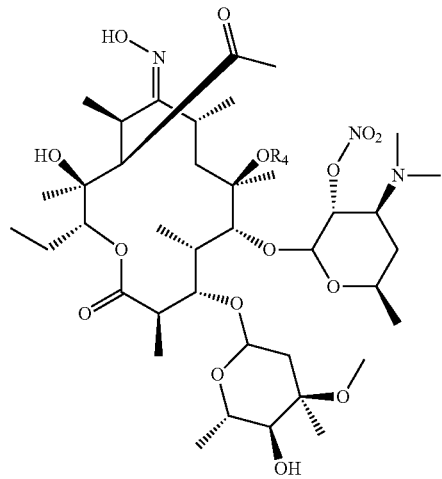

Erythromycin oxime was nitrated as described in the general procedure, followed by subsequent acetylation of crude nitration product with acetic anhydride in DCM with pyridine as catalyst. Column chromatography (acetone-cyclohexane 1:3) furnished the product E-8 as white amorphous foam (39%, two steps).

Example 7

Synthesis of E-10

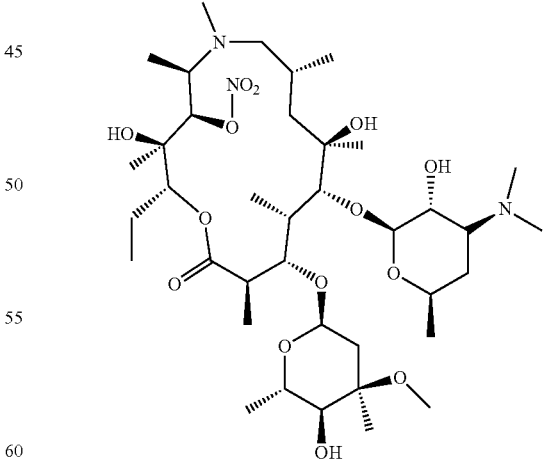

A solution of E-9 (1 mmol) in MeOH (20 ml) was vigorously stirred at 50° C. until TLC (acetone-cyclohexane 1:3) indicated complete deacetylation of the starting materials. Volatile components were removed in vacuo, the product E-10 was obtained as white amorphous foam (81%).

Example 8

Synthesis of E-11

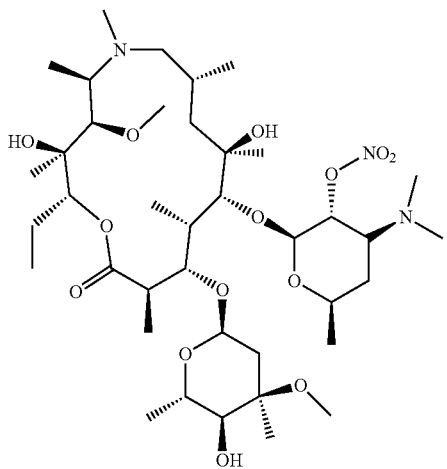

Azithromycin was nitrated as described above. After desired mono-nitration MeOH was added to the reaction mixture and stirring was continued for one further hour. Thus in situ generated methyl nitrate acted as methylating agent transferring one methyl group to 11-O-position of the macrolide at ambient temperature. Standard aqueous workup with subsequent purification by column chromatography (acetone-cyclohexane 1:3) delivered methylated macrolide nitrate E-11 as white amorphous solid (63%, two steps).

Example 9

Synthesis of E-16

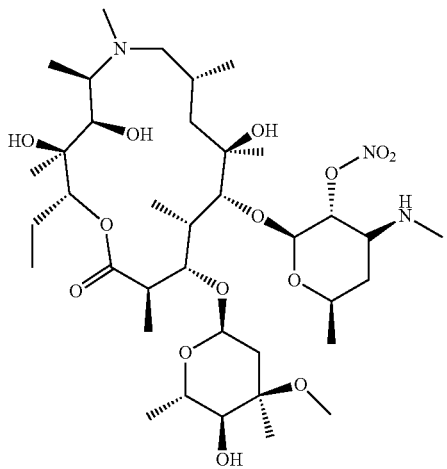

Azithromycin (20.0 g; 26.7 mmol) was dissolved in 120 ml of MeOH. NaHCO$_3$ (6.0 g; 71.5 mmol) was added, followed by a solution of K$_2$CO$_3$ (12.0 g; in water (80 ml; cooled down to RT), and finally iodine (6.3 g; 24.8 mmol). The mixture was stirred vigorously at ambient temperature until the dark color had disappeared. A second batch of iodine (6.3 g; 24.8 mmol) and K$_2$CO$_3$ carbonate (4.2 g; 30 mmol) were added. The procedure [addition of iodine 6.3 g and K$_2$CO$_3$ (4.2 g; 30 mmol)] was repeated until MS showed (almost) full conversion. Sodium bisulfite was added to remove excess oxidants, and all volatiles were evaporated. The solid residue was finely ground and extensively extracted via Soxhlet extraction with acetonitrile. The extract was concentrated to ca. 75 ml and left standing at ambient temperature at least for 1 day and subsequently for another day in the fridge. All solids were collected and recrystallized from MeOH spiked with ca. 1 to 2 ml of water. Crystallization proceeded for about 3 days in an open vessel to yield 10 g (51%) of 3'-N-demethyl-azithromycin (E-16). A second crop can be obtained from the mother liquors.

Example 10

Synthesis of E-20

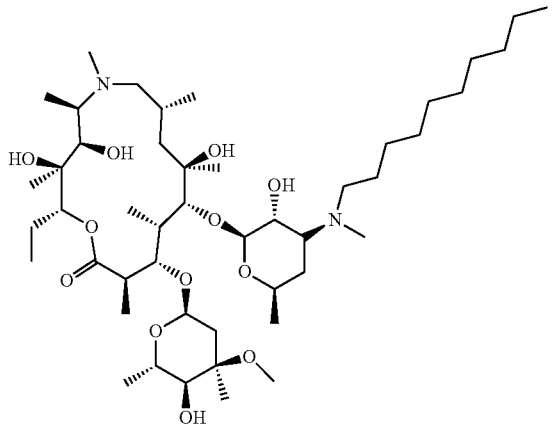

A solution of E-16 (5 mmol) in DMSO (20 ml) was treated with decyl bromide (6 mmol) at ambient temperature. Stirring continued for 12 h until TLC (acetone-cyclohexane 1:3, 1% Et$_3$N) indicated consumption of starting materials. The system was diluted with EtOAc (50 ml) and extracted with water (3×30 ml). The organic phase was dried over sodium sulfate. Evaporation of the solvent and drying at vacuum yielded E-20 as white amorphous foam (61%).

Example 11

Synthesis of E-25

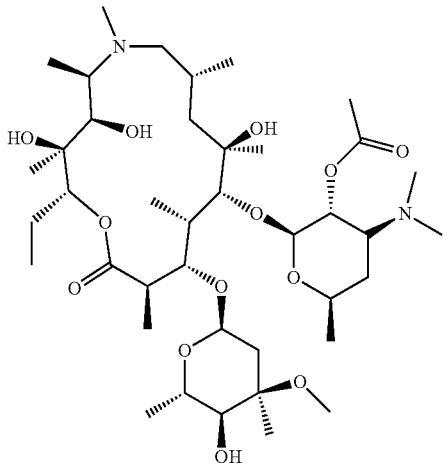

A solution of azithromycin (13 mmol) and pyridine (13 mmol) in DCM (80 ml) was cooled to 0° C. in an ice bath. A solution of acetic anhydride (14 mmol) in DCM (20 ml) was slowly added to the system. Afterwards the reaction mixture was allowed to warm up to ambient temperature and stirring was continued until TLC (acetone-cyclohexane 1:3, 1% Et$_3$N) indicated complete consumption of the starting materials. The system was extracted with an aqueous solution of NH$_4$Cl (2×50 ml) and water (3×50 ml). After drying over Na$_2$SO$_4$ all volatile components were evaporated in vacuo, traces of pyridine were removed by coevaporation with toluene (2×). The product E-25 was a white amorphous solid (67%).

Example 12

Synthesis of E-22

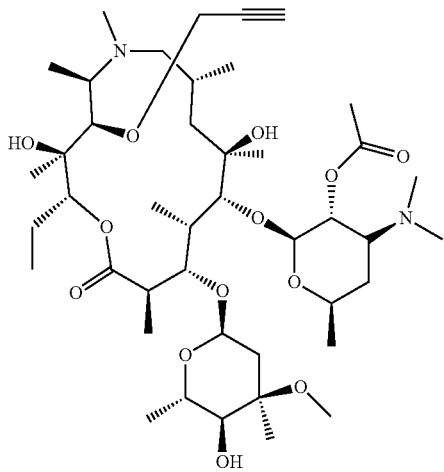

A solution of E-25 (4 mmol) in dry THF (30 ml) was cooled to 0° C. in an ice bath. A solution of propargyl bromide (4.4 mmol, 80% in toluene) was added slowly to the system. Afterwards the reaction mixture was allowed to warm up to ambient temperature and stirring was continued until TLC (acetone-cyclohexane 1:3, 1% Et$_3$N) indicated complete consumption of the starting materials. The system was diluted with EtOAc (50 ml) and extracted with water (3×50 ml). After drying over Na$_2$SO$_4$ volatile components were evaporated in vacuo. Purification by column chromatography (acetone-cyclohexane 1:3, 1% Et$_3$N) furnished E-22 as white amorphous powder (57%).

Example 13

Synthesis of E-12

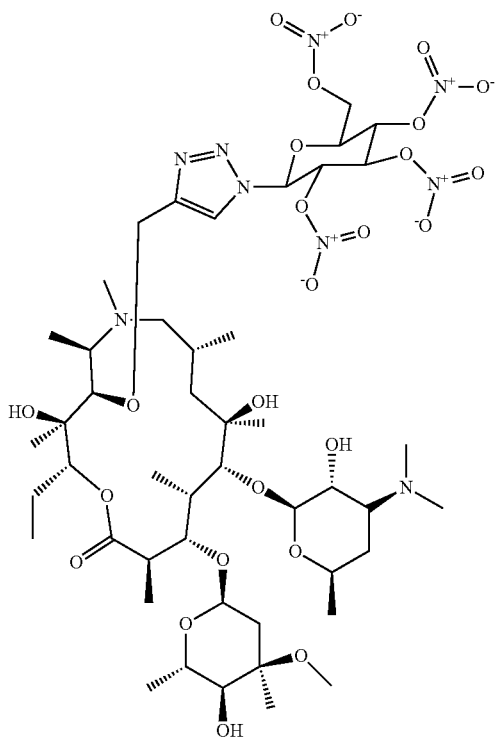

A solution of E-22 (0.5 mmol), 1-5 (0.5 mmol) and DIPEA (1 mmol) in toluene (5 ml) was treated with triethylphosphito copper(I) iodide complex (0.05 mmol) at ambient temperature. Stirring was continued until TLC (ethyl acetate-cyclohexane 1:1) indicated complete consumption of the starting materials. The mixture was concentrated in vacuo and purified by column chromatography (acetone-cyclohexane 1:1→acetone). The product E-12 was obtained as colorless foam (32%).

Example 14

Synthesis of E-23

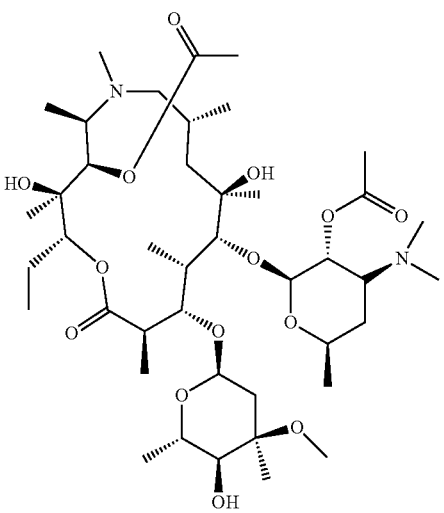

A solution of E-25 (5 mmol) and pyridine (5 mmol) in DCM (40 ml) was treated with acetic anhydride (7 mmol) at ambient temperature. Stirring was continued until TLC (acetone-cyclohexane 1:3, 1% Et$_3$N) indicated complete consumption of the starting materials. The system was extracted with an aqueous solution of NH$_4$Cl (2×20 ml) and water (3×30 ml). After drying over Na$_2$SO$_4$ all volatile components were evaporated in vacuo, traces of pyridine species were removed by co-evaporation with toluene (2×). The product E-23 was a white amorphous powder (54%).

Example 15

Synthesis of E-17

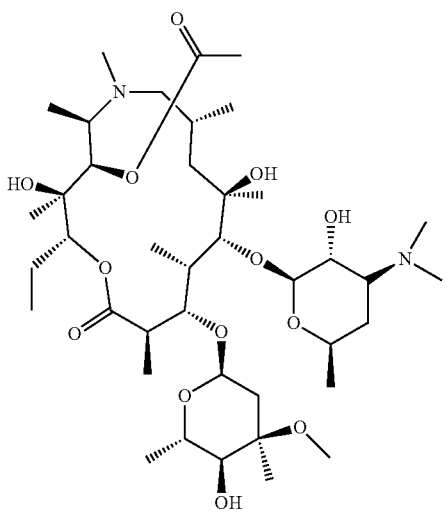

A solution of E-23 (2 mmol) in MeOH (30 ml) was vigorously stirred at 50° C. until TLC (acetone-cyclohexane 1:3, 1% Et₃N) indicated complete deacetylation of the starting materials. Volatile components were removed in vacuo, the product E-17 was obtained as white amorphous foam (73%).

Alternative Synthesis:

Compound E-2 (619 mg, 0.74 mmol) was charged in a round bottom flask. To this was added a solution of acetic acid/methanol (2:1, 15 mL). To the stirred solution, was added Zn powder (368 mg, 5.63 mmol, 7.6 eq). The resulting suspension was stirred at room temperature and progressively monitoring the disappearance of the starting material (approx. 3 h). The suspension was filtered and the filtrate evaporated in vacuo. The residue was taken up in dichloromethane (15 mL) producing some white precipitate. The precipitate was filtered off. The dichloromethane filtrate was washed with 10% aqueous Na₂CO₃ solution (2×), water (1×) and dried over anhydrous Na₂SO₄. The solvent was evaporated in vacuo producing E-17 as a white solid (475 mg, 81% yield).

Example 16

Synthesis of E-26

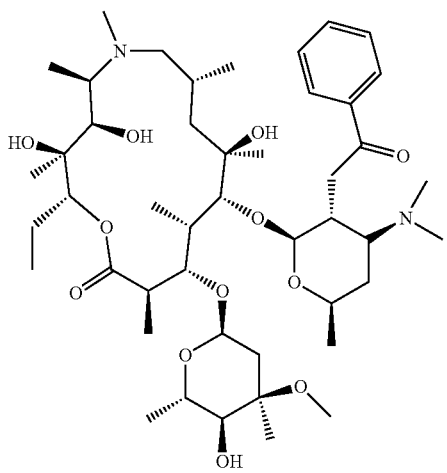

A solution of azithromycin (13 mmol) and pyridine (13 mmol) in DCM (80 ml) was cooled to 0° C. in an ice bath. A solution of benzoyl chloride (14 mmol) in DCM (20 ml) was slowly added to the system. Afterwards the reaction mixture was allowed to warm up to ambient temperature and stirring was continued until TLC (acetone-cyclohexane 1:3, 1% Et₃N) indicated complete consumption of the starting materials. The system was extracted with an aqueous solution of NH₄Cl (2×50 ml) and water (3×50 ml). After drying over Na₂SO₄ all volatile components were evaporated in vacuo, traces of pyridine species were removed by co-evaporation with toluene (2×). Column chromatography (acetone-cyclohexane 1:3, 1% Et₃N) yielded the product E-26 as a white amorphous foam (44%).

Example 17

Synthesis of E-13

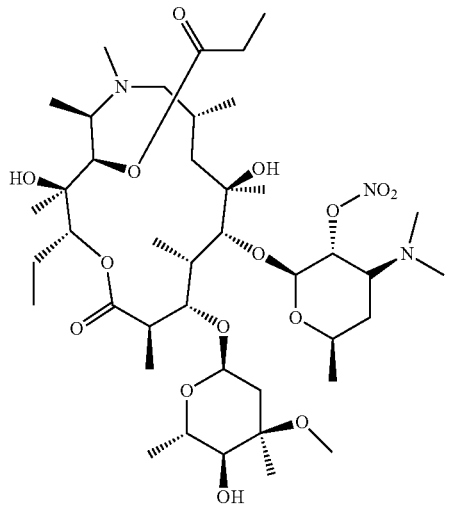

A solution of E-5 (1 mmol) and propionic acid (1.2 mmol) in 1,2-dichloroethane (3 ml) was treated portion wise with EDCI (3×0.8 mmol) and DMAP (1 mmol). The mixture was heated to 55° C. and stirred for 6 days. After TLC (acetone-cyclohexane 1:3) indicated complete consumption of the starting materials the mixture was diluted with EtOAc (30 ml) and extracted with water (3×20 ml). After drying over Na₂SO₄ the organic phase was evaporated and the remains were purified by column chromatography (acetone-cyclohexane 1:3). The product E-13 was obtained as colorless amorphous foam (42%).

Example 18

Synthesis of E-14

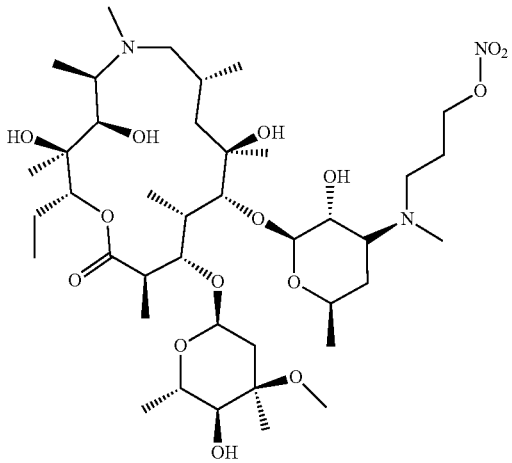

3'-N-desmethyl-azithromycin (I-1) (300 mg; 0.41 mmol) and 1-bromo-3-nitrooxy-propane[17] (90 mg, 0.49 mmol) were dissolved in dry DMSO (1.2 ml). The mixture was shaken at 23° C. for 3 hours. Afterwards additional 1-bromo-3-nitrooxy-propane (90 mg, 0.49 mmol) was added and shaking was continued for another hour. Once again, 1-bromo-3-nitrooxy-propane (90 mg, 0.49 mmol) was added, the reaction mixture was shaken for additional 90 min., and then kept in the freezer (−16° C.) over night. The next morning additional 1-bromo-3-nitrooxy-propane (90 mg, 0.49 mmol) was added and the mixture was shaken for one hour. Water and DCM were added; after extraction, the organic phase was dried (Na$_2$SO$_4$) and concentrated to dryness (without heating). The crude product was purified by column chromatography (eluent: CHCl$_3$:Isopropanol: NH$_3$ (7 M in MeOH 30:1:1).

Example 19

Synthesis of (I-5)

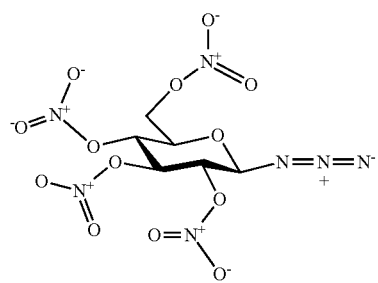

Azido-β-D-Glucopyrano side is synthesized from corresponding sugar acetate as is known to literature[16]. After removal of any protective groups sugar azide is nitrated following above procedure. Due to its high explosive risk the substance is always kept as DCM solution and is stashed in the refrigerator.

Example 20

Synthesis of E-24

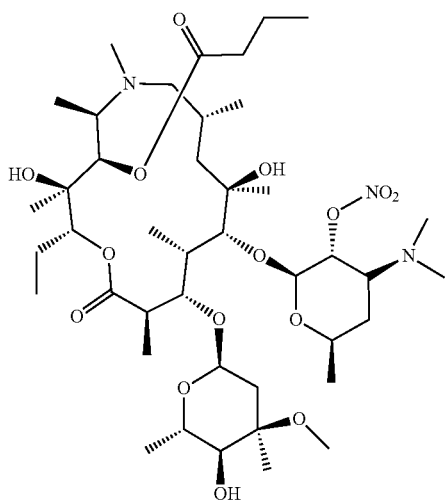

Compound E-1 (405 mg, 0.51 mmol) was taken up in dichloromethane (15 mL). The resulting solution was cooled to 0° C. After 5 minutes, butyryl chloride (60 mL, 61.8 mg, 0.58 mmol, 1.1 eq.) was added. The reaction was stirred for 10 min. at this temperature, at which point, the reaction was allowed to warm to room temperature, where it was stirred until reaction completion (2 h, or upon continuous monitoring). The reaction was washed with a 10% Na$_2$CO$_3$ aq. solution (3×) followed by H$_2$O (3×), dried over anhydrous Na$_2$SO$_4$ and evaporated in vacuo to give E-24 as a white foam (332 mg, 75% yield).

Example 21

Synthesis of E-18

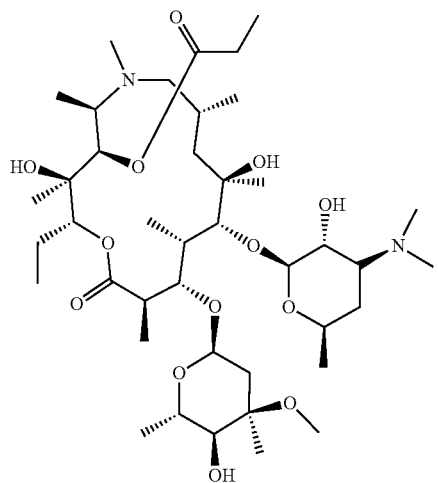

Compound E-5 (CSY 1076) (126 mg, 0.15 mmol) was charged in a round bottom flask. To this was added a solution of acetic acid/methanol (2:1, 12 mL). To the stirred solution, was added Zn powder (74 mg, 1.12 mmol, 7.6 eq). The resulting suspension was stirred at room temperature and progressively monitoring the disappearance of the starting material (approx. 3 h). The suspension was filtered and the filtrate evaporated in vacuo. The residue was taken up in dichloromethane (10 mL) producing some white precipitate. The precipitate was filtered off. The dichloromethane filtrate was washed with 10% aqueous Na$_2$CO$_3$ solution (2×), water (1×) and dried over anhydrous Na$_2$SO$_4$. The solvent was evaporated in vacuo producing E-18 as a white solid (96 mg, 80% yield).

The reduction conditions for removal of the NO$_2$ group was applied to the syntheses of E-19 from E-24 providing the desired product in 78% yield.

Example 22

Synthesis of E-19

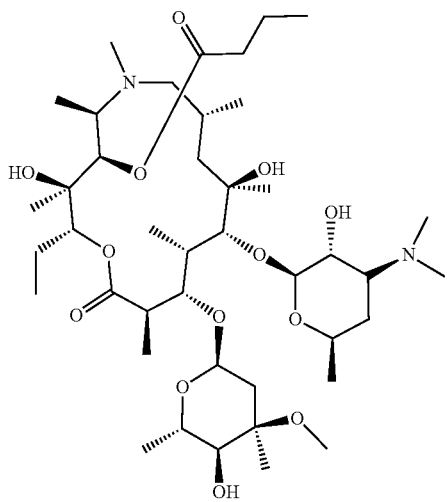

Compound E-24 CSY 4636 (100 mg, 0.12 mmol) was charged in a round bottom flask. To this was added a solution of acetic acid/methanol (2:1, 12 mL). To the stirred solution, was added Zn powder (88 mg, 1.35 mmol, 11.6 eq). The resulting suspension was stirred at room temperature and progressively monitoring the disappearance of the starting material (approx. 3 h). The suspension was filtered and the filtrate evaporated in vacuo. The residue was taken up in dichloromethane (15 mL) producing some white precipitate. The precipitate was filtered off. The dichloromethane filtrate was washed with 10% aqueous $Na_2CO_3$ solution (2×), water (1×) and dried over anhydrous $Na_2SO_4$. The solvent was evaporated in vacuo producing E-19 as transparent gel (74 mg, 78% yield).

Example 23

Synthesis of E-81

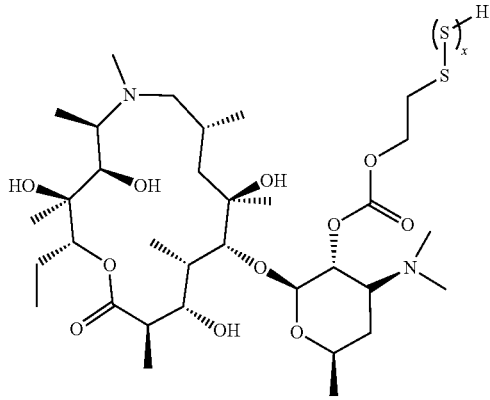

250 mg of 2'-(2-Mercaptoethoxy)carbonyl-3-decladinosylazithromycin and 250 mg of ammonium polysulfide are mixed with 10 ml of degassed and argonized glacial acetic acid and stirred with exclusion of oxygen for 12 h. All volatiles are removed in vacuo, and the residue is extracted with oxygen free saturated aqueous sodium hydrogen carbonate solution 3 times. The residue is washed with water (oxygen free), dried in vacuo and used as such.

Example 24

Synthesis of E-82

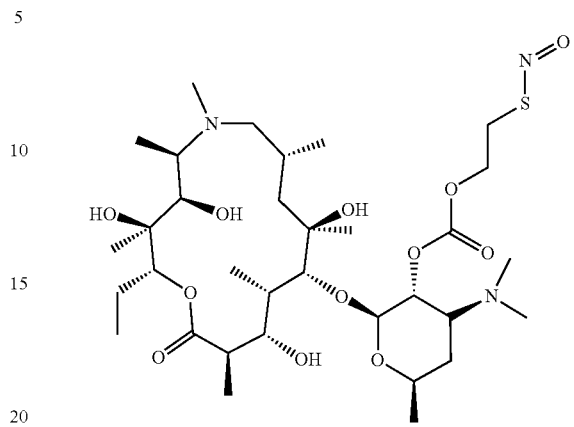

250 mg of 2'-(2-Mercaptoethoxy)carbonyl-3-decladinosylazithromycin are dissolved in a mixture of 5 ml of tert. butanol and 5 ml of dichloromethane. 250 µl of tert. butylnitrile are added, and the mixture is stirred for 48 h with exclusion of light. All volatiles are removed i.v. keeping the temperature below 20° C. and light excluded. The red residue is used as such

Example 25

Synthesis of E-74

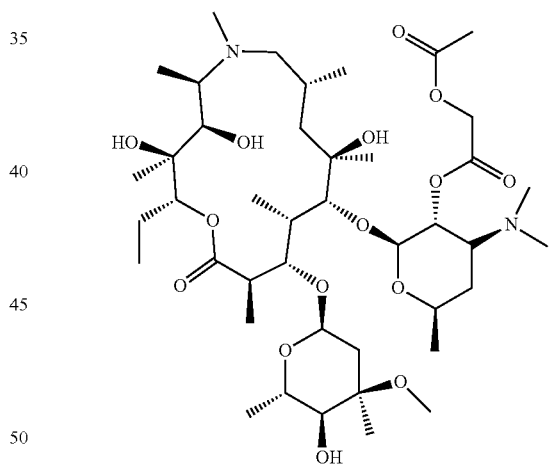

380 mg of Azithromycin are dissolved with 20 ml of DMF and cooled in an ice bath. 41 µl of pyridine and then 85 mg (1.1 eq.) of rac-2-acetoxy propionyl chloride, dissolved with 1 ml of dichloromethane, are added and the mixture is allowed to warm up to room temperature with stirring. When mass spectrometry indicates consumption of the macrolide, the mixture is diluted with 50 ml of ethyl acetate, extracted twice with water, 3 times with saturated aqueous sodium hydrogen carbonate solution, once again with water and brine, each, and dried over sodium sulfate. After evaporation and vacuum drying, the diastereomeric mixture (1:1) of target compound E-74 remains as a slightly yellowish foam.

Yield: 385 mg

MS: m/z=863.5 ([M+H]$^+$)

The same procedure can be applied in preparing E-77, E-83, E-84, E-85 and E-86.

TABLE 5

Typical Products from the Acylation Procedures

| Entry | Acylating agent | Product structure | Yield [%] | ([M + H]+ |
|---|---|---|---|---|
| E-83 | O-Phenyl chlorothionoformate | | 66 | 885.7 |
| E-85 | 2-Bromoethylchloroformate | | 82 | 899.6 |
| E-84 | Hexanoylchloride | | 93 | 847.6 |

TABLE 5-continued
Typical Products from the Acylation Procedures
| Entry | Acylating agent | Product structure | Yield [%] | ([M + H]+ |
|---|---|---|---|---|
| E-77 | Lipoyl chloride | 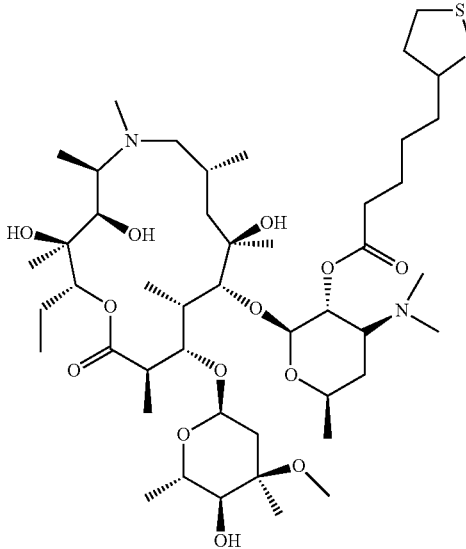 | 72 | 936.8 |
| E-86 | Allylchloroformate | 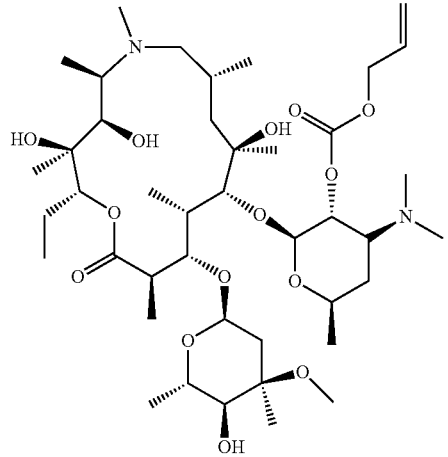 | 82 | 833.5 |
| E-540 | O-Phenyl chlorothionoformate | 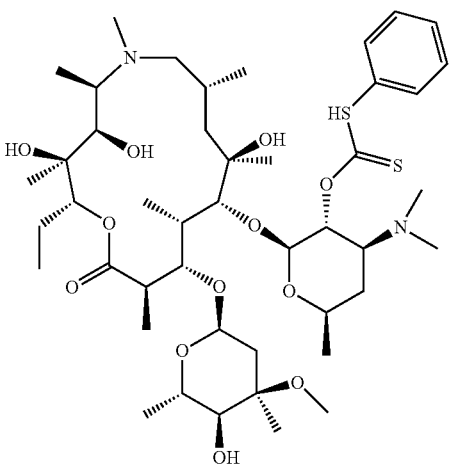 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2OC(=S)Sc2ccccc2)[C@](C)(O)C[C@@H](C)CN(C)[C@H](C)[C@@H](O)[C@]1(C)O] | 23 | 884 |

TABLE 5-continued

Typical Products from the Acylation Procedures

| Entry | Acylating agent | Product structure | Yield [%] | ([M + H]+ |
|---|---|---|---|---|
| E-26 | Benzoyl | 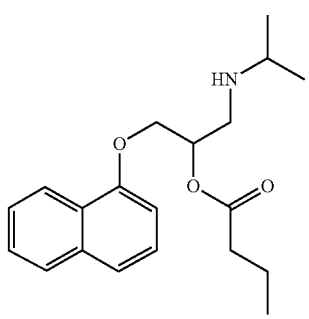 [SMILES: CCCC(=O)OC(CNC(C)C)COc1cccc2ccccc12] | 44 | 853 |

Example 26

General Procedure: Synthesis of n-Butyryl-Propranolol, Compound E-133

Propranolol HCl (200 mg, 0.68 mmol) was taken up in dichloromethane (4 mL). To this was added dropwise butyryl chloride (69 µL, 0.71 mmol) and the reaction was stirred at room temperature for 1 hour. To the reaction was added triethylamine (194 µL, 1.4 mmol). After 30 min, additional butyryl chloride (30 µL, 0.3 mmol) was added. Reaction was monitored by the disappearance of starting material. The reaction was stopped after 20 min by the addition of 10 mL 10% aqueous $Na_2CO_3$ solution. The two phases were stirred for 5 min separated. The organic layer was washed successively with 10% aqueous $Na_2CO_3$ (1×), $H_2O$ (1×) and saturated aq. NaCl (1×), dried with $Na_2SO_4$ and evaporated in vacuo to get an oil film. 5 mL HCl in $Et_2O$ (2M) and 1 mL MeOH was added and stirred for 5 min, then evaporated in vacuo and dried with the vacuum pump under nitrogen for 1 hour to get a brown oil (yield 91%).

Example 27

General Procedure: Synthesis of n-Butyryl-Hydroxychloroquine, Compound E-89

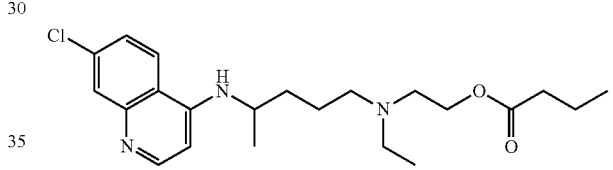

Hydroxychloroquine sulfate (1099 mg, 2.53 mmol) was charged into a round bottom flask. $H_2O$ (10 mL) and dichloromethane (10 mL) were added. Pyridine (412 µL, 5.1 mmol) was added and the reaction stirred vigorously for 5 min. Butyric anhydride (420 µL, 2.65 mmol) was added and the reaction stirred at room temperature for 3 h. The phases were separated and the dichloromethane layer was washed successively with a saturated aqueous $NH_4Cl$ solution (2×15 mL), $H_2O$ (2×10 mL), dried over $Na_2SO_4$ and evaporated in vacuo. Co-evaporation with toluene is necessary to remove residual pyridine from the system. This was followed by re-dissolving the residue in DCM and solvent evaporation twice to produce a yellow oil (93 mg, 9% yield).

This procedure can be applied for the synthesis of the following compounds E-87 to E-88, E-90 to E-97.

Example 28

Typical methylation reaction of Hydroxychloroquine or Propranolol was achieved using Eschweiler-Clarke-methylation reaction. Acylation reactions were carried out using typical procedures described above.

Example 29

Compounds, prepared by reacting a carrier molecule with acylating agents. These carrier molecules are prepared by reacting symmetric or unsymmetric di- or poly-epoxides with secondary amines, thus containing the common structural element of 2 or more alcohols, vicinally neighbored by a tertiary amine.

Alternatively, carrier molecules can be prepared by reacting epoxides with diethanolamine. The reaction products are containing 2-hydroxy tertiary amines.

TABLE 6

Examples for di- or polyepoxides

| Entry | Name | CAS-No. | No. of epoxide functions |
|---|---|---|---|
| A | 1,3-Butadiene diepoxide | 1464-53-5 | 2 |
| B | 1,4-Butandiole diglycidylether | 2425-79-8 | 2 |
| C | N,N-Diglycidylaniline | 2095-06-9 | 2 |
| D | Resorcinol diglycidylether | 101-90-6 | 2 |
| E | Ethylen glycol diglycidylether | 2224-15-9 | 2 |
| F | 1,7-octadienediepoxide | 2426-07-5 | 2 |
| G | Diglycidyl ether | 2238-07-5 | 2 |
| H | 1,2,4,5,9,10-Triepoxydecane | 52338-90-6 | 3 |
| I | N,N-Diglycidyl-4-glycidyloxyaniline | 5026-74-4 | 3 |
| J | Poly(ethylene glycol) diglycidyl ether (average $M_n$ 500) | 72207-80-8 | 2 |
| K | Glycerol diglycidylether | 72207-80-8 | 2 |
| L | 4,4'-Methylenebis(N,N-diglycidylaniline) | 28768-32-3 | 4 |
| M | Bis[4-(glycidyloxy)phenyl]methane | 2095-03-6 | 2 |

TABLE 7

Examples for secondary amines

| Entry | Name | CAS-No. |
|---|---|---|
| 1 | Dimethylamine | |
| 2 | Morpholine | |
| 3 | 4-Methylpiperazine | |
| 4 | Piperidine | |
| 5 | 1,2,3,4-Tetrahydroisoquinoline | 91-21-4 |
| 6 | Diethylamine | |
| 7 | Dioctylamine | |
| 8 | Diethanolamine | |
| 9 | Sarcosine methyl ester hydrochloride | 13515-93-0 |
| 10 | (R)-pyrrolidine-2-carboxylic acid methyl ester (Prolin methylester) | |
| 11 | Ethyl 1,4-diazepan-1-ylacetate dihydrochloride | |

TABLE 8

Structural examples for carrier molecules

| Combination of poly-epoxide and amine | Structural Example |
|---|---|
| H1 | (structure) |
| G5 | (structure) |
| C8 | (structure) |
| A-7-C | (structure) |
| B2 | (structure) |

The 2-aminoalcohols of these carriers can be esterified to short chain carboxylic acids or nitric acid. One molecule can contain esters of different of these acids. Examples for short chain carboxylic acids are:

Acetic acid, propionic acid, butyric acid, isobutyric acid, valeric acid, 2-methylbutyric acid, 3-methylbutyric acid, lactic acid, pyruvic acid, 3-phenylpropionic acid, succinic acid, maleic acid, fumaric acid, malic acid, lactic acid butyrate (lactic acid butanoate), 2-acetoxy propionic acid, mandelic acid, benzoic acid.

Structural Examples of Such Esters are:

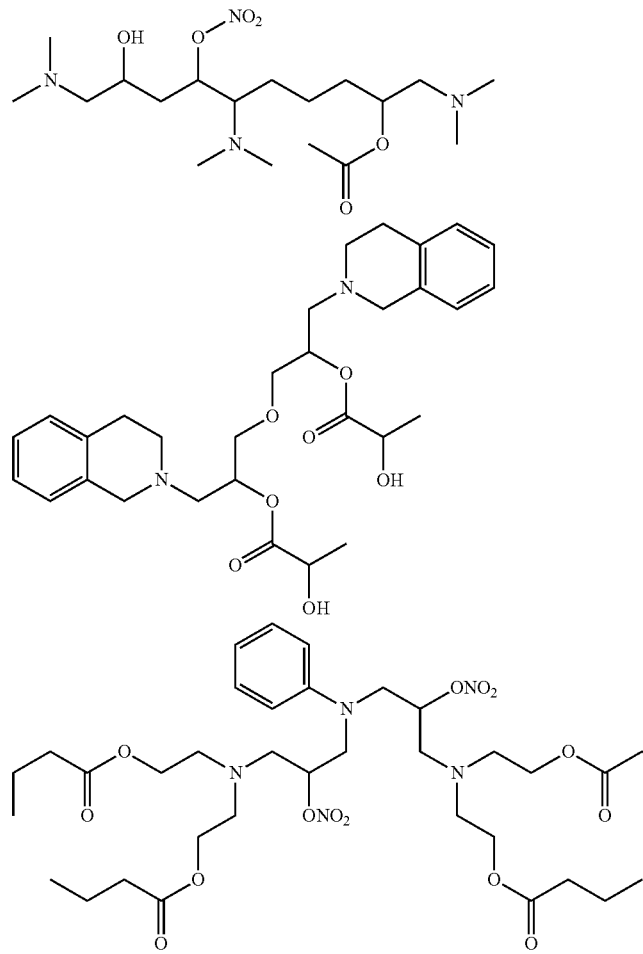

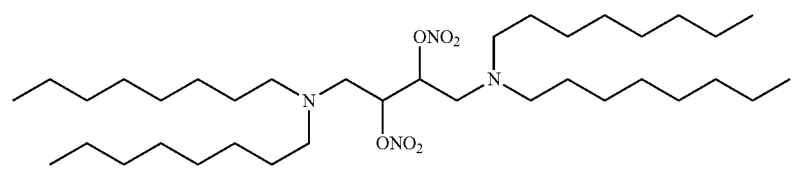

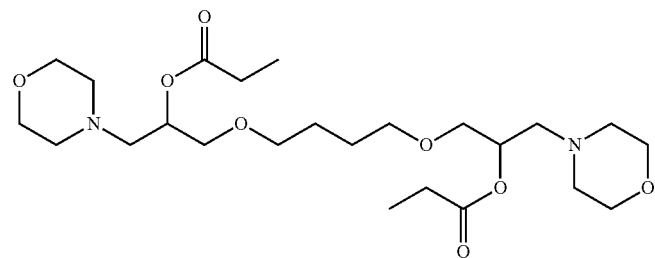

Alternatively, these carrier molecules are prepared by reacting symmetric or unsymmetric di- or polyamines with epoxides, thus containing the common structural element of 2 or more alcohols, vicinally neighbored by a tertiary amine.

TABLE 9

Examples for di- or polyamines

| Entry | Name | CAS. No. | No. of reactive amines |
|---|---|---|---|
| N | Spermine | 71-44-3 | 4 |
| O | Spermidine | 124-20-9 | 3 |
| P | Piperazine | 110-85-0 | 2 |
| Q | 1-(2-Aminoethyl)piperazine | 140-31-8 | 2 |
| R | L-Lysine | 56-87-1 | 2 |
| S | Homopiperazine | 505-66-8 | 2 |
| T | 1,3-Diamino-2-propanol | 616-29-5 | 2 |
| U | 1,3,5-Triamino-1,3,5-trideoxy-cis-inositol trihydrochloride | 6988-69-8 | 3 |

TABLE 9-continued

Examples for di- or polyamines

| Entry | Name | CAS. No. | No. of reactive amines |
|---|---|---|---|
| V | 1,2,3,4-Tetrahydroquinoxaline | 3476-89-9 | 2 |
| W | Tetraethylenepentamine | 112-57-2 | 5 |

TABLE 10

Examples for epoxides

| Entry | Name | CAS No. |
|---|---|---|
| 12 | Propylene oxide | 75-56-9 |
| 13 | Cyclohexen oxide | 286-20-4 |
| 14 | Ethyl 2,3-epoxypropionate | 4660-80-4 |
| 15 | Styrene oxide | 96-09-3 |
| 16 | Glycidol | 556-52-5 |

TABLE 11

Structural examples for carrier molecules

Combination of poly-epoxide and amine / Structural Example

Q12

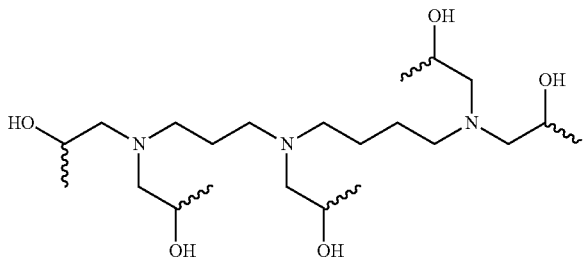

Q13

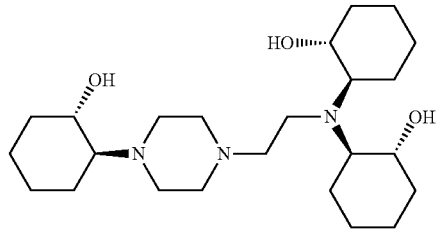 [SMILES: O[C@@H]1CCCC[C@H]1N(CCN1CCN([C@H]2CCCC[C@@H]2O)CC1)[C@@H]1CCCC[C@H]1O]

R16

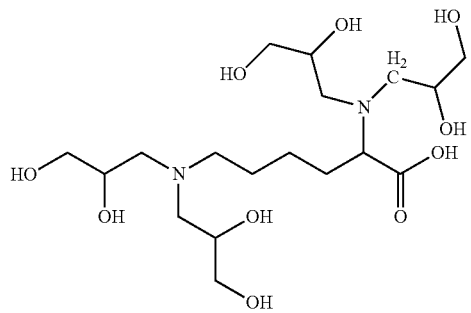 [SMILES: O=C(O)C(CCCCN(CC(O)CO)CC(O)CO)N(CC(O)CO)CC(O)CO]

TABLE 11-continued

Structural examples for carrier molecules

| Combination of poly-epoxide and amine | Structural Example |
|---|---|
| S14 | |
| T15 | |

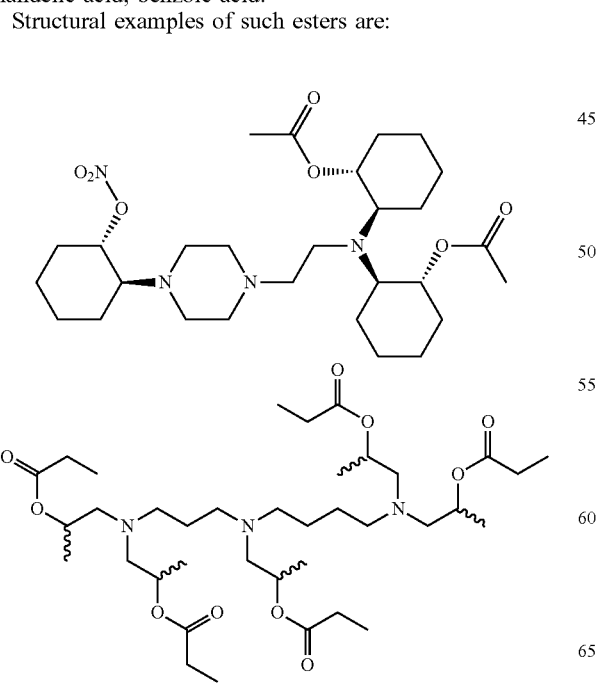

The 2-aminoalcohols of these carriers can be esterified to short chain carboxylic acids or nitric acid. One molecule can contain esters of different of these acids. Examples for short chain carboxylic acids are:

Acetic acid, propionic acid, butyric acid, isobutyric acid, valeric acid, 2-methylbutyric acid, 3-methylbutyric acid, lactic acid, pyruvic acid, 3-phenylpropionic acid, succinic acid, maleic acid, fumaric acid, malic acid, lactic acid butyrate (lactic acid butanoate), 2-acetoxy propionic acid, mandelic acid, benzoic acid.

Structural examples of such esters are:

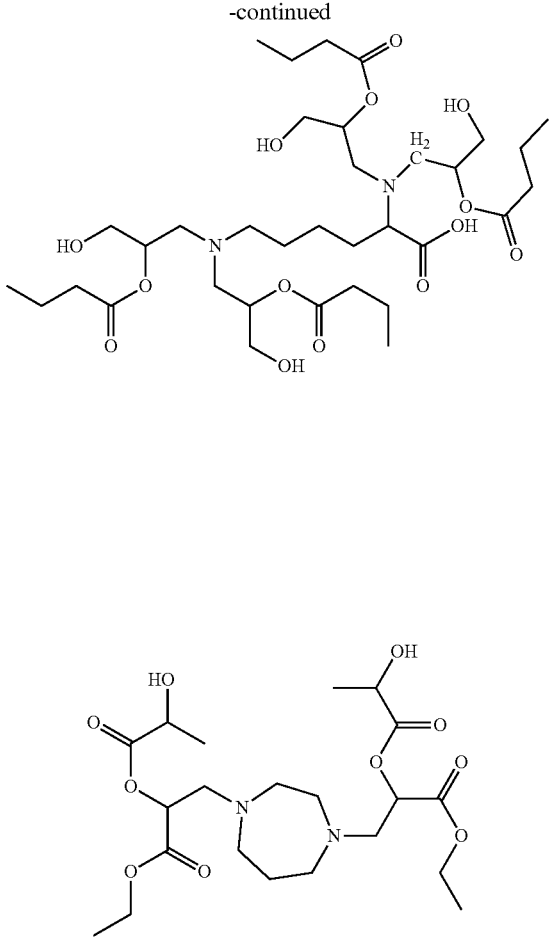

-continued

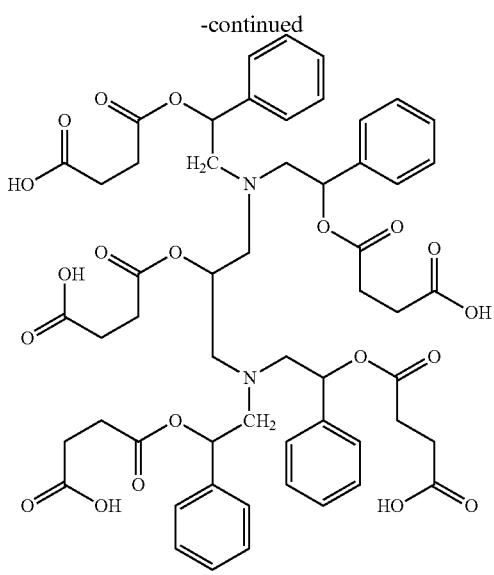

Example 30

Synthesis of rac. 2'-Deoxy-2'-S-thioacetyl Propranolol [18]

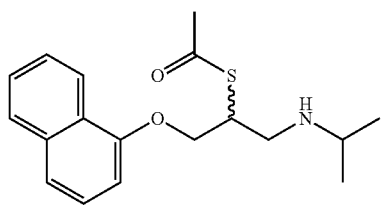 [SMILES: CC(=O)SC(CNC(C)C)COc1cccc2ccccc12]

Diethyl azodicarboxylate (DEAD, 10 mmol) is added to a stirred (magnetic stirrer, 300 rpm) solution of triphenylphosphin (10 mmol) in dry THF (25 mL) at 0° C. and treatment is continued for 30 min. Propranolol (5 mmol) and thioacetic acid (10 mmol) both dissolved in THF (10 mL) are added dropwise and stirring is continued for 1 h at 0° C. and further 2 h at ambient temperature. Any precipitates are filtered off, the remaining solution is concentrated in vacuo and desired product is isolated by column chromatography (silica gel, cyclohexane-ethyl acetate).

Synthesis of rac. 2'-Deoxy-2'-S-thio Propranolol Sodium Salt

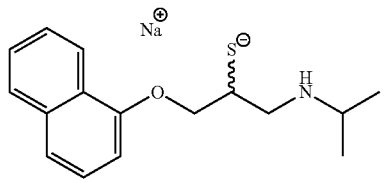 [SMILES: CC(C)NCC([S-])COc1cccc2ccccc12 ; [Na+]]

rac. T-Deoxy-T-S-thioacetyl propranolol (10 mmol) is dissolved in methanol (20 mL) while stirring (magnetic stirrer, 300 rpm) and sodium methoxide (10 mmol) is added at 0° C. The system is allowed to warm up to ambient temperature and treatment is continued until TLC (cyclohexane-ethyl acetate) indicates full conversion of starting materials. Afterwards the reaction mixture is rinsed into ice cold diethyl ether (100 mL). Any precipitates are filtered off and are dried in vacuo to yield a white to slightly yellow product.

Example 31

Synthesis of rac. 2-O-Nitrolactic Acid

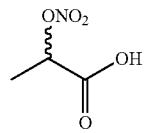

Lactic acid (10 mmol) is suspended in acetonitrile (20 mL) in a 3-necked round bottom flask and is cooled to 0° C. in an ice bath while stirring (300 rpm). Diphosgene is added (5 mmol) followed by careful dropwise addition of silver nitrate solution (20 mmol, dissolved in acetonitrile). The mixture is stirred for 30 min at 0° C., subsequently is allowed to warm up to ambient temperature and stirring is continued for further 30 min. Afterwards any precipitates are filtered off and the mixture is carefully concentrated in vacuo. As crude products are likely to be explosive compounds the system was not fully dried but taken up in THF (10 mL) to be immediately used in the following step.

Synthesis of rac. 2'-O-(2-O-Nitrolactyl) Propranolol—E-142

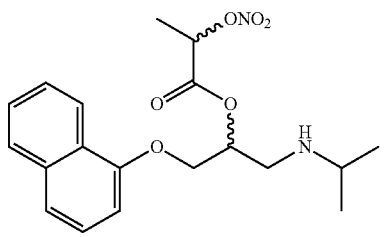

Diethyl azodicarboxylat (DEAD, 10 mmol) is added to a stirred (magnetic stirrer, 300 rpm) solution of triphenylphosphin (10 mmol) in dry THF (25 mL) at 0° C. and treatment is continued for 30 min. Propranolol (5 mmol) and rac. 2-O-nitrolactic acid (10 mmol) both dissolved in THF (10 mL) are added dropwise and stirring is continued for 1 h at 0° C. and further 2 hours at ambient temperature. Any precipitates are filtered off, the remaining solution is concentrated in vacuo and desired product is isolated by column chromatography (silica gel, cyclohexane-ethyl acetate).

Example 32 rac. Bis-(2'-Deoxy-2'-S—S-disulfido Propranolol) (Putative)[19]

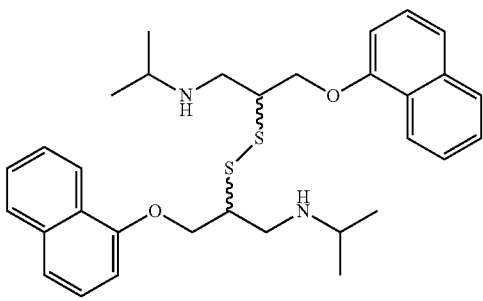 [SMILES: CC(C)NCC(COc1cccc2ccccc12)SSC(CNC(C)C)COc1cccc2ccccc12]

A round bottom flask is charged with ethyl acetate (10 mL), graphite (3 g), iodine (0.5 mmol) and cerium(III) chloride heptahydrate (1 mmol). The mixture is stirred for 10 min at ambient temperature, followed by addition of rac. 2'-deoxy-2'-S-thio propranolol sodium salt (10 mmol). Treatment is continued until TLC (cyclohexane-ethyl acetate) indicates full conversion of starting materials. After completion the system is further diluted with additional ethyl acetate (250 mL) and is washed with a saturated solution of aqueous sodium thiosulfate, water, and is dried over sodium sulfate. Upon filtration any volatiles are removed in vacuo and the residue is subject to column chromatography (silica gel, cyclohexane-ethyl acetate).

Mixed disulfides may also be accessible in this way but require slight alterations.

Example 33—Typical Example of Synthesizing ALC Cores A-8 and A-9

Synthesis of 2-(4-pyridyl)-3-amino-4-(3-methoxyphenyl)carbonyl Pyrazole

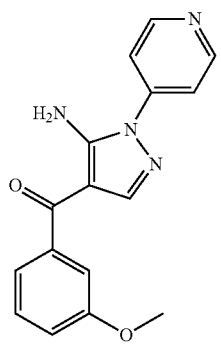 [SMILES: COc1cccc(C(=O)c2cnn(-c3ccncc3)c2N)c1]

10.96 g of 4-(N-phenyl)amino-3-(3-methoxyphenyl)carbonylacrylonitrile and 6.27 g of 4-pyridylhydrazine hydrochloride are combined with 6.2 ml of triethylamine in 140 ml of ethanol, flushed with argon and heated to reflux for 5 h. The mixture is concentrated to 50 ml and diluted with 200 ml of cyclohexane. The precipitate is filtered off and washed with diethyl ether, until no further colour is extracted any more. The remaining solid is dissolved with a mixture of dichloromethane and water (300 ml each). The organic phase is dried with brine and sodium sulfate and concentrated to dryness.

Yield: 7.07 g (61%); MS: m/z=295 ([M+H]+)

Synthesis of 2-(4-pyridyl)-3-amino-4-(3-hydroxyphenyl)carbonyl Pyrazole

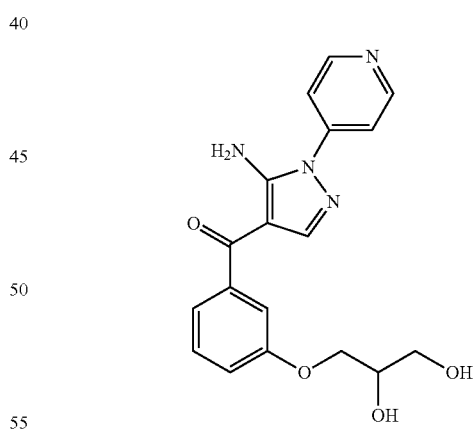

2.6 g of 2-(4-Pyridyl)-3-amino-4-(3-methoxyphenyl)carbonylpyrazole are suspended in 10 ml of a solution of 33% hydrobromic acid in acetic acid. The mixture is heated to 70° C. for 16 h. After cooling, the reaction mix is poured into 150 ml of water. The precipitate is filtered off, washed with saturated aqueous sodium hydrogen carbonate solution (twice) and water, and dissolved in 10 ml of a solution of ammonia in methanol (7M). After 30 min, all volatiles are removed by evaporation, and the residue is dissolved in 50 ml of boiling methanol. The product is precipitated by pouring into 250 ml of water. Filtration and drying yield 2.35 g of an off white powder.

Synthesis of 2-(4-pyridyl)-3-amino-4-(3-[2,3-dihydroxypropyloxy]phenyl)-carbonyl Pyrazole 2.09 g of 2-(4-Pyridyl)-3-amino-4-(3-hydroxyphenyl)carbonyl pyrazole are dissolved with 25 ml of dimethylformamide. 3.5 g of potassium carbonate and 580 mg of glycidol are added. The mixture is kept stirring at 60° C. for 18 h. The reaction mixture is partitioned between water and ethyl acetate. The organic phase is washed with water, dried with brine and sodium sulfate, and concentrated i.v. The residue is subjected to preparative HPLC to yield 1.4 g of the product.

87

Synthesis of 2-(4-pyridyl)-3-amino-4-(3-[2,3-di{butyroyloxy}propyloxy]phenyl)carbonyl Pyrazole E-199

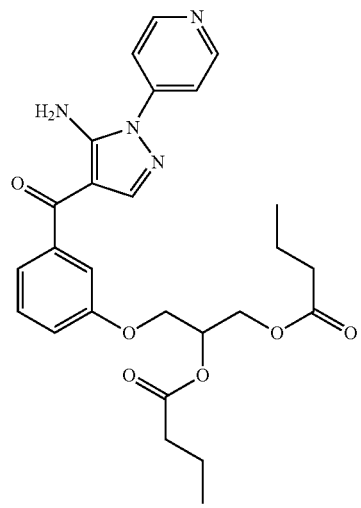 [SMILES: CCCC(=O)OCC(COc1cccc(C(=O)c2cnn(-c3ccncc3)c2N)c1)OC(=O)CCC]

500 mg of 2-(4-pyridyl)-3-amino-4-(3-[2,3-dihydroxypropyloxy]phenyl)carbonylpyrazole are dissolved with 5 ml of pyridine. 500 µl of butyric acid anhydride are added, and the mixture is stirred at 50° C. over night. 1 ml of methanol is added, and the mixture is stirred for further 30 min. The reaction is allowed to reach room temperature and partitioned between water and ethyl acetate. The organic phase is extracted with water 5 times, then with brine and dried over sodium sulfate. After evaporation of all volatiles, the product is purified by chromatography over silica gel.

Yield: 290 mg

The same conditions can be applied to synthesis of 2-(4-fluorophenyl)-3-amino-4-(3-[2,3-di{butyroyloxy}propyloxy]phenyl)carbonylpyrazole E-210

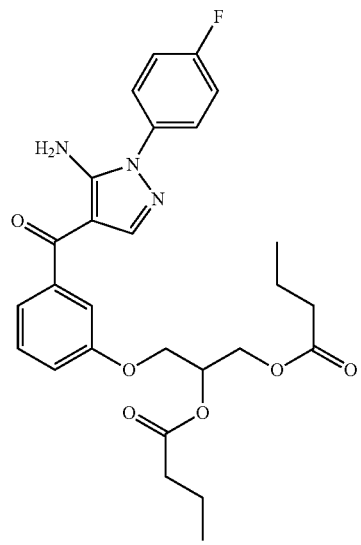 [SMILES: CCCC(=O)OCC(COc1cccc(C(=O)c2cnn(-c3ccc(F)cc3)c2N)c1)OC(=O)CCC]

88

Example 34

Synthesis of Chenodeoxycholic Acid Azithromycin-2'-ester

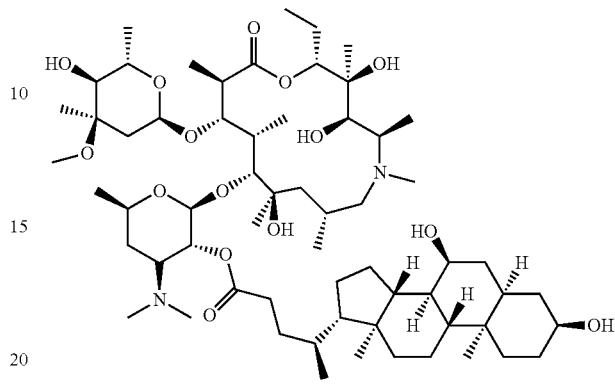

1 g of Chenodeoxy cholic acid is dissolved with 50 ml of dry dichloromethane and cooled in an ice bath. 500 mg of carbonyl diimidazole are added, and the mixture is stirred for 2 h, while reaching room temperature. 2 g of Azithromycin are added, and the mixture is stirred for 72 h. The mixture is extracted with water (3×) and then with 5% citric acid. The citric acid phase is washed with dichloromethane (2×). It is then vigorously stirred with ethyl acetate, while portions of sodium hydrogencarbonate are added, so that gas evolution is under control. When no gas is developed any more, the organic phase is isolated, washed with brine and dried over sodium sulfate. Concentration and chromatography with a gradient starting at 10% of acetone in cyclohexane (always containing 0.2% of triethylamine) yields 350 mg of the desired product.

Example 35

Synthesis of 2'-(succinyl-1-hydroxymethylferrocene)-11-nitro-Azithromycin

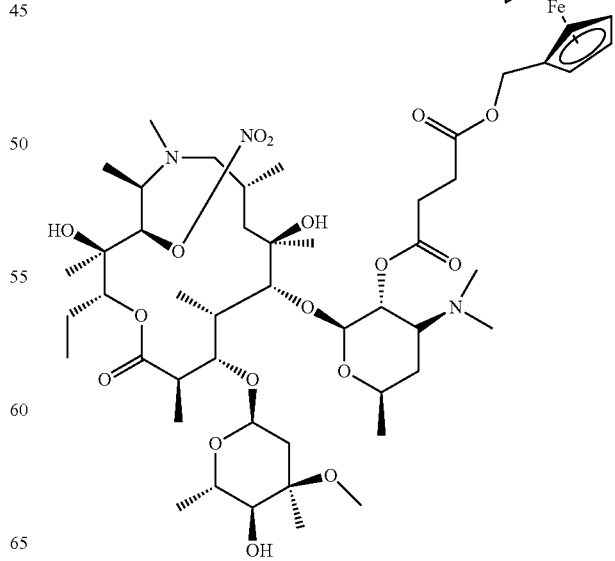

Compound E-10 (200 mg, 0.25 mmol) was dissolved in dry dichloromethane (5 mL). To this was added subsequently, 4-dimethylaminopyridine (4-DMAP, 3 mg, 0.25 mmol. 0.1 eq.) and succinic anhydride (28 mg, 0.28 mmol). The reaction was stirred overnight at room temperature. The solvent was removed in vacuo and the resulting white amorphous foam was used directly for the next step.

Fresh dry dichloromethane (5 mL) was added to the resulting foam, followed by 1-Hydroxy-methylferrocene (60 mg, 0.28 mmol, 1.1 eq.). The reaction was cooled to 0° C. and to this was added EDCI (96 mg, 0.5 mmol, 2 eq.). The reaction was allowed to progressively warm to room temperature where it was stirred overnight. Additional dichloromethane (20 mL) was added and washed several times with saturated aqueous ammonium chloride, brine (2×), dried under anhydrous $Na_2SO_4$ and the solvent removed in vacuo. The resulting crude product was purified by chromatography with a gradient starting at 10% of acetone in cyclohexane (0.2% $Et_3N$) yields 150 mg of the desired product (53%).

Similarly, the following compound may be obtained using the procedure above starting from compound E-19.

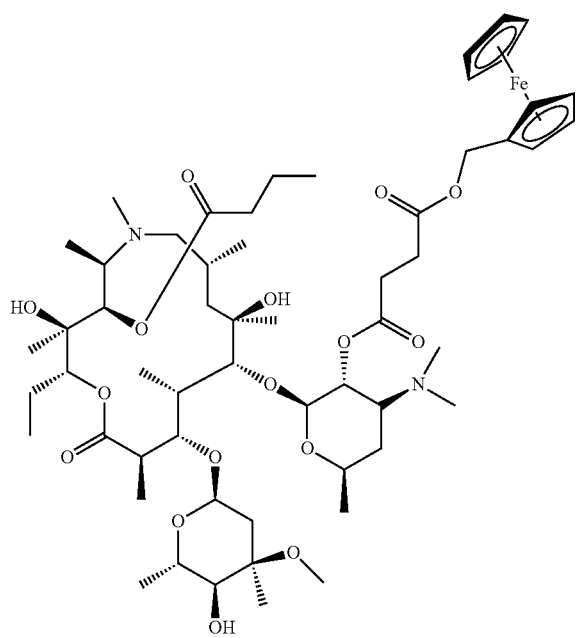

Example 36

Activity of substances in the inhibition of growth of bacteria. Bacteria including the species *Escherichia coli, Bacillus pumilus, Salmonella* sp., *Micrococcus luteus* and *Staphylococcus carnosus* are cultured in appropriate media (Luria broth for all except *S. canosus*). Overnight cultures are mixed with fresh medium to reach an optical density at 600 nM of ca. 0.1 AU. These cultures are mixed with solutions of substances to be tested at concentrations ranging from 100 μM to 0.05 μM in a microtitre plate. The growth of the culture is monitored by measuring the optical density at various times after the addition of the inhibitor. Reduction in the rate of increase in optical density corresponds to an inhibition of bacterial growth. In the following tables, the activity of various of the test substances may be observed by reductions in optical density relative to untreated control cultures. The data are summarized in Table 3 and Table 4.

TABLE 12

Inhibition of growth of *Staphylococcus carnosus* by compounds after 9-20 h:

| Conc. | Absorbance of culture medium at 600 nm | | | | | | | |
|---|---|---|---|---|---|---|---|---|
| (μM): | 100 | 50 | 25 | 13 | 6 | 3 | 2 | 0.8 |
| E-2 | 0.395 | 0.425 | 0.456 | 0.542 | 0.626 | 0815 | 0.766 | 0.760 |
| E-5 | 0.302 | 0.347 | 0.403 | 0.452 | 0.525 | | 0.805 | 0.726 | 0.819 |
| E-13 | 0.421 | 0.437 | 0.282 | 0.488 | 0.530 | | 0.668 | 0.755 | 0.765 |
| E-1 | 0.157 | 0.096 | 0.078 | 0.068 | 0.625 | | 0.864 | 0.856 | 0.902 |
| E-12 | 0.494 | 0.523 | 0.574 | 0.548 | 0.591 | | 0.577 | 0.688 | 0.783 |
| E-9 | 0.545 | 0.522 | 0.426 | 0.677 | 0.752 | | 0.830 | 0.737 | 0.765 |
| E-10 | 0.576 | 0.433 | 0.595 | 0.702 | 0.699 | | 0.768 | 0.826 | 0.862 |
| E-11 | 0.641 | 0.574 | 0.819 | 0.822 | 0.887 | | 0.890 | 0.918 | 0.941 |
| No compound | | | | | 0.887 | | | |

TABLE 13

Inhibition of growth of *Salmonella typhimurium* by compounds after 9-20 h:

| Conc. | Absorbance of culture medium at 600 nm | | | | | | | |
|---|---|---|---|---|---|---|---|---|
| (μM): | 100 | 50 | 25 | 13 | 6 | 3 | 2 | 0.8 |
| E-2 | 0.251 | 0.168 | 0.314 | 0.621 | 0.382 | 0.410 | 0.441 | 0.452 |
| E-5 | 0.390 | 0.395 | 0.396 | 0.437 | 0.478 | 0.511 | 0.568 | 0.574 |
| E-13 | 0.398 | 0.407 | 0.427 | 0.459 | 0.505 | 0.543 | 0.605 | 0.634 |
| E-1 | 0.557 | 0.484 | 0.736 | 0.722 | 0.741 | 0.711 | 0.761 | 0.722 |
| E-12 | 0.332 | 0.270 | 0.326 | 0.343 | 0.400 | 0.354 | 0.457 | 0.455 |
| E-9 | 0.221 | 0.319 | 0.395 | 0.382 | 0.348 | 0.327 | 0.272 | 0.300 |
| E-10 | 0.280 | 0.315 | 0.390 | 0.399 | 0.382 | 0.402 | 0.361 | 0.334 |
| E-11 | 0.562 | 0.650 | 0.697 | 0.633 | 0.627 | 0.623 | 0.587 | 0.555 |
| No compound | | | | | 0.943 | | | |

Example 37

Substances may act directly on bacteria, or they may act to promote the killing of the bacteria by phagocytes. To measure this effect, cultures murine macrophages are incubated with a test bacteria and the number of bacteria surviving are counted in terms of the viable colony forming units (CFU). The method for determining the rate of phagocytosis is as follows:

Intracellular killing of S. *Typhimurium* by mouse macrophage cellline J 774 A.1
- seed a monolayer of cells in 200 μl Media into the wells of a 96 well plates
- incubate O/N 37° C.
- remove medium and add fresh medium
- add Bacteria (*Salmonella typhimurium*) e.g. 5 μl of 1:100 diluted O/N culture (MOI=10) (=108 cfu/ml)
- centrifuge 10 min 800 g (2000 rpm)
- incubate 20-30 minutes at 37° C. (phagocytosis)
- remove media
- wash 1-2× with PBS
- add medium with 100 μg/ml Gentamicin, stock: 10 mg/ml (=1:100)
- incubate 45' at 37° C.
- wash 2× with PBS
- add fresh medium (200 μl/well)
- add compounds to test
- incubate 2-3 hours at 37° C.
- remove medium
- lyse cells with water: add 200 μl $H_2O$ incubate 10', push a few times through 27 gauge needle using a 1 ml syringe plate 100 Of 1:10 dilution onto LB-agar plates (=1:100 dil)
Monolayer of J 774 A.1 in 96 well plate=~1-5×104 cells
Overnight culture of *Salmonella thyphimurium*=~1×1010 cfu/ml
Overnight culture of *Staphylococcus carnosus*=~5×109 cfu/ml MOI=50 (=5 µl of 1:10 dil. O/N culture)
MOI=Multiplicity of Infection
Medium: DMEM/RPMI 7.5% FCS Example 38

The potential efficacy of a Compound for Inflammatory bowel disease may be modeled as follows. C57 BLK6 or BALBc mice are provided with drinking water containing 2.5% or 2.8% dextran sulfate. Animals are weighed and observed for signs of intestinal disturbance daily. Signs include diarrhea or occult blood. Compound is formulated by mixing with a solution of 0.1 up to 1% citric acid depending on concentration. Compound is provided by oral gavage daily. Example data for the efficacy of compounds cited here is provided in FIG. 3, 7, 8 or 10-19.

Example 39

Figure 2:
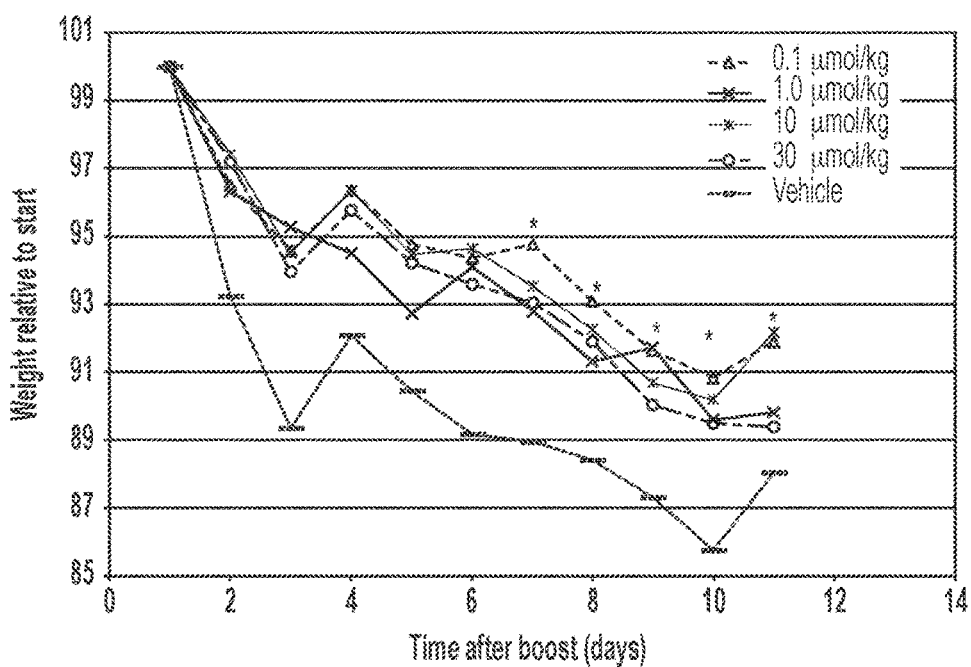
FIG. 2: Change in body weight in mice in which arthritis has been induced using bovine collagen. Animals were treated with either Vehicle (1% citric acid in water, 5 mL/kg) or the indicated doses of compound E2 µmol/kg. Data are from 10 animals per group, and data points significant different from Vehicle are marked with *.
Figure 3:
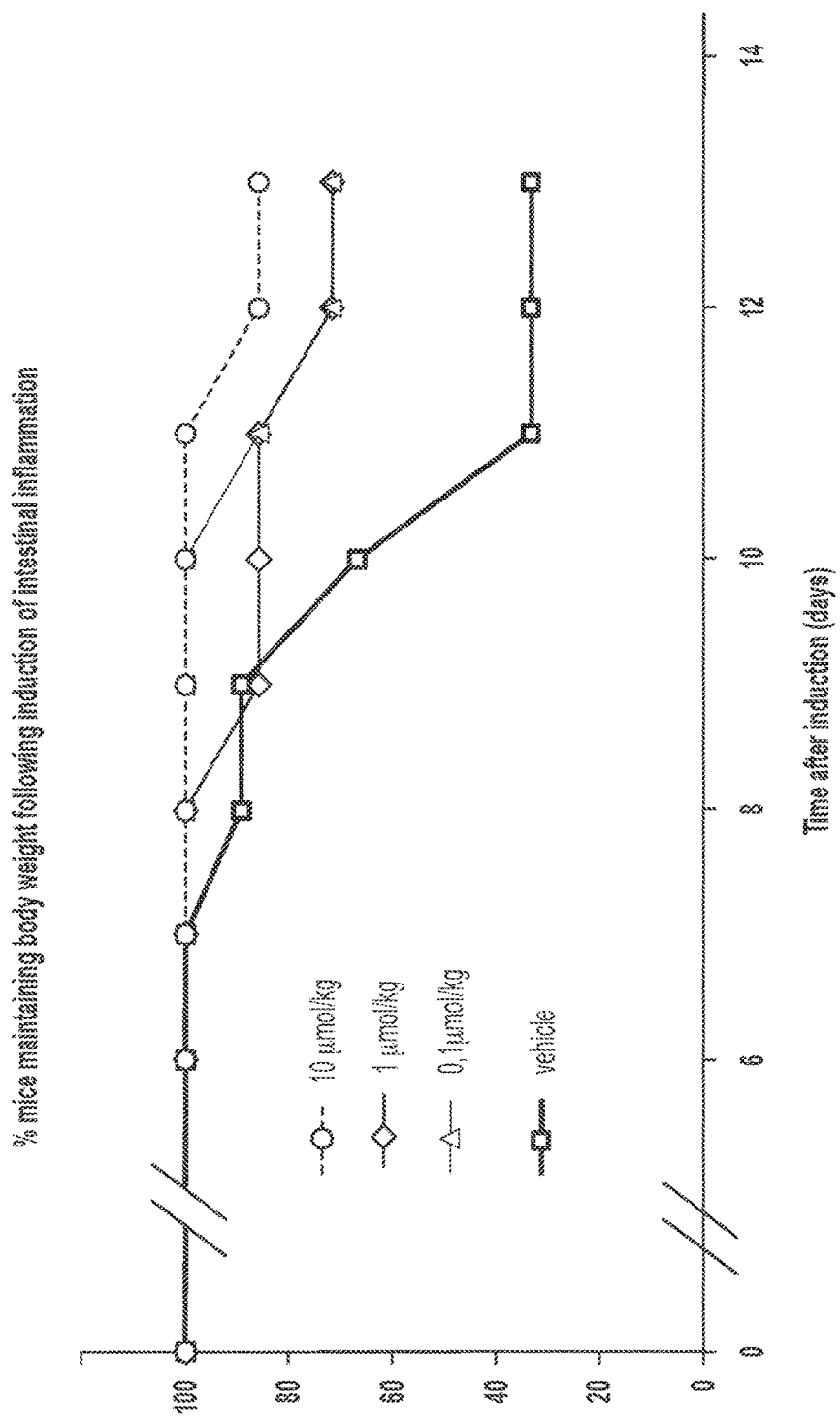
FIG. 3: Number of mice maintaining body weight in which intestinal inflammation has been induced using Dextran Sulfate. Mice were treated with Vehicle (1% citric acid in water, 5 mL/kg) or the indicated doses of compound E2 in µmol/kg.
Figure 4:
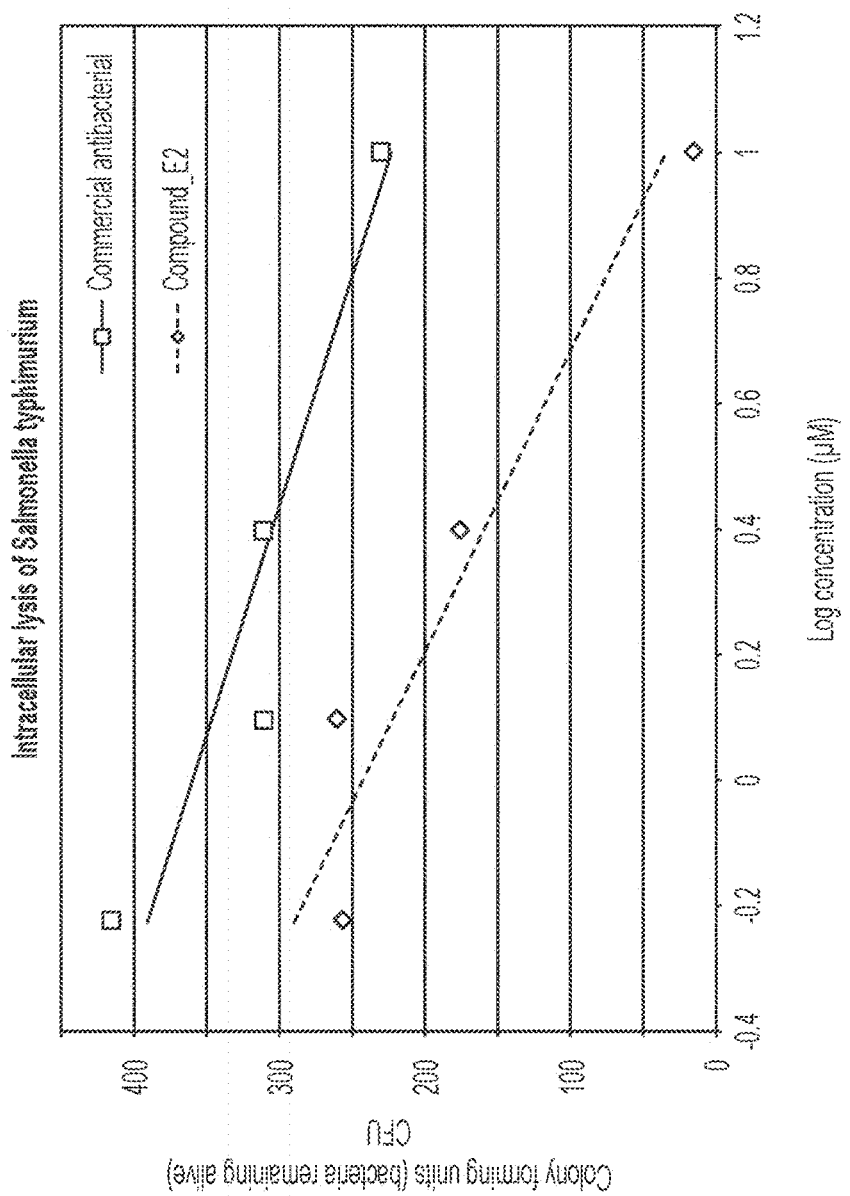
FIG. 4: Killing of phagocytosed *Salmonella typhimurium* by murine macrophages treated with either the commercial antibiotic azithromycin or Compound E2. Compound E2 stimulates the killing of bacterial cells by macrophages.
Figure 5:
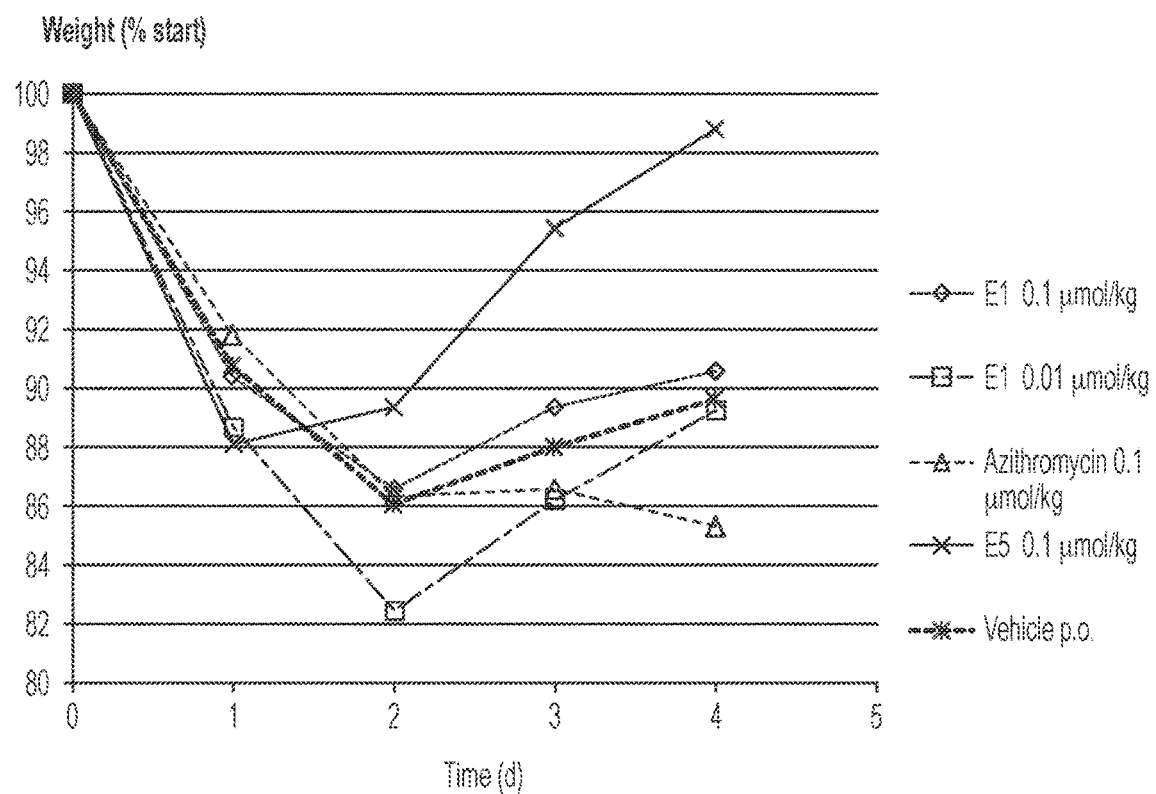
FIG. 5: Effect of substance E5 on the response of mice to an infection by *Staphylococcus*. Treatment with the substance E5 results in a faster recovery of weight due to faster clearance of bacteria
Figure 6:
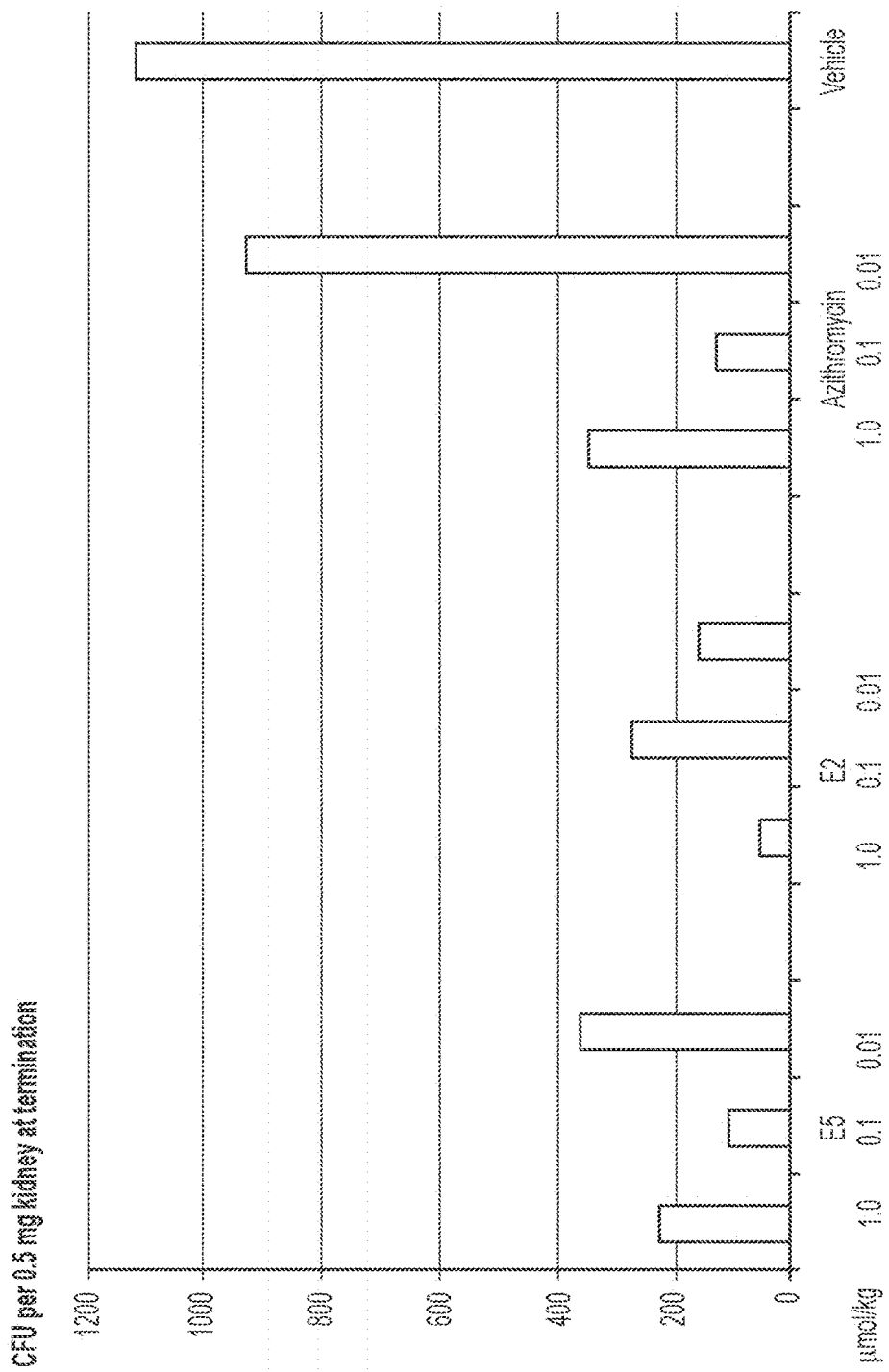
FIG. 6: Effect of substances E2, E5 and Azithromycin on the ability of mice to clear an infection by *Staphylococcus aureus* Newman. Bacteria are quantified as CFU recovered from a standard sample of kidney. Treatment with substances decreases recovered bacteria in a dose responsive manner.
Figure 7:
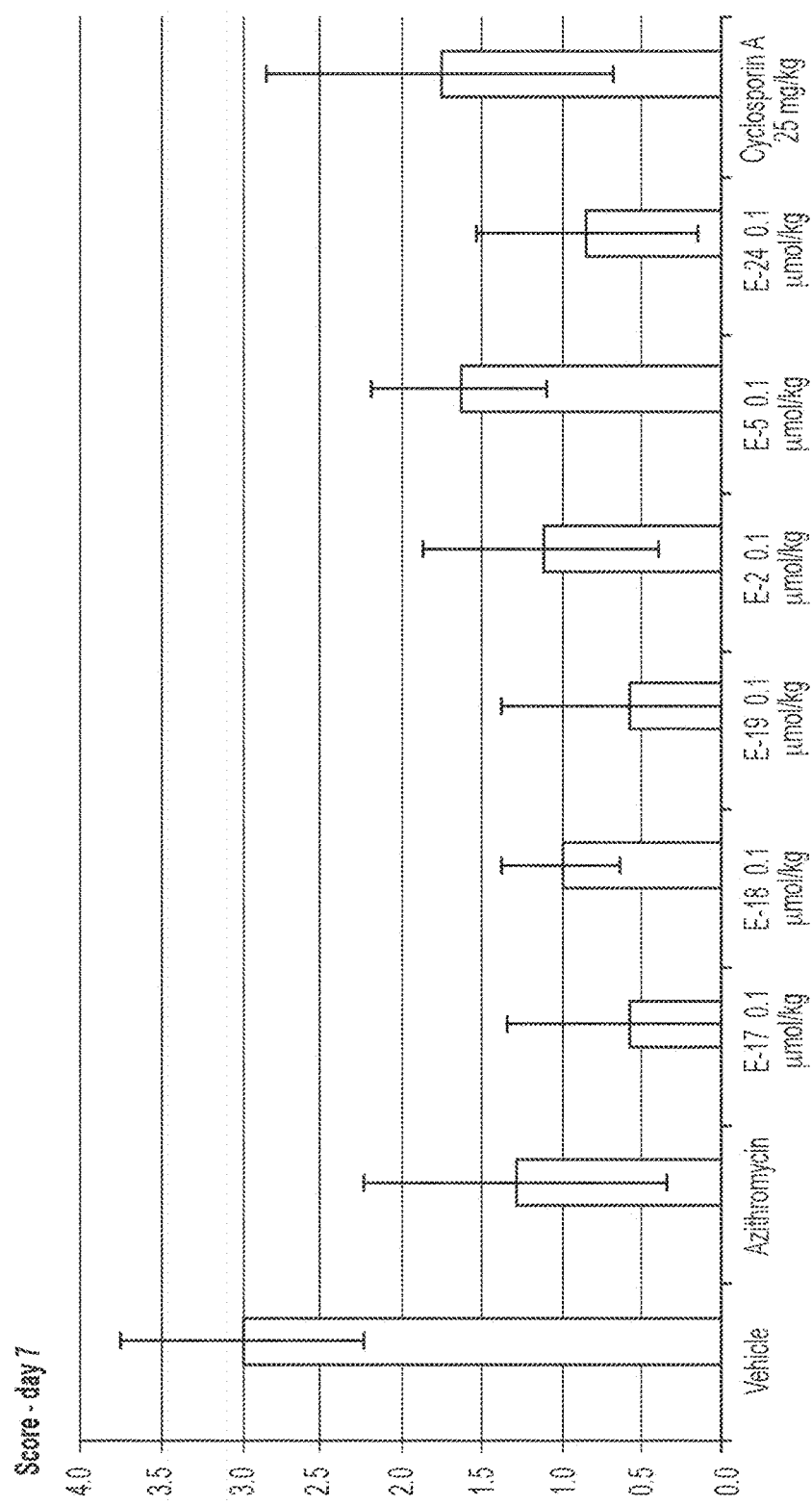
FIG. 7: Effect of substances on the ability of mice to tolerate dextran sulfate colitis. Cyclosporine is provided at a dose of 25 mg/kg, all other substances including azithromycin are provided at a dose of 0.1 mol/kg.
Figure 8:
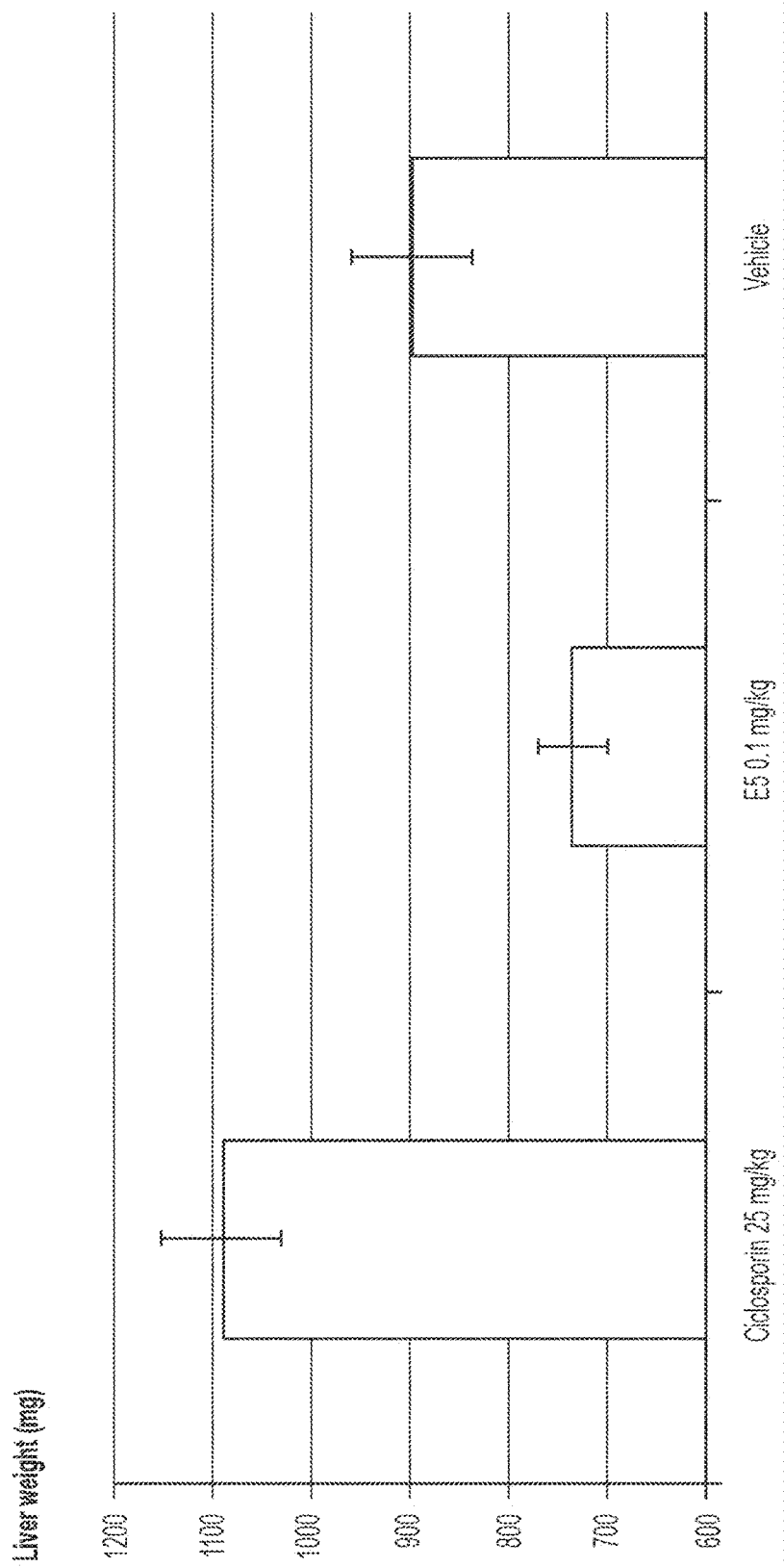
FIG. 8: Effect of substances E5 and Cyclosporin on the liver weight of mice treated with dextran sulfate colitis. Data are the mean of N=8 and are plotted with the 95% confidence interval.
Figure 9:
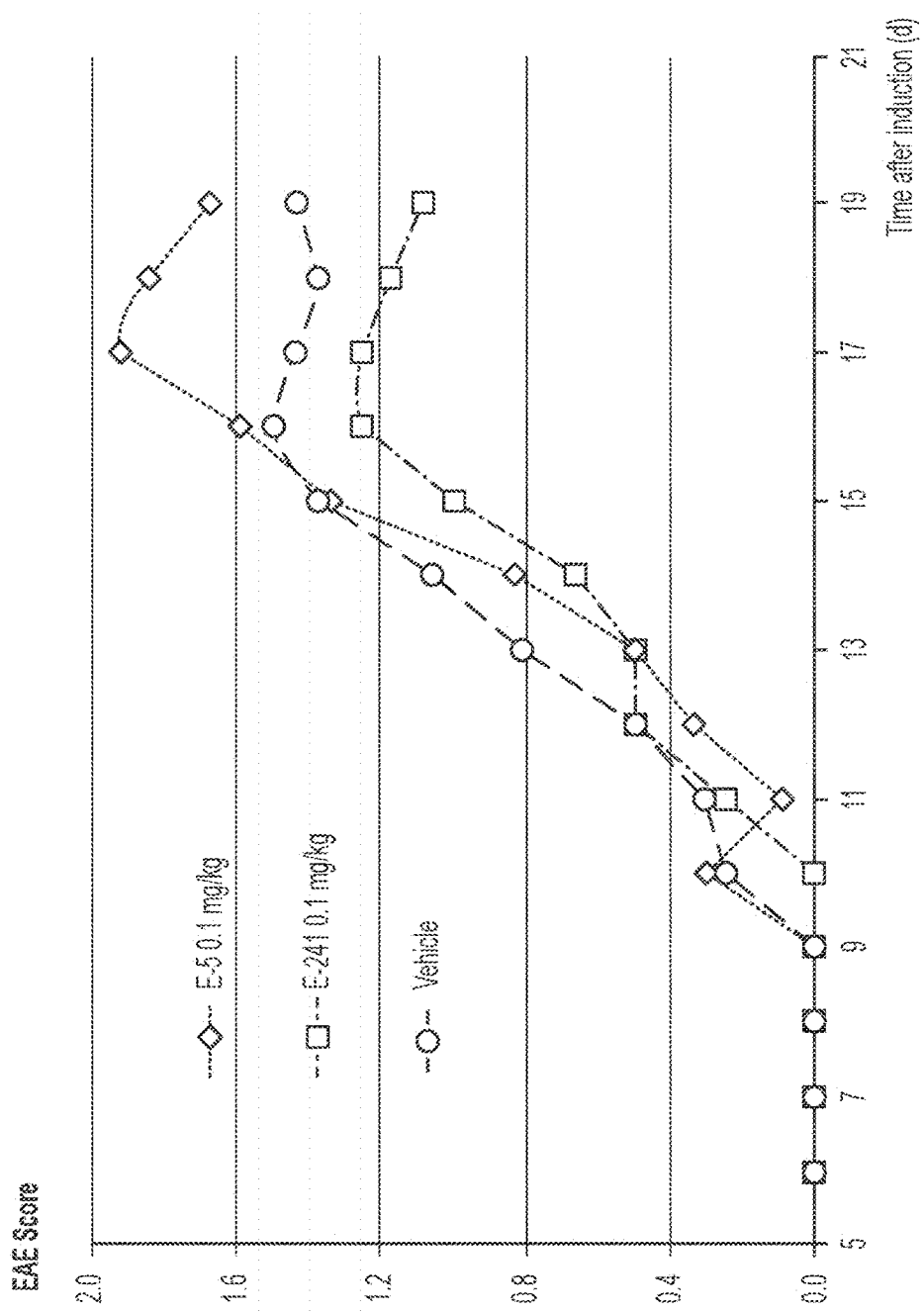
FIG. 9: Effect of substances E-5 and E-241 versus Vehicle on the development of EAE in the C57B6 mouse. Plotted is the clinical score based with antigen injected on day 0 and substance started on day 7. Data are the mean of N=8.
Figure 10:
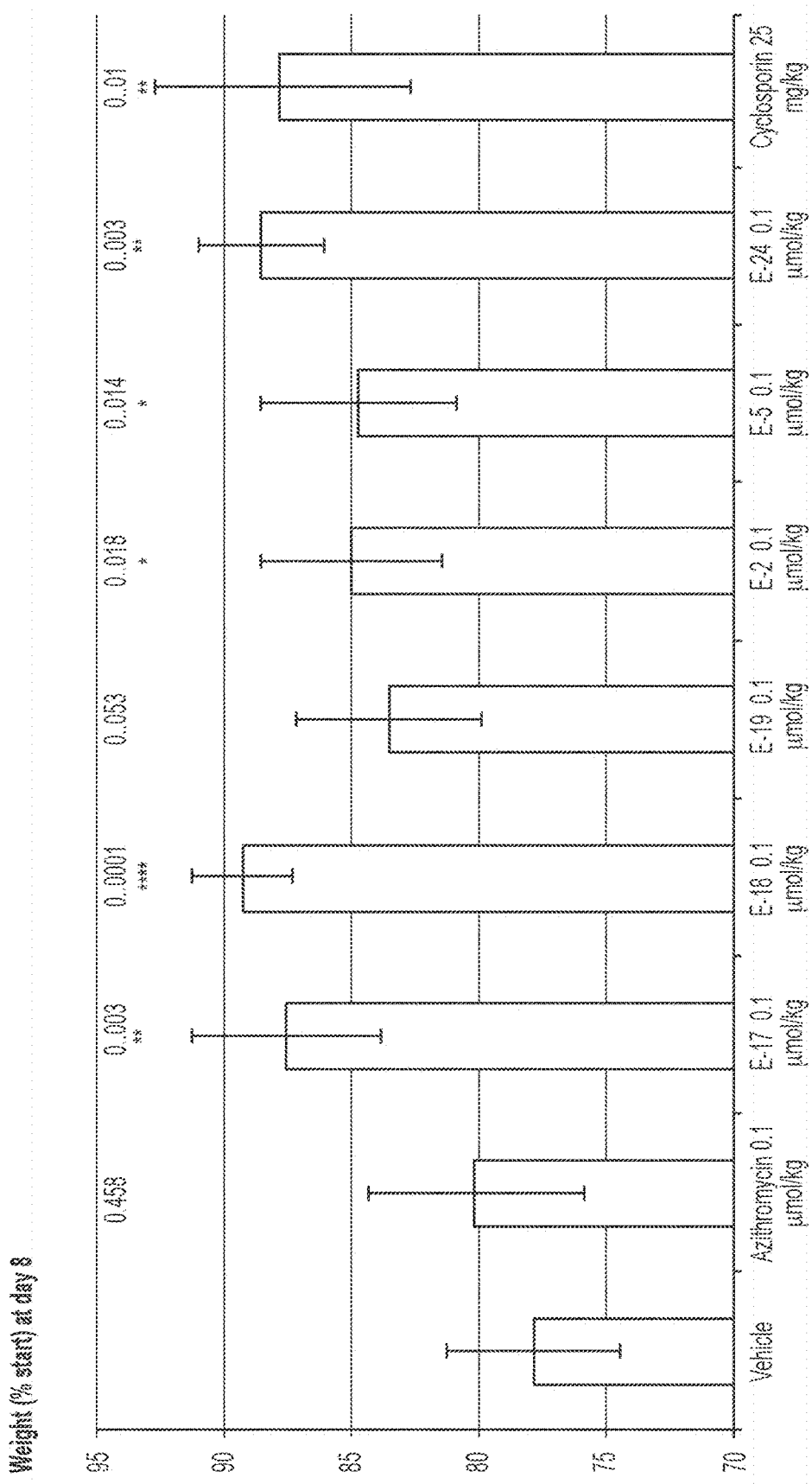
FIG. 10: Effect of substances compared with the positive control Cyclosporin on the body weight of mice treated with dextran sulfate colitis. Data are the mean of N=8 and are plotted with the 95% confidence interval. Above the bars are the p values vs. Vehicle for a T-test.
Figure 11:
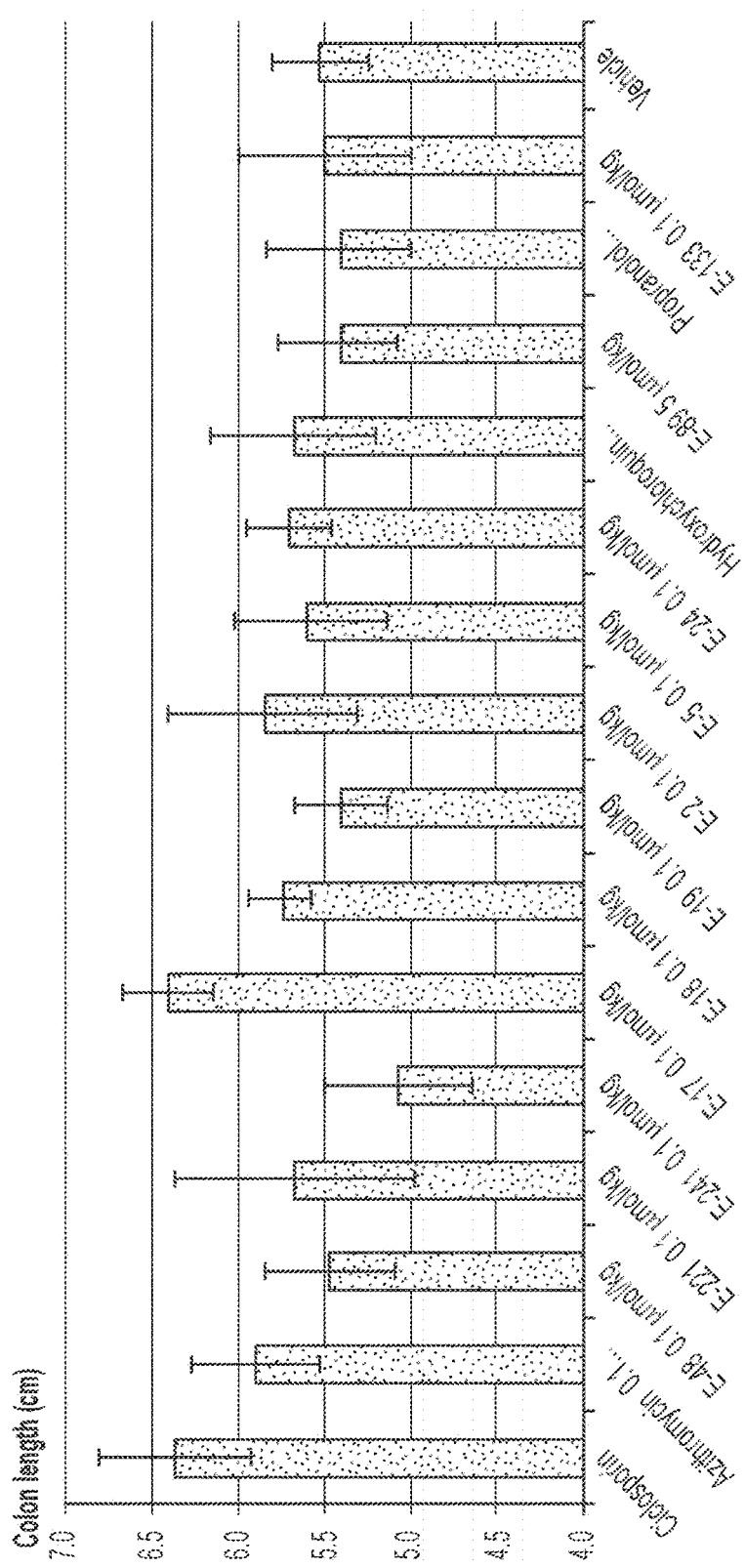
FIG. 11: Effect of substances compared with the positive control Cyclosporin on the colon length of mice treated with dextran sulfate colitis. Data are the mean of N=8 and are plotted with the 95% confidence interval. Above the bars are the p values vs. Vehicle for a T-test.
Figure 12:
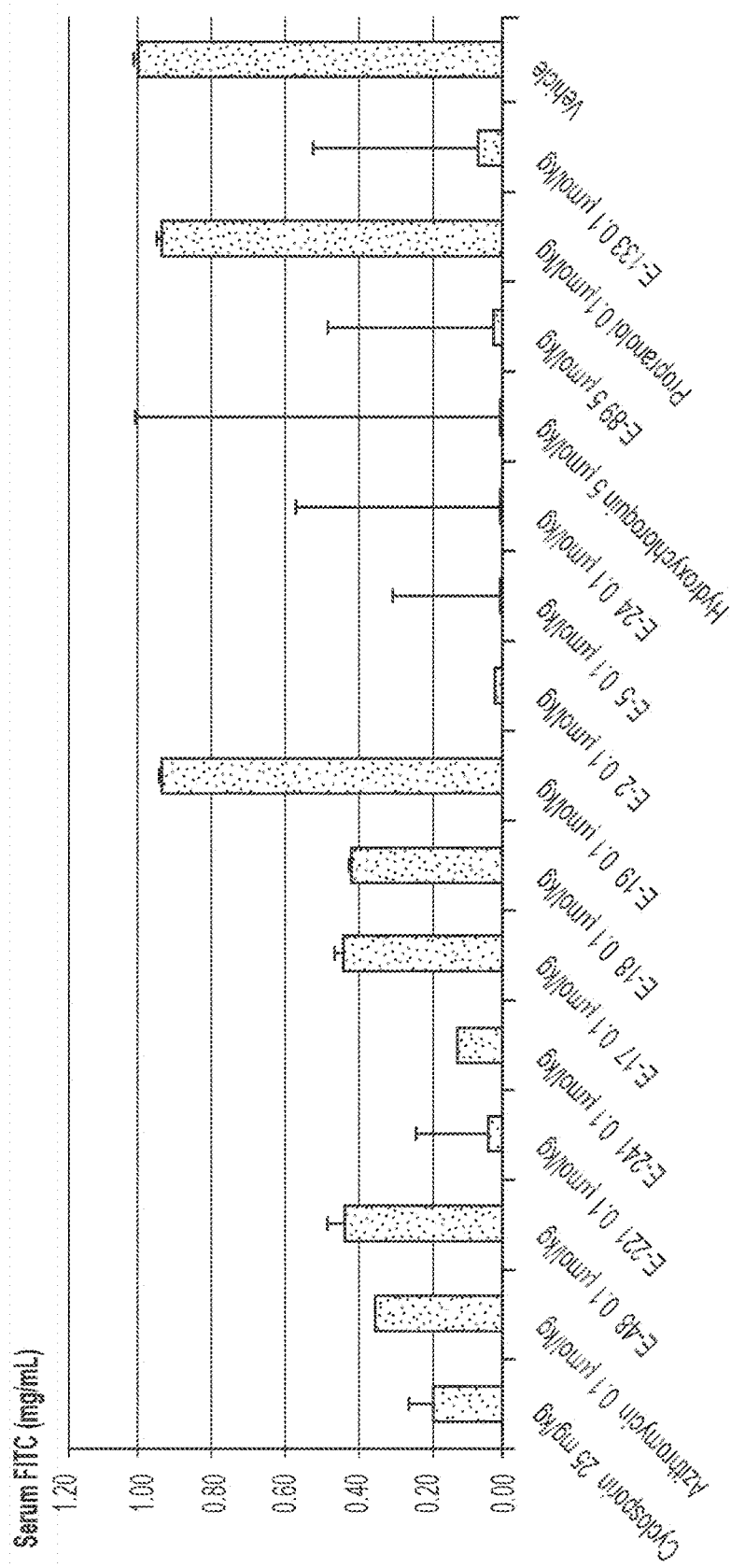
FIG. 12: Effect of substances compared with the positive control Cyclosporin on the amount of fluorocein labelled dextran (FITC) taken up into the serum of mice treated with dextran sulfate colitis. 4 h prior to sampling, mice are treated with an oral suspension of FITC dextran which would normally not enter the blood stream. The effect of DSS is to disrupt the gut epithelium allowing larger molecules to enter the blood stream. Reductions in FITC dextran suggest improved barrier function. Data are the mean of N=8 and are plotted with the 95% confidence interval. Above the bars are the p values vs. Vehicle for a T-test.
Figure 13:
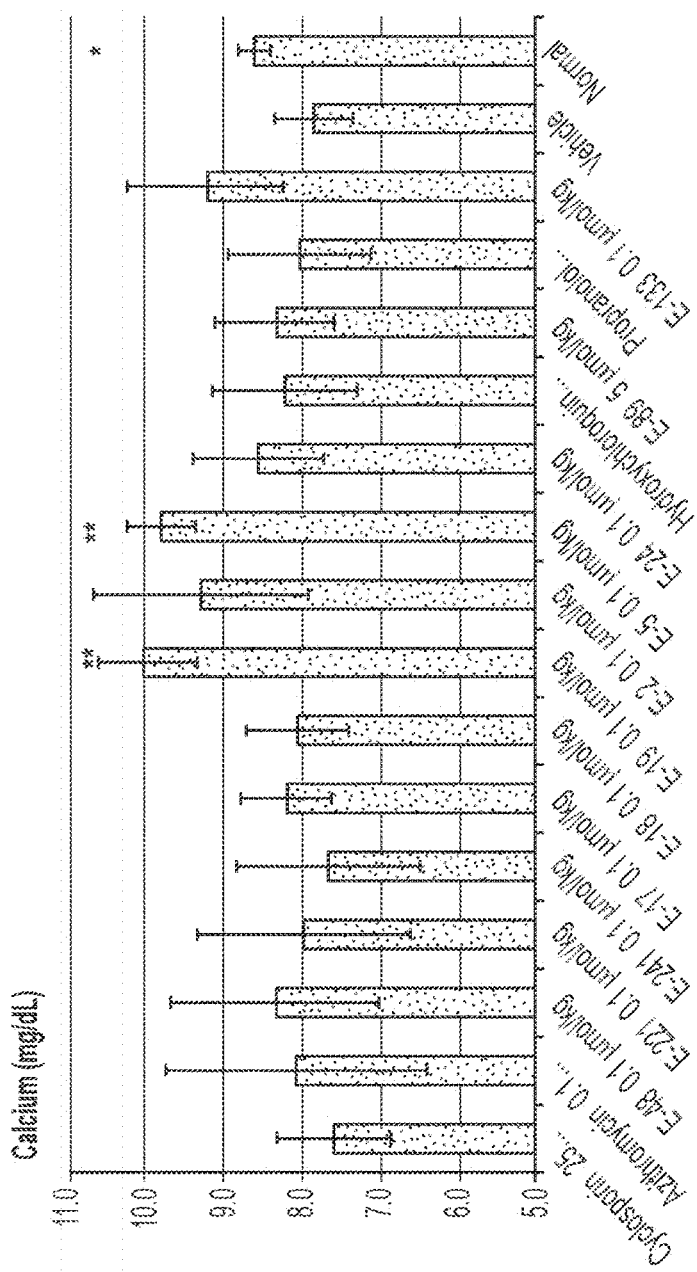
FIG. 13: Effect of substances compared with the positive control Cyclosporin on the serum Calcium of mice treated with dextran sulfate to induce colitis at day 8 after starting DSS. Data are the mean of N=8 and are plotted with the 95% confidence interval. Above the bars are the p values vs. Vehicle for a T-test.
Figure 14:
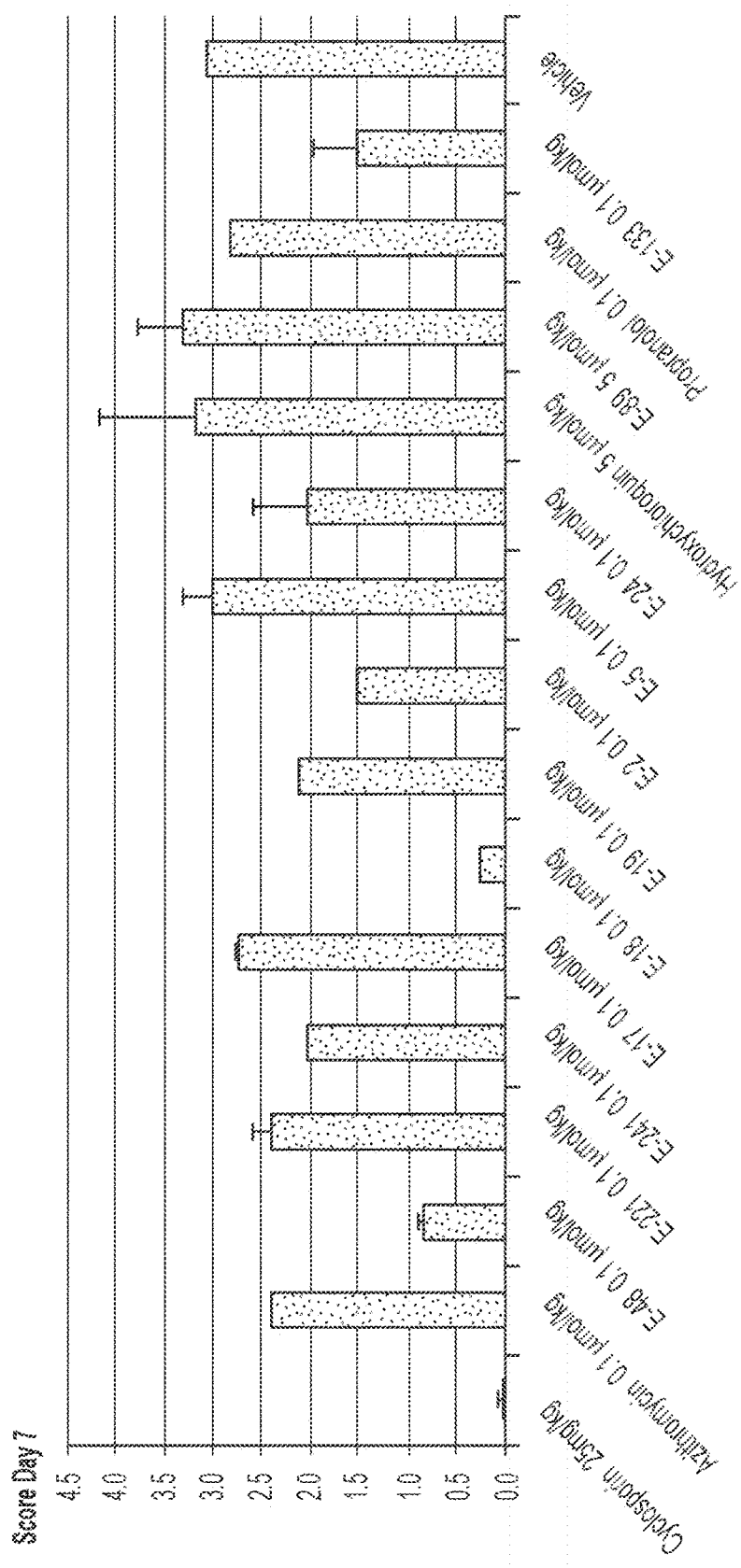
FIG. 14: Effect of substances compared with the positive control Cyclosporin on the clinical score of mice treated with dextran sulfate to induce colitis at day 8 after starting DSS. Data are the mean of N=8 and are plotted with the 95% confidence interval. Above the bars are the p values vs. Vehicle for a T-test.
Figure 15:
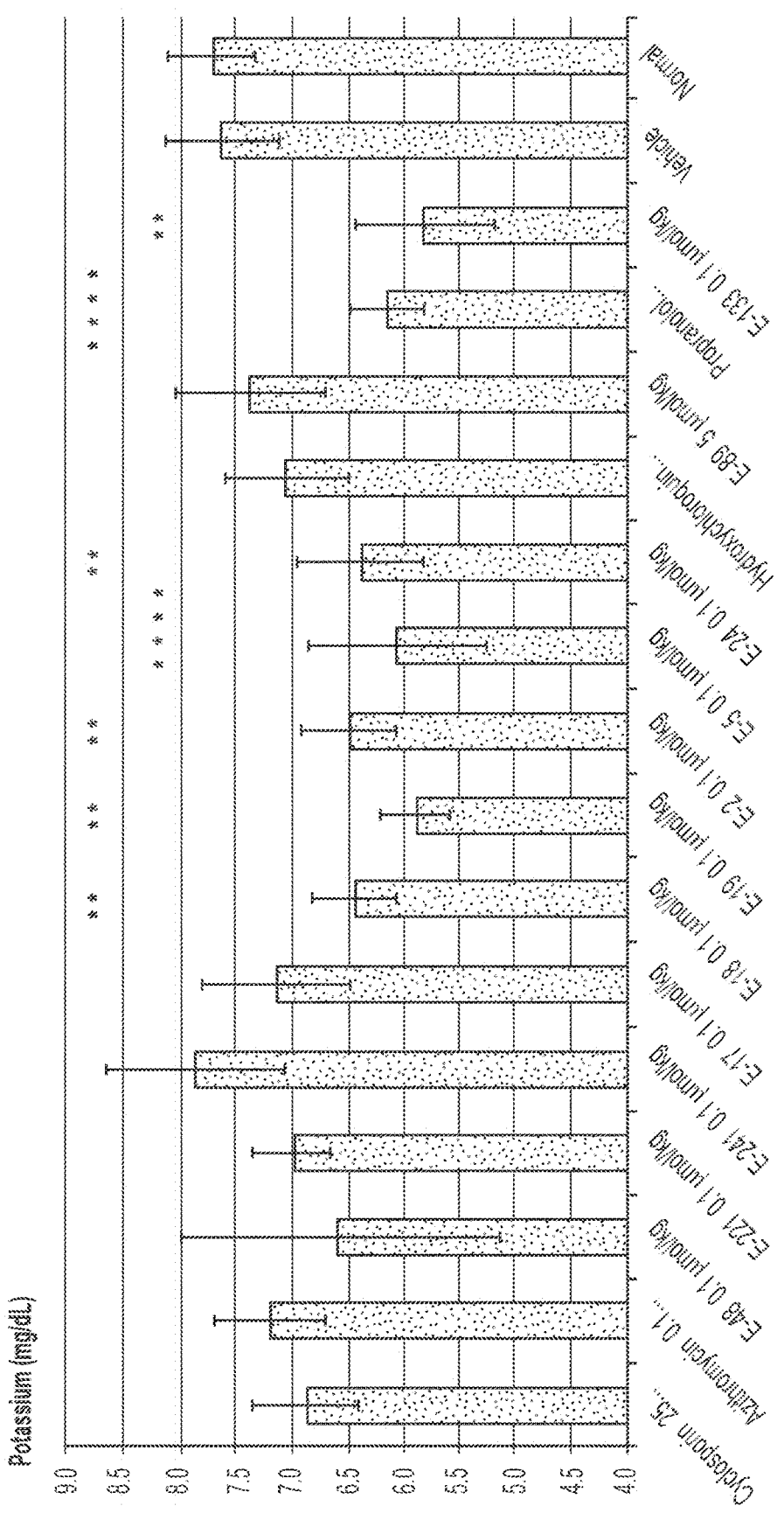
FIG. 15: Effect of substances compared with the positive control Cyclosporin on the serum Potassium of mice treated with dextran sulfate to induce colitis at day 8 after starting DSS. Data are the mean of N=8 and are plotted with the 95% confidence interval. Above the bars are the p values vs. Vehicle for a T-test.
Figure 16:
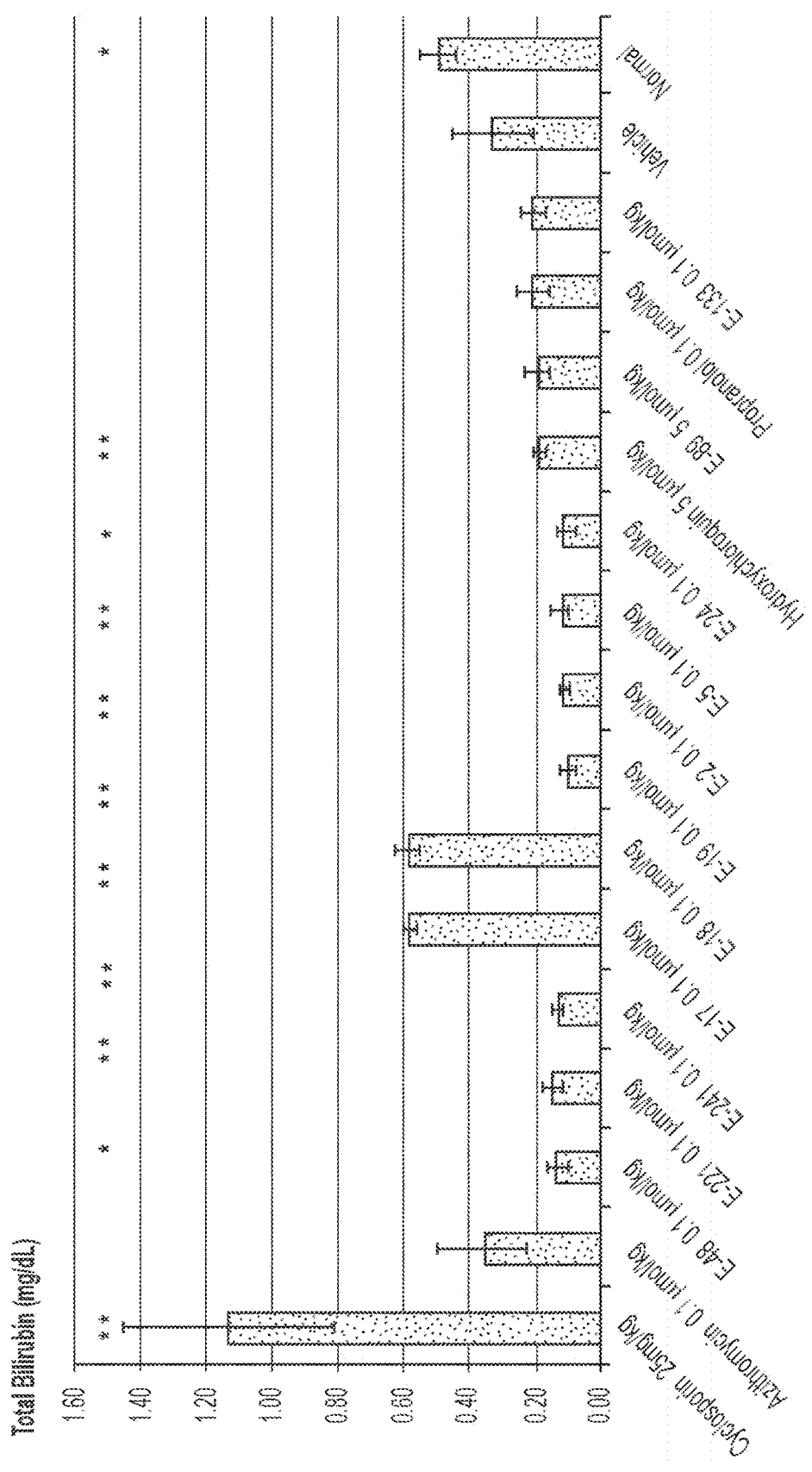
FIG. 16: Effect of substances compared with the positive control Cyclosporin on the serum Total Bilirubin of mice treated with dextran sulfate to induce colitis at day 8 after starting DSS. Data are the mean of N=8 and are plotted with the 95% confidence interval. Above the bars are the p values vs. Vehicle for a T-test.
Figure 17:
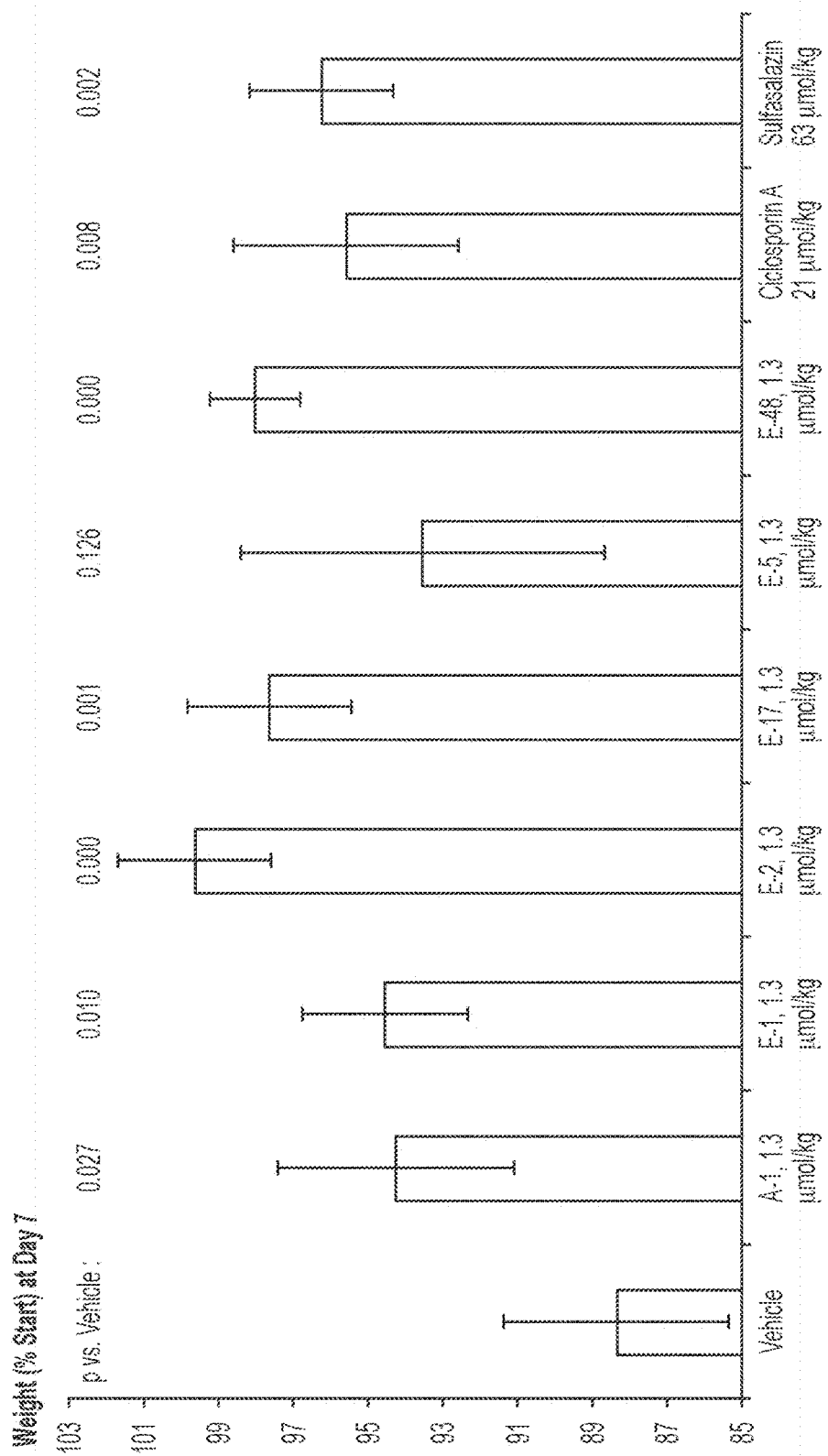
FIG. 17: Body weight of BALBc mice at day 7 after commencing 2.5% DSS in water. DSS causes lesions in the colon that lead to weight loss. Substance E-2, amongst others, protects against weight loss. Data are the mean of N=8 and are plotted with the 95% confidence interval.
Figure 18:
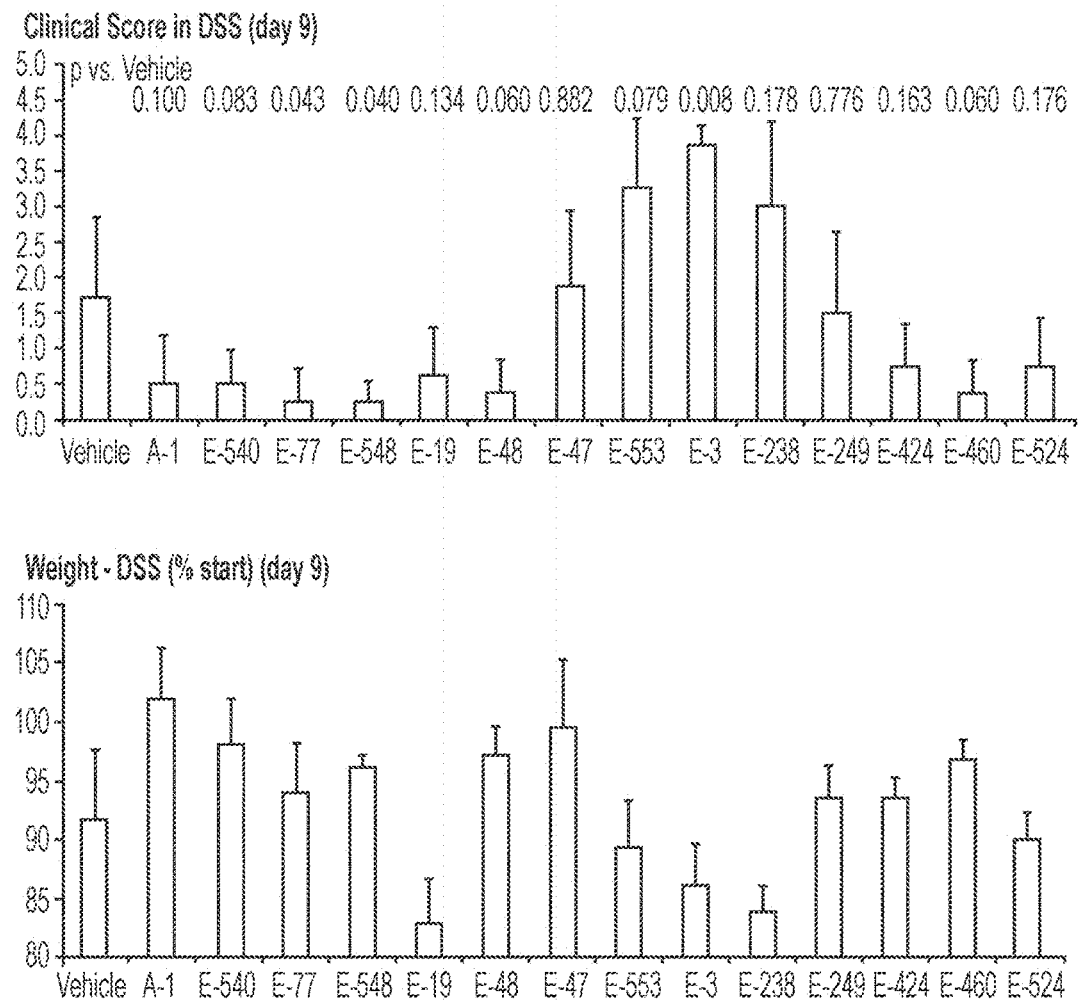
FIG. 18: Body weight and clinical score of BALBc mice at day 9 after commencing 2.5% DSS in water. DSS causes lesions in the colon that lead to weight loss. Substances E-3, E-238 and E-553, amongst others, stimulate inflammation. All doses 1.34 mol/kg. Data are the mean of N=8 and are plotted with the 95% confidence interval. Above the bars are the p values vs. Vehicle for a T-test.
Figure 19:
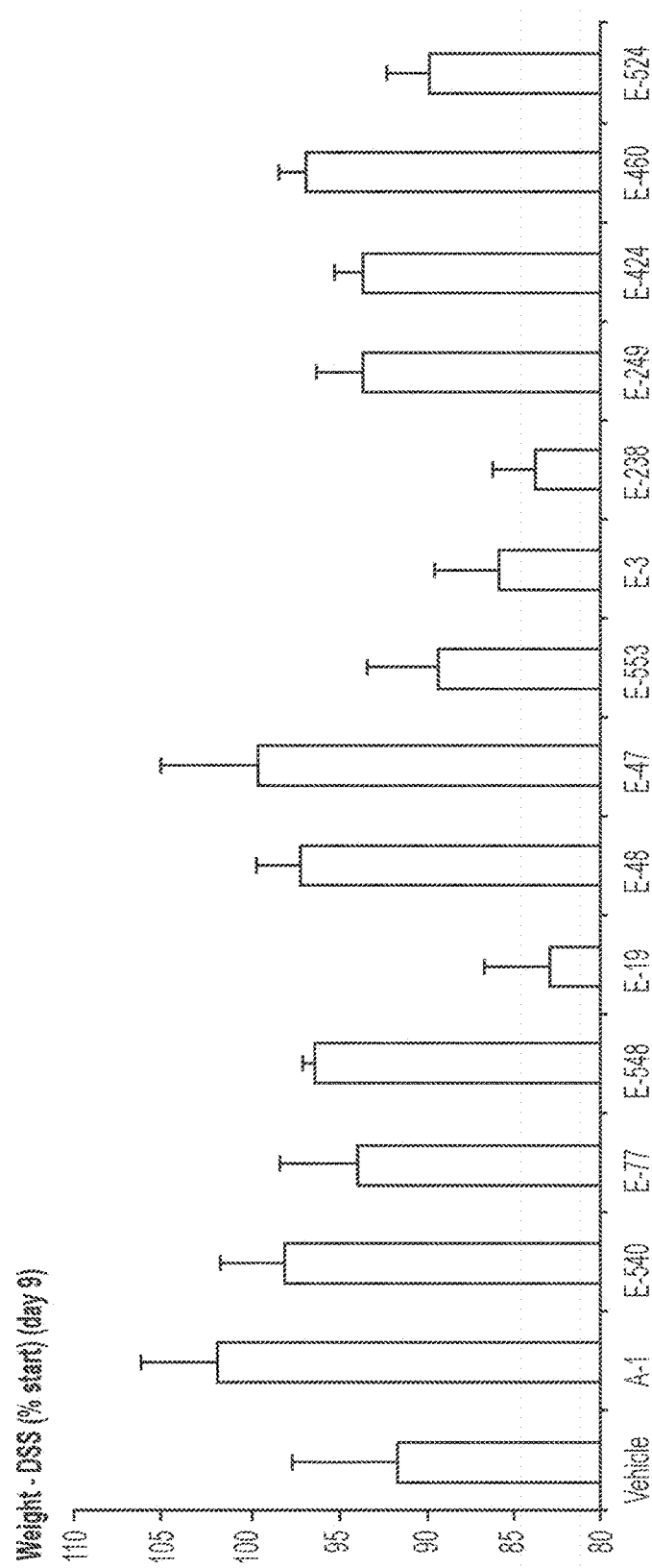
FIG. 19: Body weight and clinical score of BALBc mice at day 7 after commencing 2.5% DSS in water. DSS causes lesions in the colon that lead to weight loss. Substance like E-51 with weight greater than Vehicle protect against inflammation. Doses are as indicated. Data are the mean of N=8 and are plotted with the 95% confidence interval. Above the bars are the p values vs. Vehicle for a T-test.
Figure 19:
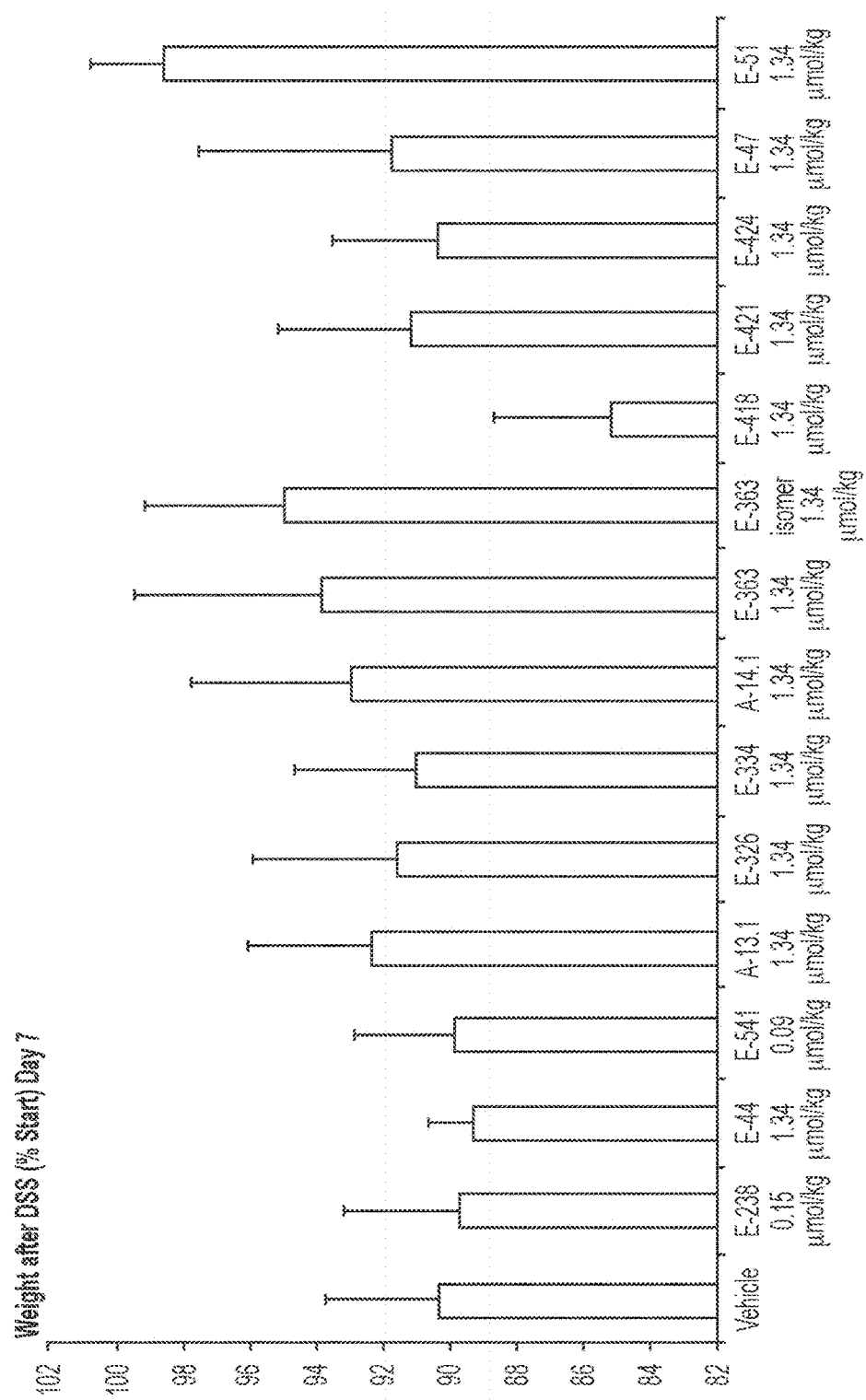
Figure 20:
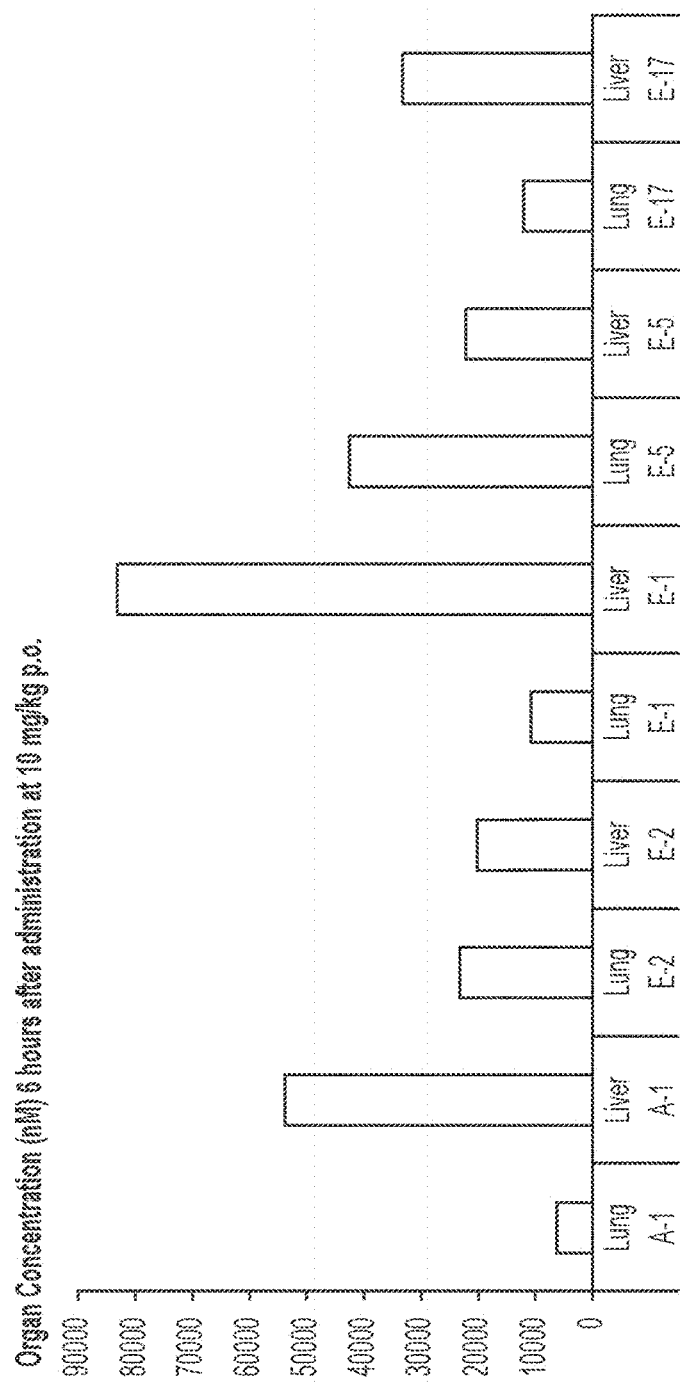
FIG. 20: The compounds containing $R_1$ nitrate ester have preferential distribution to the lung. Data show the concentration of the substance in the lung and liver at 6 h after administration of a 10 mg/kg dose p.o. in 2% citric acid.
Figure 21:
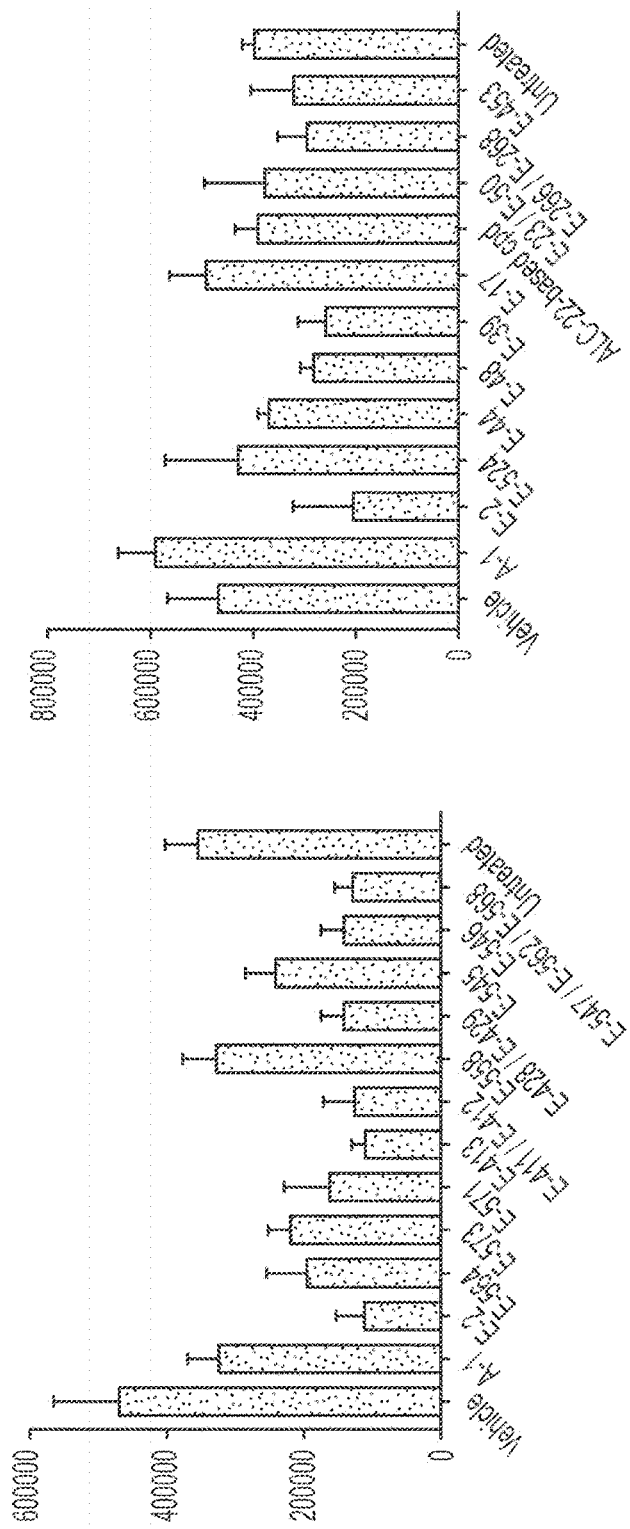
FIG. 21: The effect of various compounds on the rate of killing of *Salmonella typhimurium* following incubation and phagocytosis by J774 murine cells. The number of surviving bacteria is an indicator of the degree of intracellular killing of the bacteria, All substances are supplied at an initial concentration of 1 µM.

The potential efficacy of a Compound for rheumatoid arthritis may be modeled as follows. DBA1 mice are induced by a subcutaneous injection of bovine collagen in 0.05M acetic acid, emulsified in Freund's adjuvant. 21 days later, a second injection of this material is made without inclusion of mycobacterial material in the adjuvant. Animals are weighed and observed for signs of inflammation daily. Signs include weight loss, swelling of paws, redness and reduced mobility. Compound is formulated by mixing with a solution of 1% citric acid. Compound is provided by oral gavage daily. Data for the efficacy of compounds cited here is provided in FIG. 2.

Example 40

The potential efficacy of a Compound in modulating immune reactions may be determined as follows. Swiss or C57 Blk6 mice are induced to produce cytokines by a subcutaneous injection of lipopolysaccharide. Typically, compound is provided at time 0. Compound is formulated by mixing with a solution of 1% citric acid for oral treatment or, dissolved in PEG 300 and diluted in water for intra-peritoneal treatment. Compound is provided by oral gavage. 30 minutes after providing compound, animals are treated with an intra-peritoneal injection of a solution of lipopolysaccharide in the concentration range that will provide 0.01 mg/kg lipopolysaccharide. Data for the efficacy of compounds cited here is provided in FIG. 1.

Example 41

The potential efficacy of a Compound in treating a malignant disease may be determined as follows. Tumours are known to be deficient in nitric oxide and this is considered to be a cause of local tolerance. Providing a nitric oxide donor that is accumulated in macrophages in the tumour environment provides a means to artificially modify the local NO status. C57 Blk6 mice are injected subcutaneously with an murine ovarian cancer cell line expressing ovalbumin. Mice bearing tumours are selected after 14 days. Typically, compound is provided at this time. Compound is formulated by mixing with a solution of 1% citric acid for oral treatment. Compound is provided by oral gavage. Animals are monitored daily for tumour size, body weight and activity score. The activity of the compound may be determined in combination with other therapies including anti-bodies or vaccines based on a tumour antigen. In this case ovalbumin, can serve as a model antigen.

Example 42

Synthesis of 2'-O-(2-Ferrocenyl) acetyl-11-O-nitro-azithromycin

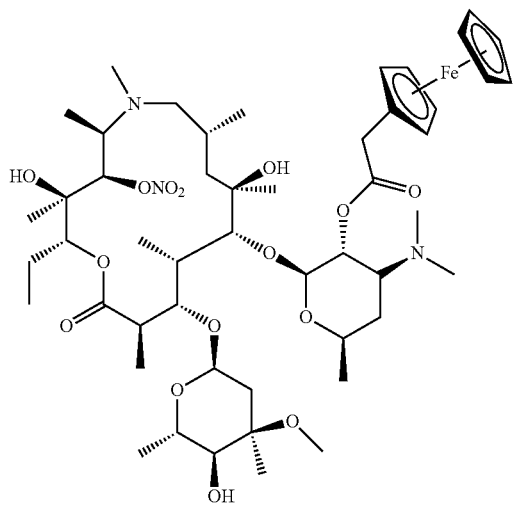

11-O-Nitro-azithromycin (0.25 mmol) was dissolved in dry dichloromethane (5 mL). To this was added EDCI (2 eq., 0.5 mmol) and 2-ferrocenyl acetic acid (1.1 eq., 0.28 mmol). The reaction was stirred overnight at room temperature. The solvent was removed in vacuo and the resulting white amorphous foam. The resulting crude product was purified by column chromatography with a gradient starting at 10% of acetone in cyclohexane (0.2% Et$_3$N).

Similarly, the following compound may be obtained using the procedure above starting from 2'-O-Nitro-azithromycin:

2'-O-Nitro-11-O-(2-ferrocenyl) acetyl-azithromycin

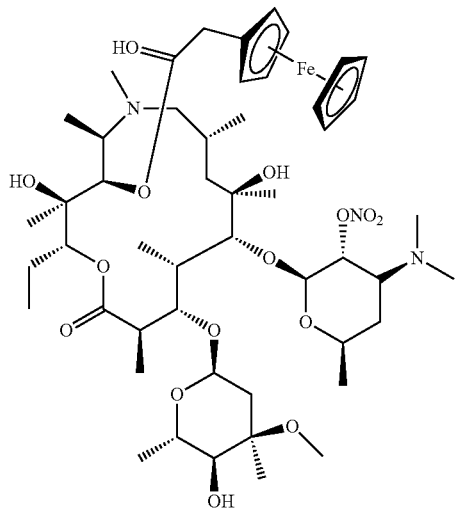

Example 43. rac. 2'-O-Propionyl Propranolol

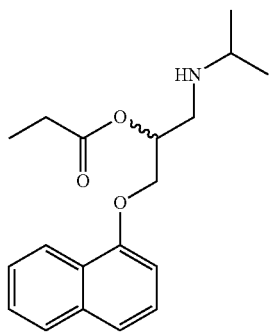 [SMILES: CCC(=O)OC(CNC(C)C)COc1cccc2ccccc12]

Diethyl azodicarboxylat (DEAD, 10 mmol) is added to a stirred (magnetic stirrer, 300 rpm) solution of triphenylphosphin (10 mmol) in dry THF (25 mL) at 0° C. and treatment is continued for 30 min. Propranolol (5 mmol) and propionic acid (10 mmol) both dissolved in THF (10 mL) are added dropwise and stirring is continued for 1 h at 0° C. and further 2 hours at ambient temperature. Any precipitates are filtered off, the remaining solution is concentrated in vacuo and desired product is isolated by column chromatography (silica gel, cyclohexane-ethyl acetate).

Example 44. rac. 2'-O-Acetoxypropionyl Propranolol

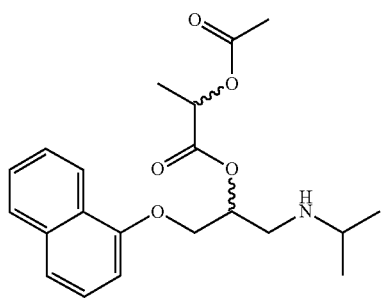 [SMILES: CC(=O)OC(C)C(=O)OC(CNC(C)C)COc1cccc2ccccc12]

Diethyl azodicarboxylate (DEAD, 10 mmol) is added to a stirred (magnetic stirrer, 300 rpm) solution of triphenylphosphin (10 mmol) in dry THF (25 mL) at 0° C. and treatment is continued for 30 min. Propranolol (5 mmol) and 2-acetoxypropionic acid (10 mmol) both dissolved in THF (10 mL) are added dropwise and stirring is continued for 1 h at 0° C. and further 2 hours at ambient temperature. Any precipitates are filtered off, the remaining solution is concentrated in vacuo and desired product is isolated by column chromatography (silica gel, cyclohexane-ethyl acetate).

Example 45 Synthesis of Azithromycin 11,2'-dilapidate

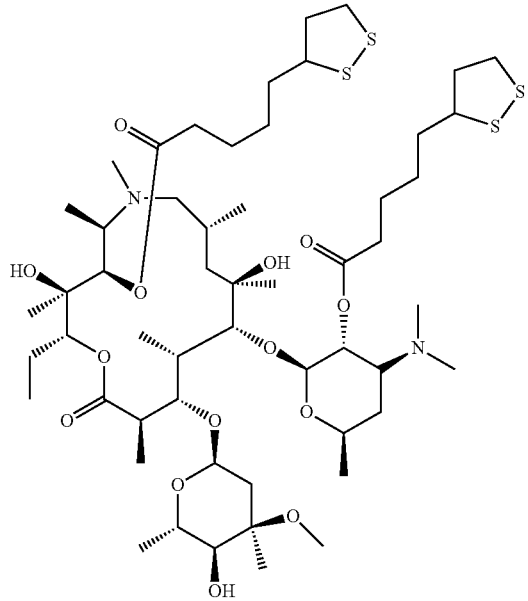

380 mg of azithromycin-2'-lipoate (E-77) are dissolved in 25 ml of dichloromethane and cooled in an ice bath. 125 mg of lipoyl are added, then 50 µl of pyridine. The mixture is allowed to reach room temperature and stirred for 16 h. The reaction mixture is extracted with water 3 times, then once with 5% aqueous citric acid. The citric acid phase is extracted with dichloromethane, then combined with ethyl acetate and carefully made basic with sodium hydrogen carbonate and vigorous stirring. When gas evolution ceases, the organic phase is separated, washed with water and brine, and dried with sodium sulfate. After evaporation of all volatiles, the residue is chromatographed with a gradient starting at cyclohexane-acetone 5-1, containing 0.5% of triethylamine. Yield: 140 mg

Example 46 Synthesis of Azithromycin 11-lipoate

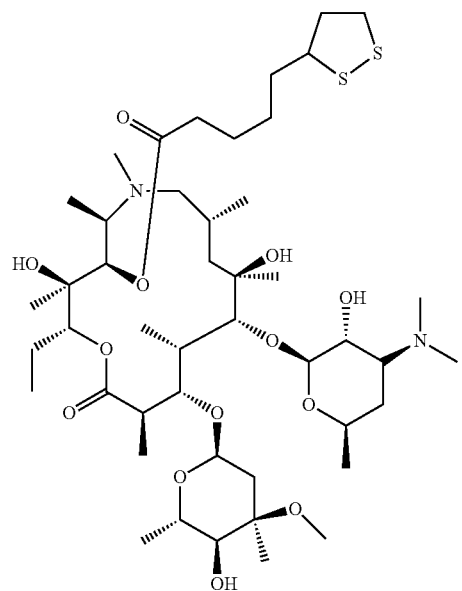

350 mg of Azithromycin 11,2'-dilipoate are stirred with 5 ml methanol at room temperature. When mass spectrometry indicates completion of the reaction (m/z=1125.5->937.5), the mixture is partitioned between water and ethyl acetate. The organic phase is washed once with water, then extracted with 5% aqueous citric acid. The citric acid phase is extracted with dichloromethane, then combined with ethyl acetate and carefully made basic with sodium hydrogen carbonate and vigorous stirring. When gas evolution ceases, the organic phase is separated, washed with water and brine, and dried with sodium sulfate. After evaporation of all volatiles, the residue is chromatographed with a gradient starting at cyclohexane-acetone 5-1, containing 0.5% of triethylamine. Yield: 225 mg Example 47. Formation of Acetic Esters of ALCs Method 1:

ALC (1.0 mmol) was taken up in 15 mL dichloromethane. Pyridine (1.2 eq.) was added and the resulting solution was cooled in an ice bath for approximately 10 minutes. At this point, a solution of acetic anhydride (1.2 eq) was added dropwise. The reaction was stirred continually at this temperature and then progressively warmed to room temperature where it was stirred overnight. Reaction progress was monitored either by TLC and/or MS. The reaction was washed with a saturated solution of ammonium chloride (3×), water (3×) and dried over anhydrous $Na_2SO_4$. The solvent was evaporated in vacuo. Co-evaporation with toluene is necessary to remove residual pyridine from the system. This was followed by re-dissolving the residue in DCM and solvent evaporation twice to produce a white foam, which was dried under high-vacuum to produce acetylated product.

This acetylation conditions can be extended for other ALCs. In the case where the acetylation proceeds sluggish, alternative reaction conditions were undertaken as described below:

Method 2.

Compound A-12 (0.85 mmol) was taken up in DCM (10 mL). To this was added triethylamine (3.5 eq) and acetyl chloride (3.5 eq). Reaction was monitored by TLC and MS until disappearance of starting ALC. Reaction was filtered. The filtrate was either evaporated in vacuo and directly purified by column chromatography or the filtrate was washed with 10% aq. $Na_2CO_3$ solution, brine, dried over $Na_2SO_4$ and evaporated in vacuo to get the crude product.

Method 3.

Acetic acid (4 eq) was taken up in 5 mL dichloromethane (DCM). Compound A-16 (0.5 mmol) and 4-dimethylaminopyridine (DMAP) (4.4 eq) were added and the resulting solution was cooled in an ice bath for approximately 10 minutes. At this point, dicyclohexylcarbodiimide (DCC) (4.4 eq) was added slowly. The reaction was stirred continually at this temperature for 5 minutes and then progressively warmed to room temperature where it was stirred overnight. Dicyclohexylurea (DCU) that was formed during the reaction is filtered off and discarded. The filtrate was collected and then washed with a saturated solution of sodium hydrogencarbonate (3×), water (1×) and dried over anhydrous $Na_2SO_4$. The solvent was evaporated in vacuo. This was followed by re-dissolving the residue in a small volume of methanol. The solution was transported dropwise into ice-cold water (2× volume of methanol) and stored in the freezer overnight. The precipitated product was filtered off and dried under high-vacuum to produce a product.

TABLE 14

Acetylation Examples

| Compound Entry | Synthesis Method | ALC | Substituent equivalent | Reaction Condition (i.e. Workup) | Degree of Substitution | Yield | MS m/z ([M + H]$^+$) |
|---|---|---|---|---|---|---|---|
| E-2 | 1 | A-1 | 1.2 | as described above | 1 | 76% | 837 |
| E-4 | 1 | A-1 | 1.5 | as described above | 1 | 41% | |
| E-8 | 1 | A-1 | 1.2 | | | 39% | |
| E-23 | 1 | A-1 | 2.0 | as described above | 2 | 54% | |
| E-25 | 1 | A-1 | 1.1 | as described above | 1 | 67% | |
| E-418 | 3 | A-16 | 4 | as described above | 3 | 20% | CHMA02063 |
| E-228 | 1 | A-10 | 4 | as described above | 2 | 56% | 673 |
| E-453 | A-17 | Overall 12 equiv. Ac$_2$O | | 1 and 2 | 49% (referring to the di-ester) | 819.7 861.5 | A-17 |
| E-266/ E-268 | 2 | A-12 | 3 | as described above, filtered through a silica gel plug using CHCl$_3$:iPrOH:7M NH$_3$ in MeOH (30:1:1) as mobile phase | 2 > 4 | 77% | 675, 759 |
| E-23/E-50 | | A-1 | | | 2 and 3 | 16% | 833, 875 |
| E-564 | 1 | A-2 (X = O) | | | 1 | 89% | 776 |
| E-29 | 1 | E-19 | 1.2 | direct chromatography for purification | 1× | 85% | 861 |

Example 48. Formation of Butyric and Isobutyric Esters of ALCs

Method 1:
Compound A-1 was taken up in dichloromethane and stirred for 10 min. At this point, a solution of carboxylic anhydride and triethylamine in dichloromethane was added dropwise. The reaction was stirred continually at room temperature. The reaction solution was washed with 5% citric acid three times to extract the product. Acidic solution was then washed with ethyl acetate (2x) and afterwards neutralized with $Na_2CO_3$. Product was extracted with ethyl acetate (3x). The solution was washed with a saturated solution of sodium chloride (2x), water (2x) and dried over anhydrous $Na_2SO_4$. The solvent was evaporated in vacuo to produce a white foam containing product.

Method 2:
Compound A-1 was taken up in dichloromethane and was cooled in an ice bath for approximately 10 minutes. At this point, a solution of carboxylic chloride in dichloromethane was added dropwise. The reaction was stirred continually at this temperature for 15 min and then progressively warmed to room temperature where it was stirred for 2.5 h.
The reaction was washed with a 10% solution of $Na_2CO_3$ (3x), water (3x) and dried over anhydrous $Na_2SO_4$. The solvent was evaporated in vacuo. Co-evaporation with toluene is necessary three times. This was followed by re-dissolving the residue in dichloromethane to produce a white foam, which was dried under high-vacuum to produce product.

Method 3:
Starting material was taken up in dichloromethane and stirred for 10 min. At this point, a solution of carboxylic chloride and triethylamine in dichloromethane was added dropwise. The reaction was stirred continually at room temperature for two days. The reaction solution was washed with 5% citric acid three times to extract the product. Acidic solution was then washed with ethyl acetate (2x) and afterwards neutralized with $Na_2CO_3$. Product was extracted with ethyl acetate (3x). The solution was washed with a saturated solution of sodium chloride (2x), water (2x) and dried over anhydrous $Na_2SO_4$. The solvent was evaporated in vacuo to produce a white foam containing product.

Method 4:
Compound E-48 or E-39 was solved in methanol to hydrolyze butyric esters. The reaction was stirred continually at room temperature for two days. The reaction solution was washed with ethyl acetate three times to extract the product. The ethyl acetate phase was washed with 5% citric acid (3x). Acidic solution was then washed with ethyl acetate (2x) and afterwards neutralized with $Na_2CO_3$. Product was extracted with ethyl acetate (3x). The solution was washed with a saturated solution of sodium chloride (2x), water (2x) and dried over anhydrous $Na_2SO_4$. The solvent was evaporated in vacuo to produce a white foam containing product.

Method 5:
Carboxylic acid (180 mg, 2.04 mmol) was solved in 3 mL dichloromethane. Under stirring conditions 4-Dimethylaminopyridine (274 mg, 2.24 mmol) and A-16 were added. The reaction solution was cooled to 0° C. and N,N'-Dicyclohexylcarbodiimide (463 mg, 2.24 mmol) was added. The reaction was stirred continually at this temperature for 5 min and then progressively warmed to room temperature where it was stirred for 12 h. Precipitation was removed via filtration. The reaction was washed with a saturated solution of $NaHCO_3$ (3x) and dried over anhydrous $Na_2SO_4$. The solvent was evaporated in vacuo. Product was solved in methanol and water was added. Solution was cooled to −20° C., a precipitation occurred which was extracted and dried in vacuo.

Workup 1:
Column chromatography over silica gel was carried out to separate different products. As eluent a mixture of chloroform, 2-propanol and ammonia in methanol (60:1:1) was used. The solvent was evaporated in vacuo.

Workup 2:
Preparative chromatography over RP-C18-silica gel was carried out to separate different products. As eluent a mixture of water (with trifluoroacetic acid 0.05%) and methanol (with trifluoroacetic acid 0.05%) was used. The solvent was evaporated in vacuo.

Workup 3:
Column chromatography over silica gel was carried out to separate different products. As eluent a mixture of cyclohexane, acetone (7:1) with 0.5% triethylamine was used. The solvent was evaporated in vacuo.

TABLE 15

Butyrylation/Isobutyrylation Examples

| Compound Entry | Synthesis Method | ALC | Substituent | Reaction Condition (i.e. Workup) | Degree of Substitution | Yield | MS |
| --- | --- | --- | --- | --- | --- | --- | --- |
| E-35 | 1 | A-1 | Butyric | Workup 1 | 1x | 76% | 819 |
| E-39 | 3 | A-1 | Butyric | Workup 2 | 2x | 10% | 889 |
| E-48 | 3 | A-1 | Butyric | Workup 2 | 3x | 12% | 959 |
| E-47 | 3 | A-1 | Butyric | Workup 2 | 4x | 10% | 1029 |
| E-424 | 5 | A-16 | Butyric | none | 3x | 97% | 944 |
| E-458 | 2 | A-17 | Butyric | none | 1x | 89% | 847 |
| E-19 | 4 | E-39 | Butyric | Workup 2 | 1x | 85% | 819 |
| E-82 | 4 | E-48 | Butyric | Workup 3 | 1x | 35% | 819 |
| E-553 | 4 | E-48 | Butyric | Workup 3 | 2x | 30% | 889 |
| E-44 | 1 | A-1 | Isobutyric | Workup 1 | 1x | 67% | 819 |
| E-458, E-459, E-460 | 3 | A-17 | Butyric | Workup 1 | 1x, 2x, 3x | 86% | 847, 917, 987 |
| E-238 | 1 | A-10 | Butyric | none | 1x | 96% | 659 |
| E-241, E-249, E-250 | 3 | A-10 | Butyric | Workup 1 | 2x, 3x, 4x | 85% | 730, 800, 870 |
| E-111 | 3 | E-1 | Butyric | Workup 2 | 1x | 38% | 864 |
| E-255* | 1 | A-11 | Butyric | Workup 1 | 2x | 3% | 892 |
| E-256* | 1 | A-11 | Butyric | Workup 1 | 3x | 5.6% | 964 |
| E-85* | 1 | A-11 | Butyric | Workup 1 | 3x |  | 964 |
| E-257* | 1 | A-11 | Butyric | Workup 1 | 4x | 3% | 1036 |

TABLE 15-continued

Butyrylation/Isobutyrylation Examples

| Compound Entry | Synthesis Method | ALC | Substituent | Reaction Condition (i.e. Workup) | Degree of Substitution | Yield | MS |
|---|---|---|---|---|---|---|---|
| E-24 | 3 | E-1 | Butyric | Workup 1 | 1x | 75 | 864 |
| E-89 | 1 | A-3 | Butyric | n/a | 1x | 9% | 406 |

*isolated from one reaction

Example 49. Formation of Valeric Esters of ALCs

Method 1.

The ALC was taken up in DCM. To this were added pyridine and valeric acid anhydride (1 equiv. pyridine/1 equiv. valeric acid anhydride). The mixture was stirred at room overnight or over the weekend and was then poured on an aqueous citric acid solution (5% or 10%) at RT and was stirred for 15 min. The aqueous phase was extracted with EtOAc (2×) and was afterwards brought to pH=8 with solid $Na_2CO_3$. The alkaline aqueous layer was extracted with EtOAc (2×) and the combined organic phases were washed with water (1×) and saturated aqueous NaCl-solution (1×), dried ($Na_2SO_4$), concentrated to dryness and dried at the oil pump. Products were obtained as colorless solids or foams.

Method 2.

Analogue to 2A but after stirring at RT for 2 h additional pyridine (2 equiv.) and valeric acid anhydride (2 equiv.) were added and stirring was continued overnight. Products were obtained as colorless foams or solids.

Method 3.

The ALC was taken up in DCM. To this were added pyridine (4 equiv.) and valeric acid anhydride (4 equiv.). The mixture was stirred at room overnight or over the weekend. Additional pyridine (2 equiv.) and valeric acid anhydride (2 equiv.) were added and the mixture was stirred overnight. Reaction mixture was filled into a separation funnel and washed with saturated aqueous NH4Cl-solution (3×) and water (3×). The organic phase was dried ($Na_2SO_4$) and concentrated to dryness. The residue was co-evaporated with toluene (3×) and with DCM (3×). Afterwards the crude product was purified by column chromatography on silica gel. Eluent: Chloroform/Isopropanol/NH3 (7 M in Methanol) 30/1/1

The product was dried at the oil pump. Products were obtained as colorless solids or foams.

Example 50. Formation of Isovaleric Esters of ALCs

Method 1: Isovaleric acid (4.4 equiv./equiv. ALC) and HOBt 85% (4.4 equiv./equiv. ALC) were dissolved in DMF (12.5 mml/mmol ALC). The solution was cooled down to 0-5° C. in an ice-bath. At this temperature a solution of Dicyclohexylcarbodiimide (4.5 equiv./equiv. ALC) in DCM (5 ml/mmol ALC) was added dropwise within 30 min. the solution was kept at this temperature for another 10 min. Then Azithromycin (1 equiv.) was added in one portion. While stirring, the solution was allowed to come to room temperature within 2 h. Stirring was continued for another 2 h at 50° C. The reaction mixture was allowed to stand at RT for 12 h. A white precipitate was removed by suction. The solvent was evaporated completely at 12 mbar and 50° C. The residue was dissolved in DCM (12.5 mL/mmol ALC) and washed with water (7.5/mmol ALC). A small amount of a white precipitate was removed. Then the solution was treated with citric acid (25 mL/mmol ALC, 5%). The aqueous phase was washed with DCM (5 ml/mmol ALC). NaOH 10% was added until the aqueous phase was basic (pH 12) and was washed with DCM (2×10 ml/mmol ALC). After phase separation the organic phase was evaporated to dryness, products were obtained as white solids.

Method 2A.

The ALC was taken up in DCM. To this were added pyridine and isovaleric acid anhydride (1 equiv. pyridine/1 equiv. isovaleric acid anhydride). The mixture was stirred at room overnight or over the weekend and was then poured on an aqueous citric acid solution (5% or 10%) at RT and was stirred for 15 min. The aqueous phase was extracted with EtOAc (2×) and was afterwards brought to pH=8 with solid $Na_2CO_3$. The alkaline aqueous layer was extracted with EtOAc (2×) and the combined organic phases were washed with water (1×) and saturated aqueous NaCl-solution (1×), dried ($Na_2SO_4$), concentrated to dryness and dried at the oil pump. Products were obtained as colorless solids or foams.

TABLE 16

Valeric Ester Examples

| Compound Entry | Synthesis Method | ALC | Overall equiv. of acid or anhydride | Re | Degree of Substitution | Yield | MS m/z ([M + H]+) |
|---|---|---|---|---|---|---|---|
| E-72 | 3 | A-1 | 6 | Amount DCM: 5 mL | 2 | 65% | 917.5 |
| E-558 | 1 | A 2 (Anhydro) | 5 | Anhydro erythromycin products are formed Amount DCM: 25 mL | 1 | 7% | 800.5 |
| E-569 | 3 | A-10 | 6 | Amount DCM: 5 mL | 2 | 45% | 757.5 |
| E-582 | 2 | A-12 | 6 | Amount DCM: 10 mL Citric acid: 10% | 1 | 89% | 675.5 |
| E-411 | 1 | A-15 | 4 | Amount DCM; 25 mL Citric acid: 5% | 1 and 2 | 81% | 878.3 |
| E-412 | | | | | | | 962.3 |
| E-428 | 1 | A-16 | 3 | Amount DCM: 25 mL Citric acid: 5% | 1 and 2 | 83% | 819.0 |
| E-429 | | | | | | | 902.8 |
| E-464 | 1 | A17 | 5 | Amount DCM: 25 mL Citric acid: 5% | 1 | 94% | 861.7 |

Method 2B.

Analogue to 2A but after stirring at room temperature for 2 h additional pyridine (2 equiv.) and isovaleric acid anhydride (2 equiv.) were added and stirring was continued overnight.

Products were obtained as colorless foams or solids.

Method 2C.

The ALC was taken up in DCM. To this were added pyridine (4 equiv.) and isovaleric acid anhydride (4 equiv.). The mixture was stirred at room for approximately 2 h, then a catalytic amount of DMAP was added, followed by another catalytic amount approximately another 2 h later. The mixture was stirred at room temperature for approximately 2 h before additional pyridine (2 equiv.) and isovaleric acid anhydride (2 equiv.) were added. The mixture was stirred at room overnight and then poured on an aqueous citric acid solution (5%) and stirred at room temperature for 30 min. The aqueous phase was extracted with EtOAc and afterwards brought to pH=8 with solid $Na_2CO_3$. The alkaline aqueous layer was extracted with EtOAc (2×) and the combined organic phases were washed with water (1×) and saturated aqueous NaCl-solution (1×), dried ($Na_2SO_4$), concentrated to dryness and dried at the oil pump. Products were obtained as colorless solids or foams.

TABLE 17

Isovaleric Ester Examples

| Compound Entry | Synthesis Method | ALC | Overall equiv. of acid or anhydride | Annotations | Degree of Substitution | Yield | MS m/z ([M + H]$^+$) |
|---|---|---|---|---|---|---|---|
| E-45 | 1 | A-1 | | | 1 | 91% | 833.5 |
| E-557 | 2A | A 2 (Anhydro) | 5 | Anhydro erythromycin products are formed Amount DCM: 25 mL Citric acid: 5% | 1 | 17% | 800.5 |
| E-573 | 2C | A-10 | 6 | Amount DCM: 7.5 mL Citric acid: 5% | 2 | 19% | 757.5 |
| E-583 | 28 | A12 | 6 | Amount DCM: 10 mL Citric acid: 10% | 1 | 83% | 675.5 |
| E-413 | 2A | A-15 | 4 | Amount DCM: 25 mL Citric acid: 5% | 1 | 95% | 878.3 |
| E-431 | 2A | A-16 | 3 | Amount DCM: 25 mL Citric acid: 5% | 2 | 87% | 818.8 |
| E-432 | | | | | | | 902.7 |
| E-467 | 2A | A-17 | 5 | Amount DCM: 25 mL Citric acid: 5% | 1 | 90% | 861.6 |

Example 51. Long Chain (>C5) Fatty Acid Substation of Tildipirosin

Hexanoic acid (290 mg, 2.5 mmol) was taken up in 5 mL dichloromethane (DCM). Compound A-16 (367 mg, 0.5 mmol) and 4-Dimethylaminopyridine (DMAP) (336 mg, 2.75 mmol) were added and the resulting solution was cooled in an ice bath for approximately 10 minutes. At this point, dicyclohexylcarbodiimide (DCC) (567 mg, 2.75 mmol) was added slowly. The reaction was stirred continually at this temperature for 5 minutes and then progressively warmed to room temperature where it was stirred overnight. Dicyclohexylurea (DCU) that was formed during the reaction is filtered off and discarded. The filtrate was collected and then washed with a saturated solution of ammonium chloride (3×), sodium hydrogencarbonate (3×), water (1×) and dried over anhydrous $Na_2SO_4$. The solvent was evaporated in vacuo. This was followed by re-dissolving the residue in a small volume of methanol. The solution was transported dropwise into ice-cold water (2× volume of methanol) and stored in the freezer overnight. The precipitated product was filtered off and dried under high-vacuum to produce a mixture of E-437, E-438 and E-439 (56%).

This esterification conditions can be extended for other acids.

TABLE 18

Long chain fatty acid substitution of ALC

| Compound Entry | Acid | Substituent equivalent | Degree of Substitution | Yield | MS |
|---|---|---|---|---|---|
| E-437, E-438, E-439 | Hexanoic acid | 5 | 2 and 3 | 56% | 931.7 1028.8 |
| E-440, E-441, E-442 | Heptanoic acid | 5 | 1, 2 and 3 | 46% | 846.9 959.3 1071.9 |
| E-445 | Octanoic acid | 5 | 3 | 17% | 1113.5 |
| E-447, E-448 | Decanoic acid | 5 | 2 and 3 | 41% | 1043.3 1197.5 |
| E-450, E-451 | Dodecanoic acid | 5 | 2 and 3 | 60% | 1099.5 1281.4 |

Example 52. General Procedure for Preparing Cores A-13 and A-14

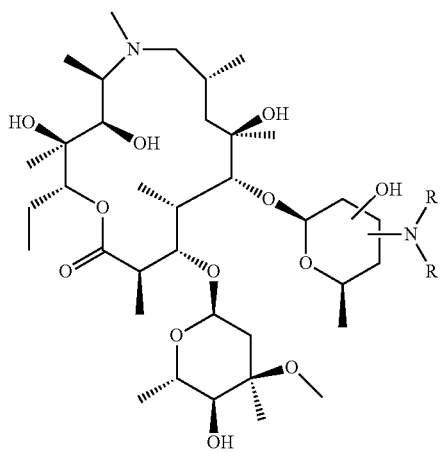

Macrolide (1 mmol) is dissolved in DMF (500 µl). Epichlorohydrin (1 mL) is added and the mixture is heated to 80° C. for 12 h. When MS analysis indicates complete conversion, all volatiles are removed in vacuo and the residue is dissolved in ethanol (1 ml). The solution is poured into 25 ml of water. The precipitate is isolated and can be used directly for the next step or is chromatographed to obtain the pure epoxide.

The following macrolides were used to form epoxides as precursor to the desired cores.

TABLE 19

Epoxide Formation

| Entry | Macrolide | MW epoxide | Yield |
|---|---|---|---|
| 1 | Azithromycin | 703 | 25% |
| 2 | Gamithromycin | 731 | 12% |
| 3 | 3-decladinosyl-3-oxoazithromycin | 543 | 5% |
| 4 | Tildipirosin | 689 | 5% |

Epoxide (1 mmol) is dissolved in 2-propanol (500 µl), and an excess of 5 equivalent of an amine is added. The mixture is heated from 12 h to 100 h at 80° C. When MS indicates complete conversion, all volatiles are evaporated and the residue subjected to chromatography to separate the 2 regioisomeric amines.

TABLE 20

| | | | | | | | |
|---|---|---|---|---|---|---|---|
| | | | Epoxide opening by amines | | | | |
| Entry (Table 9) | Amine | Epoxide opening position | $R^1$ | $R^2$ | $[M + H]^+$ | Yield [%] | Comment |
| 1 | dimethylamine | 3' | Me | Me | 749 | 66 | NMR identical to azithromycin |
| | | 2' | | | | 22 | regioisomer of Azithromycin |
| 1 | morpholine | 3' (A-13.1) | $R^1 = R^2$ = morpholine ring | | 791 | 30 | unpolar product |
| | | 2' (A-13.2) | | | | 61 | polar product |
| 1 | diethanolamine | 3' (A-14.1) | $C_2H_4OH$ | $C_2H_4OH$ | 809 | 22 | unpolar product |
| | | 2' (A-14.2) | | | | 47 | polar product |
| 1 | ammonia | | H | H | 721 | n.d.* | |
| 1 | N-methyl hydroxylamine | | Me | OH | 751 | n.d.* | |
| 1 | Iminodiacetic acid diethylester | | —$CH_2C(O)OEt$ | —$CH_2C(O)OEt$ | 893 | n.d.* | some cyclized product with $[M + H]^+ = 865$ is formed, too |
| 2 | morpholine | | $R^1 = R^2$ = morpholine ring | | | n.d.* | |

*n.d. not determined

Example 53. Further Acylation Reactions of ALC

Method 1:

Compound A-1 (2000 mg, 2.67 mmol) was taken up in 10 mL dichloromethane and stirred. Separately 4.4 eq of a carboxylic acid and 4.4 eq of 1,1'-Carbonyldiimidazole were solved in dichloromethane (10 mL) and stirred over 20 min. Both solutions were unified and stirred continually at room temperature. The dichloromethane phase was washed with saturated NaHCO$_3$ solution (2×) and dried with Na$_2$SO$_4$ (anhydrous). The solvent was evaporated in vacuo to produce a white foam containing products of reaction.

Method 2:

Compound E-1 (265 mg, 0.33 mmol) was taken up in 10 mL dichloromethane and stirred. Separately 1.6 eq of methoxyacetic acid and 1.6 eq of 1,1'-Carbonyldiimidazole were solved in dichloromethane (5 mL) and stirred over 20 min. Both solutions were unified and stirred continually at room temperature. The reaction solution was washed with 5% citric acid three times to extract the product. Acidic solution was then washed with ethyl acetate (2×) and afterwards neutralized with Na$_2$CO$_3$. Product was extracted with ethyl acetate (3×). The solution was washed with a saturated solution of sodium chloride (2×), water (2×) and dried over anhydrous Na$_2$SO$_4$. The solvent was evaporated in vacuo to produce a white foam containing E-12 (238 mg, 90%).

Workup 1:

Column chromatography over silica gel was carried out to separate different products. As eluent a mixture of chloroform, 2-propanol and ammonia in methanol (60:1:1) was used. The solvent was evaporated in vacuo.

Workup 2:

Column chromatography over silica gel was carried out to separate different products. As eluent a mixture of cyclohexane, acetone (3:1) with 0.5% triethylamine was used. The solvent was evaporated in vacuo.

TABLE 21

Typical Products from the Acylation Procedures (2)

| Cpd Entry | Synthesis Method | Carboxylic acid | ALC | Reaction Condition (i.e. Workup) | Degree of Substitution | Yield | MS |
|---|---|---|---|---|---|---|---|
| E-545 | 1 | Cyclopropanecarboxylic acid | A-1 | Workup 1 | 1x | 30% | 817 |
| E-546 | 1 | Cyclobutanecarboxylic acid | A-1 | Workup 1 | 1x | 10% | 830 |
| E-546, E-560, E-561 | 1 | Cyclobutanecarboxylic acid | A-1 | Workup 1 | 1x, 2x, 3x | 22.5% | 830, 913, 995 |
| E-547 | 1 | Nicotinic acid | A-1 | Workup 2 | 1x | 10.3% | 854 |
| E-547, E-562 | 1 | Nicotinic acid | A-1 | Workup 2 | 1x, 2x | 11.8% | 854, 959 |
| E-551 | 1 | Methoxyacetic acid | A-1 | Workup 1 | 1x | 4.4 | 820 |
| E-14, E-22, E-559 | 1 | Methoxyacetic acid | A-1 |  | 2x, 3x, 4x | Reaction solution | 893, 965, 1037 |
| E-12 | 2 | Methoxyacetic acid | E-1 | none | 1x | 90% | 866 |
| E-81 | 1 | 3-Phenylpropionic acid | A-1 | Workup 1 | 1x | 30% | 881 |
| E-544 | 1* | Indole-3-propionic acid | A-1 | Workup 1 | 1x | 45% | 920 |

*instead of 1,1'-carbonyl diimidazole, HATU was used as coupling agent.

Example 54. Synthesis of E-541 and E-542

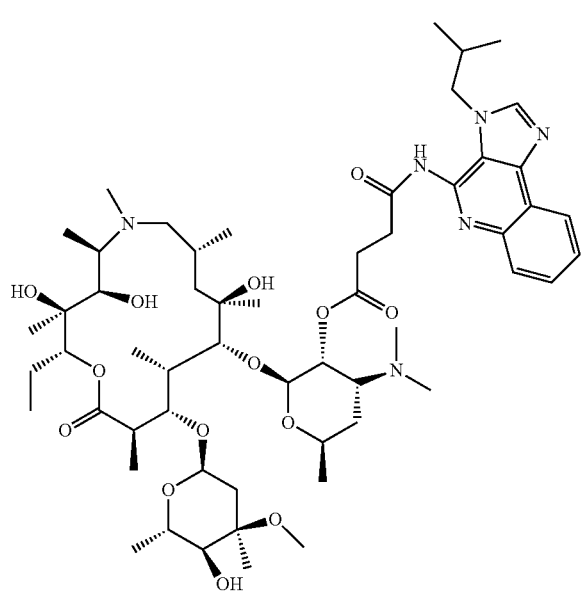

E-541

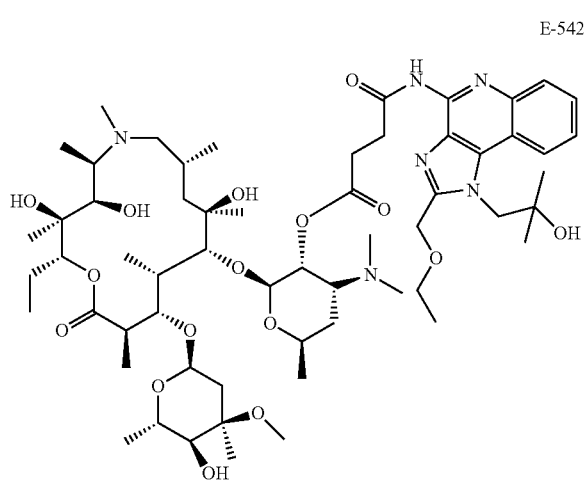

E-542

E-27 (1.2 mmol) and Quinoline-amine (1 eq) was taken up in DCM (5 mL). To this was added HATU (1.2 eq) neat. The reaction was stirred overnight at room temperature. Reaction was very sluggish an additional 0.5 eq of HATU was added. Reaction was stirred for 2 days or disappearance of starting material was observed (TLC or MS). Reaction solution was removed in vacuo and the crude material directly purified by chromatography to get the desired product.

TABLE 22

Decoration of ALC (E-27) with potential TLR-agents

| Cpd Entry | Quinoline | Degree of Substitution | Yield | MS |
|---|---|---|---|---|
| E-541 | Imiquimod | 1 | 35% | 1071 |
| E-542 | Resiquimod | 1 | 25% | 1145 |

Example 55. Examples of Polyamines as ALC

These ALCs can be prepared by reacting symmetrical or unsymmetrical di- or polyepoxides with secondary amines. This will provide ALCs that contains common structural element of 2 or more alcohols, vicinally neighbored by a tertiary amine. Some polyamines are also commercially available.

Alternatively, ALCs can be prepared by reacting epoxides with diethanolamine. The reaction products are containing 2-hydroxy tertiary amines.

General Procedure for Preparation of Some Polyamine ALC Bearing Hydroxy Functionalities:

Polyamine (1 mmol) containing at least 2 NH-functions and the epoxide are mixed and heated without solvent to 80° C. Excess epoxide can be removed by column chromatography selectively. Products are sufficient, when at least 2 tertiary ß-hydroxyamines are present.

TABLE 23

Examples of Polyamine ALCs

| Entry | Amine | Epoxide | Eq. of Epoxide | Reaction time | [M + H]+ Product | Yield | Remark |
|---|---|---|---|---|---|---|---|
| 1 | hexamethylene diamine | 1,2-epoxytetradecane | 4.2 | 40 h | 966 | n.d. | product contains a small amount of triple alkylation |
| 2 | bis-(hexamethylene)triamine | cyclohexene oxide | 12 | 240 h | 608 | n.d. | main product is tetraalkylated |

Entry 1

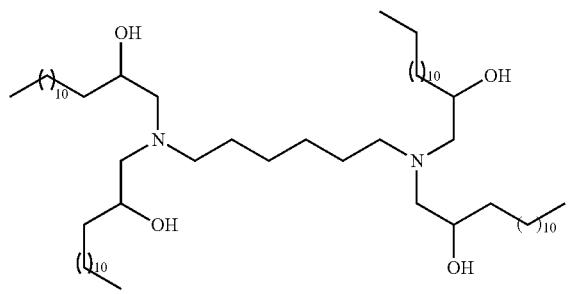

Entry 2

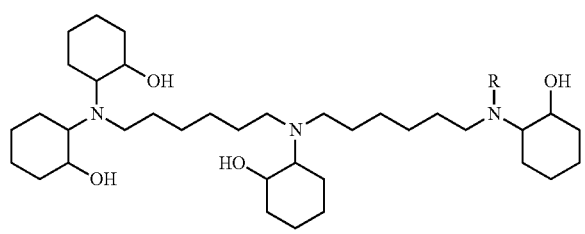

R = H (tetraalkylated)
= 2-hydroxycyclohexal (pentaalkylated)

Reactions of Polyepoxides with Amines:

Corresponding polyepoxide (1 mmol) is mixed with 1.05 mmol secondary amine per epoxide function and heated to 80° C. without solvent for 12 h.

TABLE 24

Further Examples Polyamine ALCs

| Entry | Epoxide | Amine | [M + H]+ Product | Yield |
|---|---|---|---|---|
| 1 | 1,2,7,8-diepoxyoctane | morpholine | 317 | 100% |
| 2 | Diglycidyl ethylenglycol | morpholine | 377 | 90% |

Entry 1

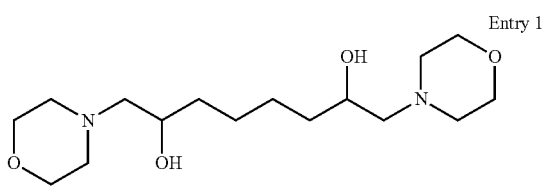

Entry 2

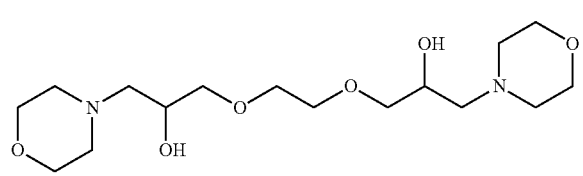

(C2 Table 16)

Synthesis of E-552

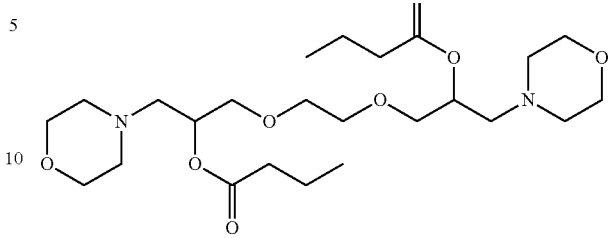

1.45 g of 1,10-dimorpholino-2,9-dihydroxy-4,7-dioxadecane are combined with 1.5 ml of butyric anhydride in 5 ml of chloroform. After stirring for 1 h, MS indicates complete conversion ([M+H]+=517). The mixture is extracted with 2 N KOH, saturated aqueous sodium bicarbonate solution and brine, dried and chromatographed over silica gel to obtain 1.57 g of the target compound (72%).

Example 56. Substitution of Polyamine ALC (See Table 1, Entry A-19)

Substitution ALC A-19.1/A-20.1/A-20.2
Method 1:

N-Hydroxyalkyl compound (5 mmol) was suspended in excess carboxyl acid anhydride (>100 mmol, >20 eq.) in a round bottom flask while stirring (magnetic stir bar, 500 rpm). The mixture was cooled in an ice bath and sulfuric acid (>96%, 3 drops) was carefully added as catalyst. Stirring was continued until a clear solution was obtained. When ESI-MS indicated full conversion of starting materials the reaction mixture was poured on ice. The system was stirred for 2 or more hours in order to hydrolyze any anhydride. The mixture was neutralized by addition of sodium bicarbonate and extracted with dichloromethane (3x). Separation of organic phase, drying over sodium sulfate and evaporation of any volatiles in vacuo yielded the product as colorless oil.

Method 2.

Carboxylic acid (1.5 eq per hydroxyl group) was placed into a round bottom flask along with a stir bar and carbonyl diimidazole (CDI, 1.6 eq per hydroxyl group). Dichloromethane (DCM, 10 mL per gram carboxylic acid) was added carefully while stirring (500 rpm) at ambient temperature. Immediate formation of carbon dioxide indicated conversion of corresponding acid to the acyl donor (caution: too quick $CO_2$ formation may result in strong foaming. Do not seal the flask!). After a couple of minutes, a clear solution was obtained and stirring was continued for 15 minutes. N-Hydroxyalkyl compound (5 mmol) was added at ambient temperature and the reaction mixture was stirred overnight. When ESI-MS indicated full conversion of starting materials the reaction was quenched by addition of methanol, converting excess acyl donor to methyl ester. The system was diluted by addition of further DCM and was subject to extraction with saturated sodium bicarbonate solution (3×). Separation of organic phase, drying over sodium sulfate and evaporation of any volatiles in vacuo yielded the product as colorless oil.

TABLE 25

Substitution of ALC A-19.1/A-20.1/A-20.2

| Compound Entry | Synthesis Method | ALC | Degree of Substitution | Yield | MS [M + H]+ |
|---|---|---|---|---|---|
| E-524 | 1 | A-19.1 | Di acyl | 85% | 259, M + H+ |
| E-576 | 1 | A-19.1 | Mono acyl | 23% | 217, M + H+ |
| E-525 | 1 | A-19.1 | Di acyl | 94% | 287, M + H+ |
| E-577 | 1 | A-19.1 | Mono acyl | 12% | 231, M + H+ |
| E-526 | 2 | A-19.1 | Di acyl | 87% | 315, M + H+ |
| E-578 | 2 | A-19.1 | Mono acyl | 45% | 245, M + H+ |
| E-527 | 1 | A-19.1 | Di acyl | 56% | 315, M + H+ |
| E-529 | 1 | A-19.1 | Di acyl | 8% | 343, M + H+ |
| E-530 | 2 | A-19.1 | Di acyl | 76% | 499, M + H+ |
| E-538 | 1 | A-20.1 | Tri acyl | 85% | 299, M + Na+ |
| E-537 | 1 | A-20.1 | Tri acyl | 76% | 383, M + Na+ |
| E-580 | 1 | A-20.2 | Tri acyl | 61% | 391, M + Na+; 368, M− |

Substitution ALC A-19.2

1,1'-Carbonyldiimidazole was dissolved in dichloromethane (dry, 25 mL) and to this was added the carboxylic acid slowly at room temperature. The solution was stirred at room temperature before a suspension of N;N,N',N'-tetrakis (2-hydroxyethyl)-ethylendiamine (A-19.2) in dichloromethane (dry, 5 mL) was added in one portion at room temperature and the mixture was stirred at RT. The reaction mixture was filled into a separation funnel and washed. The organic phase was dried ($Na_2SO_4$) and concentrated to dryness in vacuo. The crude product was purified by column chromatography.

Eluent: $CHCl_3$:Isopropanol:$NH_3$ (7 M in MeOH)=60:1:1.

Analytical Data:

E-531:

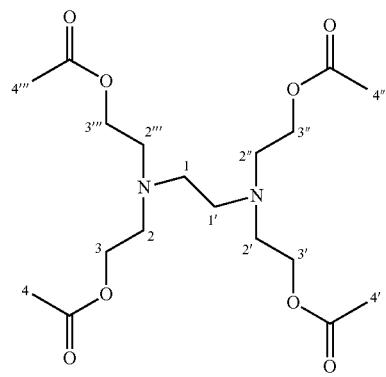 [SMILES: CC(=O)OCCN(CCOC(C)=O)CCN(CCOC(C)=O)CCOC(C)=O]

ESI-MS (positive): m/z=405.2 [M+H]+, 427.1 [M+Na]+

Purity according to HPLC (ELSD): >99.9%

$^1$H-NMR (300 MHz, $CDCl_3$): 1.98 (s, 12H, 4-H, 4'-H, 4"-H, 4'''-H), 2.57 (s, 4H, 1-H, 1'H), 2.72 (t, $J_{2,3}$ and $J_{2',3'}$, $J_{2'',3''}$, $J_{2''',3'''}$=6.04, 8 H, 2-H, 2'-H, 2"-H, 2'''-H), 2.72 (t, $J_{3,2}$ and $J_{3',2'}$, $J_{3'',2''}$, $J_{3''',2'''}$=4.04, 8 H, 2-H, 2'-H, 2"-H, 2'''-H).

$^{13}$C-NMR (75 MHz, $CDCl_3$): 20.77 (q, C-4, C-4', C-4", C-4'''), 53.15 (t, C-2, C-2', C-2", C-2'''), 53.44 (t, C-1, C-1'), 62.43 (t, C-3, C-3', C-3", C-3'''), 170.74 (s, 4×C=O).

TABLE 26

Substitution of ALC A-19.12

| Cpd Entry | ALC | Amount (A-19.2) | Amount Carboxylic acid (mg) | Amount CDI | Time for stirring carboxylic acid and CDI | Reaction Time | Washing steps | Yield |
|---|---|---|---|---|---|---|---|---|
| E-531 | A-19.2 | 521 mg (73.4%) 1.64 mmol | Glacial acetic acid 800 µL 13.99 mmol | 2.49 g 15.35 mmol | 35 min | 22h 30 min | NaHCO$_3$ (2 × 20 mL) | 297 mg (45%) |
| E-532 | A-19.2 | 498 mg (73.4%) 1.55 mmol | Propionic acid 943 µL 12.6 mmol | 2.46 g 15.17 mmol | 20 min with argon stream | 1.5 h with argon stream 69 h 45 min under argon atmosphere | Water (1 × 20 mL) sat. NaHCO$_3$ (2 × 20 mL) | 144 mg (20%) |
| E-533 | A-19.2 | 495 mg (73.4%) 1.54 mmol | Butyric acid 1.2 mL 13.55 mmol | 2.51 g 15.45 mmol | 35 min | 46 h 45 min | NaHCO$_3$ (2 × 20 mL) | 20 mg (pure) 224 mg (with impuri-Ties Overall yield: (19%) |

E-532:

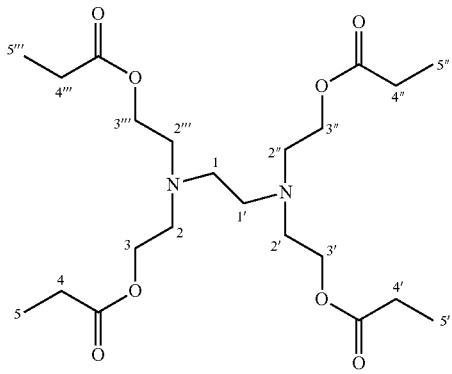 [SMILES: CCC(=O)OCCN(CCOC(=O)CC)CCN(CCOC(=O)CC)CCOC(=O)CC]

ESI-MS (positive): m/z=461.2 [M+H]⁺, 483.3 [M+Na]⁺
Purity according to HPLC (ELSD): >99.9%
¹H-NMR (300 MHz, CDCl₃): 1.08 (t, J5,4, $J_{5',4'}$, $J_{5'',4''}$, $J_{5''',4'''}$=7.6 Hz, 12H, 5-H, 5'-H, 5''-H, 5'''-H), 2.27 (q, $J_{4,5}$, $J_{4',5'}$, $J_{4'',5''}$, $J_{4''',5'''}$=7.6 Hz), 2.57, 4-H, 4'-H, 4''-H, 4''' 2.60 (s, 4H, 1-H, 1'H), 2.74 (t, $J_{2,3}$ and $J_{2',3'}$, $J_{2'',3''}$, $J_{2''',3'''}$=6.04, 8 H, 2-H, 2'-H, 2''-H, 2'''-H), 4.07 (t, $J_{3,2}$ and $J_{3',2'}$, $J_{3'',2''}$, $J_{3''',2'''}$=6.04, 8 H, 2-H, 2'-H, 2''-H, 2'''-H).
¹³C-NMR (75 MHz, CDCl₃): 8.96 (q, C-5, C-5', C-5'', C-5'''), 27.44 (t, C-4, C-4', C-4'', C-4'''), 53.22 (t, C-2, C-2', C-2'', C-2'''), 53.54 (t, C-1, C-1'), 62.36 (t, C-3, C-3', C-3'', C-3'''), 172.20 (s, 4×C=O).

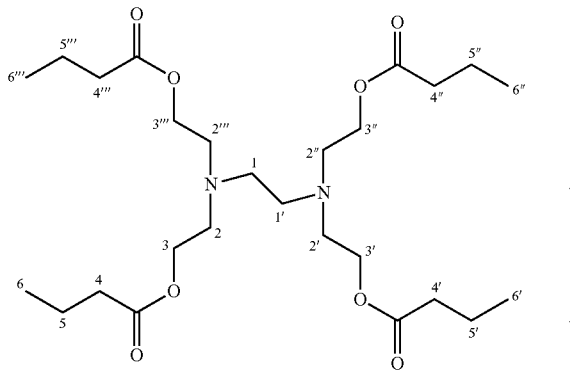

E-533:
ESI-MS (positive): m/z=617.3 [M+H]⁺, 539.3 [M+Na]⁺
Purity according to HPLC (ELSD): >99.9%
¹³C-NMR (75 MHz, CDCl₃): 13.53 (q, C-6, C-6', C-6'', C-6'''), 18.26 (t, C-5, C-5', C-5'', C-5'''), 36.00 (t, C-4, C-4', C-4'', C-4'''), 53.21 (t, C-2, C-2', C-2'', C-2'''), 53.45 (t, C-1, C-1'), 62.24 (t, C-3, C-3', C-3'', C-3'''), 173.36 (s, 4×C=O):
Substitution ALC A-19.3
H-L-orn(Boc)2CT Resin (0.68 mmol/g, 100-200 mesh, 2.99 g, 2.07 mmol) was filled into a 20 mL syringe with frit. Dichloromethane (dry, 10 mL), MeOH (2 mL) and diisopropylethylamine (2 mL) are added to the resin for endcapping. The mixture was shaken at room temperature for 30 min, then the liquid was sucked off and the resin was washed (3× dimethylformamide 15 mL, 1× diethylether 15 mL).
The resin was filled into a 100 mL round bottom flask. DMF (25 mL) was added and the resin was swollen for 5 min. Then diisopropylethylamine (3.8 mL, 22.3 mmol) and 2-bromoethanol (1.434 mL, 20.3 mmol) were added subsequently at room temperature. The reaction mixture was stirred at 60° C. (bath temperature) for 24 h.
The resin was filled into a 20 mL syringe with frit and was washed: 4× dimethylformamide (20 mL), 3× methanol (20 mL), 3× dichloromethane (20 mL), 3× diethyl ether (20 mL).
Half of the resin (1.035 mmol) was filled into a 20 mL syringe with frit.
Valeric acid (568 µL, 5.69 mmol) was added to a mixture of dimethylformamide/dichloro-methane 1:1 (10 mL). HOBt*H₂O (870 mg, 5.69 mmol) was added and mixture was stirred at room temperature for 5 min before diisopropylcarbodiimide (881 µL, 5.69 mmol) was added. Stirring at room temperature was continued for 10 min, then the whole mixture was added to the resin and the resin was shaken at room temperature for 5 h.
The liquid was sucked off and the resin was washed: 4× dimethylformamide (10 mL), 3× methanol (10 mL), 3× dichloromethane (10 mL), 3×diethyl ether (10 mL).
A test cleavage showed the product by mass spectrometry ESI-MS (positive): m/z=261.1 [M+H]⁺

Example 57. Synthesis of 2'-O-(2-Ferrocenyl) acetyl-azithromycin E-549

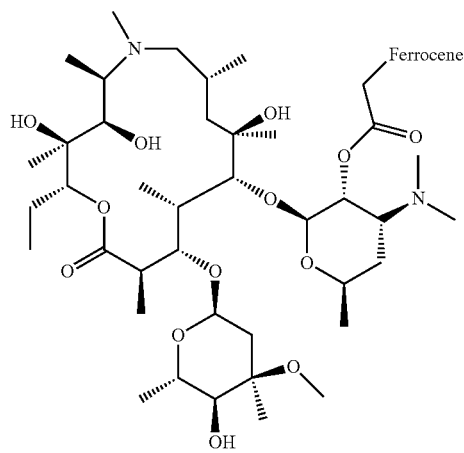

ALC A-1 (0.25 mmol) was dissolved in dry dichloromethane (5 mL). To this was added EDCI (2 eq., 0.5 mmol) and 2-ferrocenyl acetic acid (1.1 eq., 0.28 mmol). The reaction was stirred overnight at room temperature. The solvent was removed in vacuo and the resulting white amorphous foam. The resulting crude product was purified by column chromatography with a gradient starting at 10% of acetone in cyclohexane (0.2% Et₃N).

Example 58. Synthesis of E-258

Compound A-11/E-16 was dissolved in dry dichloromethane (DCM) in a round bottom flask equipped with magnetic stir bar. Penta-O-acetyl-α-D-mannopyranoside (1.2 eq) was added and the system was cooled in an ice bath while stirring (300 rpm). Catalytic amount of boron trifluoride diethyl ether complex was carefully added dropwise and the system was allowed to warm up while stirring overnight. Upon dilution with further DCM the mixture was subject to extraction with saturated sodium bicarbonate solution (3×). Separation of organic phase, drying over sodium sulfate and evaporation of any volatiles in vacuo yielded the product as colorless oil or beige to off-white foam. [M+H]⁺ m/z 907 The reaction conditions also produced the des-cladinosyl product E-600.

Example 59. Synthesis of E-550

350 mg of compound E 77 are dissolved with 15 ml of carbon disulfide. 250 mg of sulfur are added and the mixture is stirred for 7 days. The mixture is extracted with 5% aqueous citric acid solution. The aqueous extract is combined with 10 ml of ethyl acetate and made alkaline by addition of sodium carbonate with intense stirring. The organic phase is separated, washed with brine, dried over sodium sulfate and concentrated in vacuo to yield 280 mg of a product, that contains various higher sulfides along with some starting material, as indicated by mass spectrometry ($[M+H]^+$=969, 1001, 1033, 1065).

Example 60. Pharmacokinetics

The distribution of compounds to target organs is of specific importance to the efficacy of anti-infective compounds. To determine distribution the compounds are formulated and administered to a suitable animal model. Compounds were administered p.o. 10 mg/kg in 2% citric acid in BALBc and organs were recovered at 6 h. Organs were extracted in Acetonitrile (6× volume of the sample), centrifuged at 14000 g for 5 minutes. Samples were analysed by LCMSMS (SCIEX 4500). Data are the mean of 3 animals.

Example 61. Selection of ALC Via Concentration into Immune Cells

The distribution of compounds to target cells is of specific importance to the efficacy of anti-infective compounds. To determine uptake the compounds are dissolved in DMSO or citric acid and mixed with whole blood, plasma or cell medium. To these solutions are added cultured macrophages, cultured immune cells, bone marrow derived macrophages, peritoneal macrophages or buffy coat cells. The mixture is incubated at 37° C. for 1, 2, or 3 hours. After incubation, the immune cells are separated from the medium and the concentration of the compounds is determined by extraction in Acetonitrile (6× volume of the sample), followed by centrifugation at 14000 g for 5 minutes. The resulting extracts are analyzed by LCMSMS (SCIEX 4500 in positive mode). Data are the mean of 3 animals.

Other Embodiments

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Abbreviations

The following abbreviations were used as noted:
MeOH: methanol
NaHCO$_3$: sodium bicarbonate
K$_2$CO$_3$: potassium carbonate
MS: mass spectrometry
DMSO: dimethyl sulfoxide
TLC: thin layer chromatography
Et$_3$N: triethylamine
EtOAc: ethyl acetate
DCM: dichloromethane
NH$_4$Cl: ammonium chloride
THF: tetrahydrofuran
Na$_2$CO$_3$: sodium carbonate
EDCI: N-Ethyl-N'-(3-dimethylaminopropyl)carbodiimide hydrochloride
DMAP: 4-dimethylamino pyridine
HATU   O-(7-Azabenzotriazol-1-yl)-N,N,N',N'-tetramethyluronium-hexafluorphosphate
DIPEA N,N-Diisopropylethylamine

CITATION LIST PATENT LITERATURE

US2007238882A1
US2003105066A1
US2008221158A1
US2008027012A1
U.S. Pat. No. 6,455,576B1
U.S. Pat. No. 5,677,287A
EP1748994B1
WO2007025632A2
WO9530641A1
WO0002567A1

CITATIONS—NON PATENT LITERATURE

[1] L. J. Ignarro, *Nitric Oxide Biology and Pathobiology*, Academic Press, 2000, p. xvii.
[2] H. Al-Sa'doni, A. Ferro, 2000, *Clinical Science*, 98, pp 507-520.
[3] P. G. Wang et. al., *Chem. Rev.*, 2002, 102 (4), pp 1091-1134.
[4] E. Oberdisse, E. Hackenthal, K. Kuschinsky, *Pharmakologie and Toxikologie*, Kapitel 16.2.6, Springer-Verlag, Berlin Heidelberg New York, 2001, pp 292-293.
[5] G. H. Hakimelahi, H. Sharghi, H. Zarrinmayeh, A. Khalafi-Nezhad, *Helv. Chim. Acta.* 1984, 67, 906-915, and literature cited therein.
[6] G. A. Olah et al., *J. Org. Chem.* 1990, 55 (17), 5179-5180.
[7] H. Burton, P. F. G. Praill, *J. Chem. Soc.* 1955, 729-731.
[8] E. Santaniello, M. Ravasi, P. Ferraboschi, *J. Org. Chem.* 1983, 48, 739-740.
[9] J. A. R. Rodrigues, A. P. O. Filho, P. J. S. Moran, *Synth. Comm.* 1999, 29 (12), 2169-2174.
[10] F. Francis et al., *Berichte* 1906, 39, 3798-3804.
[11] M. E. Kurz, E. P. Zahora, D. Layman, *J. Org. Chem.* 1973, 38 (13), 2277-2281.
[12] M. E. Kurz, E. Woodby, *J. Org. Chem.* 1976, 41 (14).
[13] Ronchetti D, Borghi V, Gaitan G, Herrero J F, Impagnatiello F. Br J Pharmacol. 2009 September; 158(2):569-79
[14] Lemaire S, Van Bambeke F, Tulkens P M. Antimicrob Agents Chemother. 2009 September; 53(9):3734-43
[15] Martinez L R, Han G, Chacko M, Mihu M R, Jacobson M, Gialanella P, Friedman A J, Nosanchuk J D, Friedman J M. J Invest Dermatol. 2009 October; 129(10):2463-9
[16] N. Pietrzik, C. Schips, T. Ziegler, *Synthesis* 2008, 519-526, and literature cited therein.
[17] R. Shan, C. Velaquez, E. E. Knaus, *J. Med Chem.* 2004, 47, 244-261.
[18] Volante, R. P., Tethed. Lett. 1981, 22, 3119-3122
[19] Silveira et al., *Tethed. Lett.* 2007, 48, 7469-7471
malignant disease.

What is claimed is:

1. A compound, or salt thereof, comprising an Amphiphilic Lysosomally trapped Compound (ALC), wherein the ALC is a compound of Formula 6:

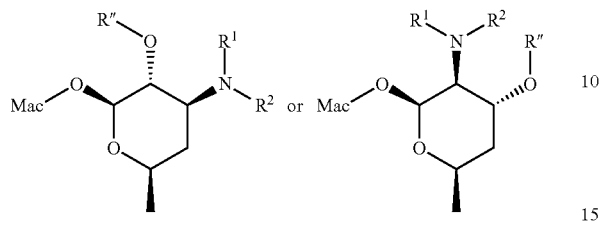

or a salt thereof, wherein:

each R" is independently
- —H;
- —NO$_{(y)}$ wherein y is 2;
- —C(=O)OR$^3$, or —C(=O)R$^3$;

R$^1$ and R$^2$ are independently of each other H, OH, OR$^4$, —C$_1$-C$_{10}$ alkyl, alkenyl, alkynyl, aryl, heteroaryl, alkylaryl, or alkylheteroaryl;

wherein alkyl, alkenyl, alkynyl, aryl, heteroaryl, alkylaryl and alkylheteroaryl groups are optionally modified with one to five substituents selected independently from: (C$_2$-C$_9$)heterocycloalkyl, nitro (—NO$_2$), R$^4$C(=O)O—, and —XNO$_{(y)}$ wherein X is O, and y is 2;

or N(R$^1$R$^2$) is an aziridine, azetidine, pyrrolidine, piperidine, azepane, azocane, 1-substituted piperazine, or morpholine moiety;

R$^3$ is —C$_1$-C$_{10}$ alkyl, alkynyl, aryl, heteroaryl, alkylaryl, or alkylheteroaryl;

wherein alkyl, alkynyl, aryl, heteroaryl, alkylaryl and alkylheteroaryl groups are optionally modified with one to five substituents selected independently from: (C$_2$-C$_9$)heterocycloalkyl nitro (—NO$_2$), R$^6$C(=O)O—, and —XNO$_{(y)}$ wherein X is O, and y is 2;

R$^4$ and R$^6$ are each independently:
- —H;
- —(C$_1$-C$_{12}$)alkyl;
- —(C$_2$-C$_{12}$)alkenyl;
- —(C$_2$-C$_{12}$)alkynyl;
- —(C$_1$-C$_8$)[(C$_1$-C$_4$)alkoxy]alkyl;
- —(C$_2$-C$_8$)[(C$_1$-C$_4$)alkoxy]alkenyl;
- —(C$_6$-C$_{10}$)aryl-(C$_1$-C$_5$)alkyl; or
- —(C$_2$-C$_9$)heteroaryl-(C$_1$-C$_5$)alkyl;

wherein alkyl, alkenyl, and alkynyl are optionally modified with one to five substituents selected independently from (C$_2$-C$_9$)heterocycloalkyl, nitro (—NO$_2$), and —XNO$_y$ wherein X is O, and y is 2;

Mac is a macrolide ring or macrolide ring system of the formula:

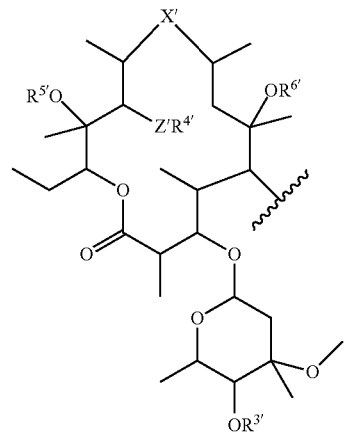

wherein
X' is —N(CH$_3$)—CH$_2$—;
- —CH$_2$—N[(CH$_2$)$_n$—CH$_3$]— wherein n is 0-4;
- —C(=O)—;
- —C(=NOR$^{8'}$)—; or
- —C(=NR$^{12'}$)—;

R$^{3'}$ is:
- —H;
- —NO$_{(y)}$ wherein y is 2;
- —C(=O)OR$^{7'}$, or —C(=O)R$^{7'}$;

if Z' is O, R$^{4'}$ is:
- —H;
- —NO$_{(y)}$ wherein y is 2;
- —C(=O)OR$^{7'}$, or —C(=O)R$^{7'}$;

R$^{5'}$ is:
- —H;
- —NO$_{(y)}$ wherein y is 2;
- —C(=O)OR$^{7'}$, or —C(=O)R$^{7'}$;

or Z' is O or NR$^{9'}$ and the R$^{4'}$ and R$^{5'}$ bearing atoms are connected via —C(=O)—;

or the R$^{4'}$ and R$^{5'}$ bearing atoms are connected via W';

W' is:
- —(-)CH—(C$_1$-C$_{12}$)alkyl;
- —(-)CH—(C$_3$-C$_{12}$)alkenyl;
- —(-)CH—(C$_3$-C$_{12}$)alkynyl;
- —(-)CH—(C$_1$-C$_8$)[(C$_1$-C$_4$)alkoxy]alkyl; or
- —(-)CH—(C$_2$-C$_8$)[(C$_1$-C$_4$)alkoxy]alkenyl;

wherein alkyl, alkenyl, alkynyl are optionally modified with one to five substituents selected independently from (C$_2$-C$_6$)heterocycloalkyl, nitro (—NO$_2$), R$^{14'}$C(=O)O— and —XNO$_2$; wherein X is O;

R$^{6'}$ is:
- —H;
- —NO$_{(y)}$ wherein y is 2;
- —C(=O)OR$^{7'}$, or —C(=O)R$^{7'}$;

each R$^{7'}$ is independently:
- -H;
- -ferrocene;
- —C$_1$-C$_{10}$ alkyl, alkenyl, alkynyl, aryl, heteroaryl, alkylaryl, or alkylheteroaryl wherein alkyl, alkenyl, alkynyl, aryl, heteroaryl, alkylaryl and alkylheteroaryl groups are optionally modified with one to five substituents selected independently from: (C$_2$-C$_6$)heterocycloalkyl, nitro (—NO$_2$), R$^{14'}$C(=O)O—, and —XNO$_{(y)}$; wherein X is O; and y is 2;

$R^{8'}$ is:
— H;
— $NO_{(y)}$ wherein y is 2;
— C(=O)— $R^{7'}$;
— $(C_1$-$C_{12})$alkyl;
— $(C_2$-$C_{12})$alkenyl;
— $(C_2$-$C_{12})$alkynyl;
— $(C_1$-$C_8)[(C_1$-$C_4)$alkoxy]alkyl;
— $(C_2$-$C_8)[(C_1$-$C_4)$alkoxy]alkenyl;
— $(C_6$-$C_{10})$aryl-$(C_1$-$C_5)$alkyl; or
— $(C_2$-$C_9)$heteroaryl-$(C_1$-$C_5)$alkyl;

$R^{9'}$ is:
— H;
— $NO_{(y)}$ wherein y is 2;
— C(=O)— $R^{7'}$;
— $(C_1$-$C_{12})$alkyl;
— $(C_2$-$C_{12})$alkenyl;
— $(C_2$-$C_{12})$alkynyl;
— $(C_1$-$C_8)[(C_1$-$C_4)$alkoxy]alkyl;
— $(C_2$-$C_8)[(C_1$-$C_4)$alkoxy]alkenyl;
— $(C_6$-$C_{10})$aryl-$(C_1$-$C_5)$alkyl; or
— $(C_2$-$C_9)$heteroaryl-$(C_1$-$C_5)$alkyl;

$R^{12'}$ is:
— H;
— $NO_{(y)}$ wherein y is 2;
— C(=O)— $R^{7'}$;
— $(C_1$-$C_{12})$alkyl;
— $(C_2$-$C_{12})$alkenyl;
— $(C_2$-$C_{12})$alkynyl;
— $(C_1$-$C_8)[(C_1$-$C_4)$alkoxy]alkyl;
— $(C_2$-$C_8)[(C_1$-$C_4)$alkoxy]alkenyl;
— $(C_6$-$C_{10})$aryl-$(C_1$-$C_5)$alkyl; or
— $(C_2$-$C_9)$heteroaryl-$(C_1$-$C_5)$alkyl;

$R^{14'}$ is each independently:
— H;
— $(C_1$-$C_{12})$alkyl;
— $(C_2$-$C_{12})$alkenyl;
— $(C_2$-$C_{12})$alkynyl;
— $(C_1$-$C_8)[(C_1$-$C_4)$alkoxy]alkyl;
— $(C_2$-$C_8)[(C_1$-$C_4)$alkoxy]alkenyl;
— $(C_6$-$C_{10})$aryl-$(C_1$-$C_5)$alkyl; or
— $(C_2$-$C_9)$heteroaryl-$(C_1$-$C_5)$alkyl;

wherein alkyl, alkenyl, alkynyl, aryl and heteroaryl are optionally modified with one to five substituents selected independently from $(C_2$-$C_6)$heterocycloalkyl, nitro (—$NO_2$), and —$XNO_y$; wherein X is O; and y is 2;

wherein the compound comprises at least one moiety consisting of —$ONO_2$ or —$NNO_2$.

2. A non-nitrate salt of a compound of claim 1.

3. A pharmaceutical composition comprising a compound of claim 1, or salt, solvate, or hydrate thereof, and a pharmaceutically acceptable carrier.

4. The composition of claim 3, further comprising an additional therapeutic agent.

5. The compound of claim 1, or salt thereof, wherein R" is —$NO_{(y)}$ wherein y is 2; —C(=O)$OR^3$, or —C(=O)$R^3$.

6. The compound of claim 1, or salt thereof, wherein $R^{3'}$ is —H; —$NO_{(y)}$ wherein y is 2; or —C(=O)$R^{7'}$.

7. The compound of claim 1, or salt thereof, wherein R" is —H; —$NO_{(y)}$ wherein y is 2; or —C(=O)$R^3$.

8. The compound of claim 1, or salt thereof, wherein Z' is O.

9. The compound of claim 1, or salt thereof, wherein $R^{4'}$ is —H; —$NO_{(y)}$ wherein y is 2; or —C(=O)$R^{7'}$.

10. The compound of claim 1, or salt thereof, wherein the ALC is a compound of the formula:

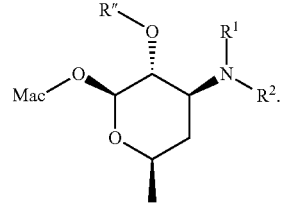

11. The compound of claim 10, or salt thereof, wherein $R^{3'}$ is —$NO_2$, Z' is O, $R^{4'}$ is —H, $R^{5'}$ is —H, $R^{6'}$ is —H, X' is —$N(CH_3)$—$CH_2$—, $R^1$ is $C_1$ alkyl, $R^2$ is $C_1$ alkyl, and R" is —C(=O)$R^3$ wherein $R^3$ is $C_2$ alkyl.

12. The compound of claim 1, or salt thereof, wherein the ALC is a compound of the formula:

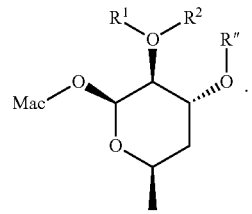

13. The compound of claim 1, or salt thereof, wherein the ALC has an azithromycin, erythromycin, CSY0041, CSY1130, CSY5632, CSY2219, CSY5602, CSY1019, gamithromycin, or clarithromycin core.

14. A method of stimulating immune or epithelial cells to form an anti-infective barrier or anti-infective response comprising contacting the cells with a compound of claim 1, or salt thereof, wherein the contacting results in the intracellular release of a product of Anaerobic Metabolism (PAM) comprising one or more of a molecule type selected from the group consisting of Toll-like-receptor (TLR) ligands, short chain fatty acids (SCFAs), nitric oxide (NO), $H_2S$, sulfides, polyamines, decarboxylated amino acids and phenylpropionic acid from the compound of claim 1, or salt thereof.

15. The method of claim 14, wherein the method releases a short chain fatty acid moiety from the compound of claim 1.

16. The method of claim 15, wherein the method releases a short chain fatty acid moiety containing 2 or more carbons.

17. A method of treating an Amphiphilic Lysosomally trapped Compound-responsive disease, disorder, or symptom thereof in a subject comprising administering to the subject a compound of claim 1, or salt, solvate, or hydrate thereof.

18. The method of claim 17, wherein the disease or disorder is an infectious disease, an inflammatory disease, or a malignant disease.

19. The method of claim 17, further comprising administering an antibacterial compound.

20. The method of claim 17, further comprising administering a macrolide compound.

* * * * *